United States Patent
LeBoeuf et al.

(10) Patent No.: US 11,324,445 B2
(45) Date of Patent: May 10, 2022

(54) HEADSETS WITH ANGLED SENSOR MODULES

(71) Applicant: Valencell, Inc., Raleigh, NC (US)

(72) Inventors: Steven Francis LeBoeuf, Raleigh, NC (US); Jesse Berkley Tucker, Youngsville, NC (US); Michael Edward Aumer, Raleigh, NC (US); Eric Douglas Romesburg, Chapel Hill, NC (US); Joseph Norman Morris, Chapel Hill, NC (US)

(73) Assignee: Valencell, Inc., Raleigh, NC (US)

( * ) Notice: Subject to any disclaimer, the term of this patent is extended or adjusted under 35 U.S.C. 154(b) by 844 days.

(21) Appl. No.: 16/169,375

(22) Filed: Oct. 24, 2018

(65) Prior Publication Data

US 2019/0053764 A1 Feb. 21, 2019

Related U.S. Application Data

(63) Continuation of application No. 14/511,692, filed on Oct. 10, 2014, now abandoned, which is a
(Continued)

(51) Int. Cl.
*A61B 5/026* (2006.01)
*A61B 5/0205* (2006.01)
(Continued)

(52) U.S. Cl.
CPC .......... *A61B 5/6803* (2013.01); *A61B 5/0059* (2013.01); *A61B 5/026* (2013.01);
(Continued)

(58) Field of Classification Search
CPC .. A61B 5/02438; A61B 5/6803; A61B 5/6817
See application file for complete search history.

(56) References Cited

U.S. PATENT DOCUMENTS 3,595,219 A 7/1971 Friedlander et al.
4,240,882 A 12/1980 Ang et al.
(Continued)

FOREIGN PATENT DOCUMENTS

CN 101212927 A 7/2008
CN 201438747 U 4/2010
(Continued)

OTHER PUBLICATIONS

Fitrainer "The Only Trainer You Need"; http://itami.com; Downloaded Feb. 26, 2010; © 2008 FiTriainer™; 2 pages.
(Continued)

*Primary Examiner* — Mallika D Fairchild
*Assistant Examiner* — Nathan A Baldwin
(74) *Attorney, Agent, or Firm* — Myers Bigel P.A.

(57) ABSTRACT

A headset includes a housing defining an audio cavity, a speaker located within the audio cavity, and first and second sensor modules within the housing in spaced-apart, angled relationship to each other. The housing includes an aperture through which sound from the speaker can pass, and the first and second sensor modules are on opposing sides of a direction from the speaker to the aperture. The first sensor module is configured to direct electromagnetic radiation at a first target region of an ear of a person wearing the headset and to detect a first energy response signal therefrom that is associated with one or more physiological metrics of the subject, and the second sensor module is configured to direct electromagnetic radiation at a second target region of the ear and to detect a second energy response signal therefrom that is associated with the one or more physiological metrics.

23 Claims, 28 Drawing Sheets

Related U.S. Application Data continuation of application No. 13/358,102, filed on Jan. 25, 2012, now Pat. No. 8,888,701.

(60) Provisional application No. 61/436,664, filed on Jan. 27, 2011.

(51) Int. Cl.

| | | |
|---|---|---|
| *A61B 5/00* | (2006.01) | |
| *A61B 5/1455* | (2006.01) | |
| *G16H 40/63* | (2018.01) | |
| *G16Z 99/00* | (2019.01) | |
| *A61B 5/021* | (2006.01) | |
| *A61B 5/024* | (2006.01) | |
| *A61B 5/08* | (2006.01) | |
| *A61B 6/00* | (2006.01) | |
| *A61B 8/02* | (2006.01) | |
| *A61B 8/04* | (2006.01) | |
| *A61B 8/06* | (2006.01) | |
| *A61B 5/145* | (2006.01) | |

(52) U.S. Cl.
CPC .......... *A61B 5/14551* (2013.01); *A61B 5/681* (2013.01); *A61B 5/6817* (2013.01); *A61B 5/721* (2013.01); *A61B 5/7203* (2013.01); *A61B 5/7207* (2013.01); *G16H 40/63* (2018.01); *G16Z 99/00* (2019.02); *A61B 5/021* (2013.01); *A61B 5/024* (2013.01); *A61B 5/0205* (2013.01); *A61B 5/02438* (2013.01); *A61B 5/0816* (2013.01); *A61B 5/1455* (2013.01); *A61B 5/14546* (2013.01); *A61B 6/507* (2013.01); *A61B 8/02* (2013.01); *A61B 8/04* (2013.01); *A61B 8/06* (2013.01); *A61B 2560/0247* (2013.01)

(56) References Cited

U.S. PATENT DOCUMENTS

| | | |
|---|---|---|
| 4,331,154 A | 5/1982 | Broadwater et al. |
| 4,438,772 A | 3/1984 | Slavin |
| 4,491,760 A | 1/1985 | Linvill |
| 4,521,499 A | 6/1985 | Switzer |
| 4,541,905 A | 9/1985 | Kuwana et al. |
| 4,592,807 A | 6/1986 | Switzer |
| 4,655,225 A | 4/1987 | Dahne et al. |
| 4,773,422 A | 9/1988 | Isaacson et al. |
| 4,830,014 A | 5/1989 | Goodman et al. |
| 4,882,492 A | 11/1989 | Schlager |
| 4,896,676 A | 1/1990 | Sasaki |
| 4,928,704 A | 5/1990 | Hardt |
| 4,952,890 A | 8/1990 | Swanson |
| 4,952,928 A | 8/1990 | Carroll et al. |
| 4,957,109 A | 9/1990 | Groeger et al. |
| 5,002,060 A | 3/1991 | Nedivi |
| 5,022,970 A | 6/1991 | Cook et al. |
| 5,025,791 A | 6/1991 | Niwa |
| 5,079,421 A | 1/1992 | Knudson et al. |
| 5,080,098 A | 1/1992 | Willett et al. |
| 5,086,229 A | 2/1992 | Rosenthal et al. |
| 5,139,025 A | 8/1992 | Lewis et al. |
| 5,143,078 A | 9/1992 | Mather et al. |
| 5,226,417 A | 7/1993 | Swedlow et al. |
| 5,237,994 A | 8/1993 | Goldberger |
| 5,273,036 A | 12/1993 | Kronberg et al. |
| 5,299,570 A | 4/1994 | Hatschek |
| 5,348,002 A | 9/1994 | Caro |
| 5,377,100 A | 12/1994 | Pope et al. |
| 5,448,082 A | 9/1995 | Kim |
| 5,482,036 A | 1/1996 | Diab et al. |
| 5,492,129 A | 2/1996 | Greenberger |
| 5,494,043 A | 2/1996 | O'Sullivan et al. |
| 5,499,301 A | 3/1996 | Sudo et al. |
| 5,581,648 A | 12/1996 | Sahagen |
| 5,596,987 A | 1/1997 | Chance |
| 5,662,117 A | 9/1997 | Bittman |
| 5,673,692 A | 10/1997 | Schulze et al. |
| 5,697,374 A | 12/1997 | Odagiri et al. |
| 5,711,308 A | 1/1998 | Singer |
| 5,725,480 A | 3/1998 | Oosta et al. |
| 5,743,260 A | 4/1998 | Chung et al. |
| 5,779,631 A | 7/1998 | Chance |
| 5,797,841 A | 8/1998 | Delonzor et al. |
| 5,807,114 A | 9/1998 | Hodges et al. |
| 5,807,267 A | 9/1998 | Bryars et al. |
| 5,817,008 A | 10/1998 | Rafert et al. |
| 5,846,190 A | 12/1998 | Woehrle |
| 5,853,005 A | 12/1998 | Scanlon |
| 5,904,654 A | 5/1999 | Wohltmann et al. |
| 5,938,593 A | 8/1999 | Ouellette |
| 5,954,644 A | 9/1999 | Dettling et al. |
| 5,964,701 A | 10/1999 | Asada et al. |
| 5,971,931 A | 10/1999 | Raff |
| 5,974,338 A | 10/1999 | Asano et al. |
| 5,995,858 A | 11/1999 | Kinast |
| 6,004,274 A | 12/1999 | Aceti et al. |
| 6,013,007 A | 1/2000 | Root et al. |
| 6,022,748 A | 2/2000 | Charych et al. |
| 6,023,541 A | 2/2000 | Merchant et al. |
| 6,030,342 A | 2/2000 | Amano et al. |
| 6,045,511 A | 4/2000 | Ott et al. |
| 6,067,006 A | 5/2000 | O'Brien |
| 6,070,093 A | 5/2000 | Oosta et al. |
| 6,078,829 A | 6/2000 | Uchida et al. |
| 6,080,110 A * | 6/2000 | Thorgersen ............ A61B 5/222 600/322 |
| 6,081,742 A | 6/2000 | Amano et al. |
| 6,095,983 A | 8/2000 | Amano et al. |
| 6,155,983 A | 12/2000 | Kosuda |
| 6,168,567 B1 | 1/2001 | Pickering et al. |
| 6,186,145 B1 | 2/2001 | Brown |
| 6,198,394 B1 | 3/2001 | Jacobsen et al. |
| 6,198,951 B1 | 3/2001 | Kosuda et al. |
| 6,205,354 B1 | 3/2001 | Gellermann et al. |
| 6,231,519 B1 | 5/2001 | Blants et al. |
| 6,241,684 B1 | 6/2001 | Amano et al. |
| 6,267,721 B1 | 7/2001 | Welles |
| 6,283,915 B1 | 9/2001 | Nolan et al. |
| 6,285,816 B1 | 9/2001 | Anderson et al. |
| 6,289,230 B1 | 9/2001 | Chaiken et al. |
| 6,298,314 B1 | 10/2001 | Blackadar et al. |
| 6,332,868 B1 | 12/2001 | Sato et al. |
| 6,358,216 B1 | 3/2002 | Kraus et al. |
| 6,361,660 B1 | 3/2002 | Goldstein |
| 6,371,925 B1 | 4/2002 | Imai et al. |
| 6,374,129 B1 | 4/2002 | Chin et al. |
| 6,397,092 B1 | 5/2002 | Norris et al. |
| 6,415,167 B1 | 7/2002 | Blank et al. |
| 6,443,890 B1 | 9/2002 | Schulze et al. |
| 6,444,474 B1 | 9/2002 | Thomas et al. |
| 6,454,718 B1 | 9/2002 | Clift |
| 6,458,080 B1 | 10/2002 | Brown et al. |
| 6,470,893 B1 | 10/2002 | Boesen |
| 6,513,532 B2 | 2/2003 | Mault et al. |
| 6,514,278 B1 | 2/2003 | Hibst et al. |
| 6,527,711 B1 | 3/2003 | Stivoric et al. |
| 6,527,712 B1 | 3/2003 | Brown et al. |
| 6,529,754 B2 | 3/2003 | Kondo |
| 6,534,012 B1 | 3/2003 | Hazen et al. |
| 6,556,852 B1 | 4/2003 | Schulze et al. |
| 6,569,094 B2 | 5/2003 | Suzuki et al. |
| 6,571,117 B1 | 5/2003 | Marbach |
| 6,605,038 B1 | 8/2003 | Teller et al. |
| 6,608,562 B1 | 8/2003 | Kimura et al. |
| 6,616,613 B1 | 9/2003 | Goodman |
| 6,631,196 B1 | 10/2003 | Taenzer et al. |
| 6,647,378 B2 | 11/2003 | Kindo |
| 6,656,116 B2 | 12/2003 | Kim et al. |
| 6,694,180 B1 | 2/2004 | Boesen |
| 6,702,752 B2 | 3/2004 | Dekker |
| 6,725,072 B2 | 4/2004 | Steuer et al. |
| 6,745,061 B1 | 6/2004 | Hicks et al. |

(56) References Cited

U.S. PATENT DOCUMENTS

| | | |
|---|---|---|
| 6,748,254 B2 | 6/2004 | O'Neil et al. |
| 6,760,610 B2 | 7/2004 | Tschupp et al. |
| 6,783,501 B2 | 8/2004 | Takahashi et al. |
| 6,808,473 B2 | 10/2004 | Hisano et al. |
| 6,859,658 B1 | 2/2005 | Krug |
| 6,893,396 B2 | 5/2005 | Schulze et al. |
| 6,941,239 B2 | 9/2005 | Unuma et al. |
| 6,953,435 B2 | 10/2005 | Kondo et al. |
| 6,954,644 B2 | 10/2005 | Johansson et al. |
| 6,996,427 B2 | 2/2006 | Ali et al. |
| 6,997,879 B1 | 2/2006 | Turcott |
| 7,018,338 B2 | 3/2006 | Vetter et al. |
| 7,024,369 B1 | 4/2006 | Brown et al. |
| 7,030,359 B2 | 4/2006 | Römhild |
| 7,034,694 B2 | 4/2006 | Yamaguchi et al. |
| 7,039,454 B1 | 5/2006 | Kaga et al. |
| 7,041,062 B2 | 5/2006 | Friedrichs et al. |
| 7,043,287 B1 | 5/2006 | Khalil et al. |
| 7,054,674 B2 | 5/2006 | Cane et al. |
| 7,088,234 B2 | 8/2006 | Naito et al. |
| 7,107,088 B2 | 9/2006 | Aceti |
| 7,113,815 B2 | 9/2006 | O'Neil et al. |
| 7,117,032 B2 | 10/2006 | Childre et al. |
| 7,163,512 B1 | 1/2007 | Childre et al. |
| 7,175,601 B2 | 2/2007 | Verjus et al. |
| 7,190,986 B1 | 3/2007 | Hannula et al. |
| 7,209,775 B2 | 4/2007 | Bae et al. |
| 7,217,224 B2 | 5/2007 | Thomas |
| 7,252,639 B2 | 8/2007 | Kimura et al. |
| 7,263,396 B2 | 8/2007 | Chen et al. |
| 7,289,837 B2 | 10/2007 | Mannheimer et al. |
| 7,336,982 B2 | 2/2008 | Yoo et al. |
| 7,341,559 B2 | 3/2008 | Schultz et al. |
| 7,376,451 B2 | 5/2008 | Mahony et al. |
| 7,378,954 B2 | 5/2008 | Wendt |
| 7,470,234 B1 | 12/2008 | Elhag et al. |
| 7,483,730 B2 | 1/2009 | Diab et al. |
| 7,486,988 B2 | 2/2009 | Goodall et al. |
| 7,507,207 B2 | 3/2009 | Sakai et al. |
| 7,519,327 B2 | 4/2009 | White |
| 7,526,327 B2 | 4/2009 | Blondeau et al. |
| 7,583,994 B2 | 9/2009 | Scholz |
| 7,620,450 B2 | 11/2009 | Kim et al. |
| 7,625,285 B2 | 12/2009 | Breving |
| 7,652,569 B2 | 1/2010 | Kiff et al. |
| 7,689,437 B1 | 3/2010 | Teller et al. |
| 7,695,440 B2 | 4/2010 | Kondo et al. |
| 7,725,147 B2 | 5/2010 | Li et al. |
| 7,756,559 B2 | 7/2010 | Abreu |
| 7,843,325 B2 | 11/2010 | Otto |
| 7,894,869 B2 | 2/2011 | Hoarau |
| 7,914,468 B2 | 3/2011 | Shalon et al. |
| 7,991,448 B2 | 8/2011 | Edgar et al. |
| 7,998,079 B2 | 8/2011 | Nagai et al. |
| 8,050,728 B2 | 11/2011 | Al-Ali et al. |
| 8,055,319 B2 | 11/2011 | Oh et al. |
| 8,055,330 B2 | 11/2011 | Egozi |
| 8,059,924 B1 | 11/2011 | Letant et al. |
| 8,130,105 B2 | 3/2012 | Al-Ali et al. |
| 8,137,270 B2 | 3/2012 | Keenan et al. |
| 8,172,459 B2 | 5/2012 | Abreu |
| 8,175,670 B2 | 5/2012 | Baker, Jr. et al. |
| 8,204,730 B2 | 6/2012 | Liu et al. |
| 8,233,955 B2 | 7/2012 | Al-Ali et al. |
| 8,251,903 B2 | 8/2012 | LeBoeuf et al. |
| 8,255,027 B2 | 8/2012 | Al-Ali et al. |
| 8,255,029 B2 | 8/2012 | Addison et al. |
| 8,303,512 B2 | 11/2012 | Kosuda et al. |
| 8,328,420 B2 | 12/2012 | Abreu |
| 8,416,959 B2 | 4/2013 | Lott et al. |
| 8,491,492 B2 | 7/2013 | Shinar et al. |
| 8,504,679 B2 | 8/2013 | Spire et al. |
| 8,506,524 B2 | 8/2013 | Graskov et al. |
| 8,512,242 B2 | 8/2013 | LeBoeuf et al. |
| 8,679,008 B2 | 3/2014 | Hughes et al. |
| 8,730,048 B2 | 5/2014 | Shen et al. |
| 9,005,129 B2 | 4/2015 | Venkatraman et al. |
| 2001/0015123 A1 | 8/2001 | Nishitani et al. |
| 2001/0044588 A1 | 11/2001 | Mault |
| 2001/0049471 A1 | 12/2001 | Suzuki et al. |
| 2002/0026108 A1 | 2/2002 | Colvin |
| 2002/0035340 A1 | 3/2002 | Fraden et al. |
| 2002/0143242 A1 | 10/2002 | Nemirovski |
| 2002/0156386 A1 | 10/2002 | Dardik et al. |
| 2002/0156654 A1 | 10/2002 | Roe et al. |
| 2002/0186137 A1 | 12/2002 | Skardon |
| 2002/0188210 A1 | 12/2002 | Aizawa |
| 2002/0194002 A1 | 12/2002 | Petrushin |
| 2002/0198443 A1 | 12/2002 | Ting |
| 2003/0002705 A1 | 1/2003 | Boesen |
| 2003/0007631 A1 | 1/2003 | Bolognesi et al. |
| 2003/0045785 A1 | 3/2003 | Diab et al. |
| 2003/0050563 A1 | 3/2003 | Suribhotla et al. |
| 2003/0064712 A1 | 4/2003 | Gaston et al. |
| 2003/0065257 A1 | 4/2003 | Mault et al. |
| 2003/0065269 A1 | 4/2003 | Vetter et al. |
| 2003/0083583 A1 | 5/2003 | Kovtun et al. |
| 2003/0109030 A1 | 6/2003 | Uchida et al. |
| 2003/0109791 A1 | 6/2003 | Kondo et al. |
| 2003/0181795 A1 | 9/2003 | Suzuki et al. |
| 2003/0181798 A1 | 9/2003 | Al-Ali |
| 2003/0212336 A1 | 11/2003 | Lee et al. |
| 2003/0220584 A1 | 11/2003 | Honeyager et al. |
| 2003/0222268 A1 | 12/2003 | Yocom et al. |
| 2003/0233051 A1 | 12/2003 | Verjus et al. |
| 2004/0004547 A1 | 1/2004 | Appelt et al. |
| 2004/0022700 A1 | 2/2004 | Kim et al. |
| 2004/0030581 A1 | 2/2004 | Leven |
| 2004/0034289 A1 | 2/2004 | Teller et al. |
| 2004/0034293 A1 | 2/2004 | Kimball |
| 2004/0039254 A1 | 2/2004 | Stivoric et al. |
| 2004/0054291 A1 | 3/2004 | Schulz et al. |
| 2004/0075677 A1 | 4/2004 | Loyall et al. |
| 2004/0077934 A1 | 4/2004 | Massad |
| 2004/0082842 A1 | 4/2004 | Lumba et al. |
| 2004/0103146 A1 | 5/2004 | Park |
| 2004/0117204 A1 | 6/2004 | Mazar et al. |
| 2004/0120844 A1 | 6/2004 | Tribelsky et al. |
| 2004/0122294 A1 | 6/2004 | Hatlestad et al. |
| 2004/0122702 A1 | 6/2004 | Sabol et al. |
| 2004/0133081 A1 | 7/2004 | Teller |
| 2004/0133123 A1 | 7/2004 | Leonhardt et al. |
| 2004/0135571 A1 | 7/2004 | Uutela et al. |
| 2004/0138578 A1 | 7/2004 | Pineda et al. |
| 2004/0186387 A1 | 9/2004 | Kosuda et al. |
| 2004/0186390 A1 | 9/2004 | Ross et al. |
| 2004/0219056 A1 | 11/2004 | Tribelsky et al. |
| 2004/0220488 A1 | 11/2004 | Vyshedskiy et al. |
| 2004/0225207 A1 | 11/2004 | Bae et al. |
| 2004/0228494 A1 | 11/2004 | Smith |
| 2004/0242976 A1 | 12/2004 | Abreu |
| 2004/0254501 A1 | 12/2004 | Mault |
| 2005/0004458 A1 | 1/2005 | Kanayama et al. |
| 2005/0007582 A1 | 1/2005 | Villers et al. |
| 2005/0021519 A1 | 1/2005 | Ghouri |
| 2005/0027216 A1 | 2/2005 | Guillemaud et al. |
| 2005/0030540 A1 | 2/2005 | Thornton |
| 2005/0033200 A1 | 2/2005 | Soehren et al. |
| 2005/0036212 A1 | 2/2005 | Saito |
| 2005/0038349 A1 | 2/2005 | Choi et al. |
| 2005/0043600 A1 | 2/2005 | Diab et al. |
| 2005/0043630 A1 | 2/2005 | Honeyager et al. |
| 2005/0058456 A1 | 3/2005 | Yoo |
| 2005/0059870 A1 | 3/2005 | Aceti |
| 2005/0070809 A1 | 3/2005 | Acres |
| 2005/0084666 A1 | 4/2005 | Pong et al. |
| 2005/0101845 A1 | 5/2005 | Nihtila |
| 2005/0101872 A1 | 5/2005 | Sattler et al. |
| 2005/0113167 A1 | 5/2005 | Buchner et al. |
| 2005/0113656 A1* | 5/2005 | Chance ............ A61B 5/14553 600/323 |
| 2005/0113703 A1 | 5/2005 | Farringdon et al. |
| 2005/0116820 A1 | 6/2005 | Goldreich |
| 2005/0119833 A1 | 6/2005 | Nanikashvili |

(56) References Cited

U.S. PATENT DOCUMENTS

| | | |
|---|---|---|
| 2005/0148883 A1 | 7/2005 | Boesen |
| 2005/0154264 A1 | 7/2005 | Lecompte et al. |
| 2005/0177034 A1 | 8/2005 | Beaumont |
| 2005/0187448 A1* | 8/2005 | Petersen ............... A61B 5/725 600/323 |
| 2005/0187453 A1 | 8/2005 | Petersen et al. |
| 2005/0192515 A1 | 9/2005 | Givens et al. |
| 2005/0196009 A1 | 9/2005 | Boesen |
| 2005/0203349 A1 | 9/2005 | Nanikashvili |
| 2005/0203357 A1 | 9/2005 | Debreczeny et al. |
| 2005/0209516 A1 | 9/2005 | Fraden |
| 2005/0212405 A1 | 9/2005 | Negley |
| 2005/0222487 A1 | 10/2005 | Miller et al. |
| 2005/0222903 A1 | 10/2005 | Buchheit et al. |
| 2005/0228244 A1 | 10/2005 | Banet |
| 2005/0228299 A1 | 10/2005 | Banet |
| 2005/0228463 A1 | 10/2005 | Mac et al. |
| 2005/0240087 A1 | 10/2005 | Keenan et al. |
| 2005/0245839 A1 | 11/2005 | Stivoric et al. |
| 2005/0258816 A1 | 11/2005 | Zen et al. |
| 2005/0259811 A1 | 11/2005 | Kimm et al. |
| 2006/0009685 A1 | 1/2006 | Finarov et al. |
| 2006/0012567 A1 | 1/2006 | Sicklinger |
| 2006/0063993 A1 | 3/2006 | Yu et al. |
| 2006/0064037 A1 | 3/2006 | Shalon et al. |
| 2006/0084878 A1 | 4/2006 | Banet et al. |
| 2006/0084879 A1 | 4/2006 | Nazarian et al. |
| 2006/0122520 A1 | 6/2006 | Banet et al. |
| 2006/0123885 A1 | 6/2006 | Yates et al. |
| 2006/0140425 A1 | 6/2006 | Berg et al. |
| 2006/0142665 A1 | 6/2006 | Garay et al. |
| 2006/0202816 A1 | 9/2006 | Crump et al. |
| 2006/0205083 A1 | 9/2006 | Zhao |
| 2006/0210058 A1 | 9/2006 | Kock et al. |
| 2006/0211922 A1 | 9/2006 | Al-Ali et al. |
| 2006/0211924 A1 | 9/2006 | Dalke et al. |
| 2006/0217598 A1 | 9/2006 | Miyajima et al. |
| 2006/0224059 A1 | 10/2006 | Swedlow et al. |
| 2006/0240558 A1 | 10/2006 | Zhao |
| 2006/0246342 A1 | 11/2006 | MacPhee |
| 2006/0251277 A1 | 11/2006 | Cho |
| 2006/0251334 A1 | 11/2006 | Oba et al. |
| 2006/0252999 A1 | 11/2006 | Devaul et al. |
| 2006/0264730 A1 | 11/2006 | Stivoric et al. |
| 2006/0292533 A1 | 12/2006 | Selod |
| 2006/0293921 A1 | 12/2006 | McCarthy et al. |
| 2007/0004449 A1 | 1/2007 | Sham |
| 2007/0004969 A1 | 1/2007 | Kong et al. |
| 2007/0015992 A1 | 1/2007 | Filkins et al. |
| 2007/0021206 A1 | 1/2007 | Sunnen |
| 2007/0027367 A1 | 2/2007 | Oliver et al. |
| 2007/0027399 A1 | 2/2007 | Chou |
| 2007/0036383 A1 | 2/2007 | Romero |
| 2007/0050215 A1 | 3/2007 | Kil et al. |
| 2007/0060800 A1 | 3/2007 | Drinan et al. |
| 2007/0060819 A1 | 3/2007 | Altschuler et al. |
| 2007/0063850 A1 | 3/2007 | Devaul et al. |
| 2007/0082789 A1 | 4/2007 | Nissila et al. |
| 2007/0083092 A1 | 4/2007 | Rippo et al. |
| 2007/0083095 A1 | 4/2007 | Rippo et al. |
| 2007/0088221 A1 | 4/2007 | Stahmann |
| 2007/0093702 A1 | 4/2007 | Yu et al. |
| 2007/0106167 A1 | 5/2007 | Kinast |
| 2007/0112273 A1 | 5/2007 | Rogers |
| 2007/0112598 A1 | 5/2007 | Heckerman et al. |
| 2007/0116314 A1 | 5/2007 | Grilliot et al. |
| 2007/0118054 A1 | 5/2007 | Oliver et al. |
| 2007/0123763 A1 | 5/2007 | Al-Ali et al. |
| 2007/0135717 A1 | 6/2007 | Uenishi et al. |
| 2007/0165872 A1 | 7/2007 | Bridger et al. |
| 2007/0167850 A1 | 7/2007 | Russell et al. |
| 2007/0191718 A1 | 8/2007 | Nakamura |
| 2007/0197878 A1 | 8/2007 | Shklarski |
| 2007/0197881 A1 | 8/2007 | Wolf et al. |
| 2007/0213020 A1 | 9/2007 | Novac |
| 2007/0230714 A1 | 10/2007 | Armstrong |
| 2007/0233403 A1 | 10/2007 | Alwan et al. |
| 2007/0265097 A1 | 11/2007 | Havukainen |
| 2007/0270667 A1 | 11/2007 | Coppi et al. |
| 2007/0270671 A1 | 11/2007 | Gal |
| 2007/0293781 A1 | 12/2007 | Sims et al. |
| 2007/0299330 A1 | 12/2007 | Couronne et al. |
| 2008/0001735 A1 | 1/2008 | Tran |
| 2008/0004536 A1 | 1/2008 | Baxi et al. |
| 2008/0015424 A1 | 1/2008 | Bernreuter |
| 2008/0039731 A1 | 2/2008 | McCombie et al. |
| 2008/0051670 A1 | 2/2008 | Banet et al. |
| 2008/0076972 A1 | 3/2008 | Dorogusker et al. |
| 2008/0081963 A1 | 4/2008 | Naghavi et al. |
| 2008/0081972 A1 | 4/2008 | Debreczeny |
| 2008/0086533 A1 | 4/2008 | Neuhauser et al. |
| 2008/0096726 A1 | 4/2008 | Riley et al. |
| 2008/0114220 A1 | 5/2008 | Banet et al. |
| 2008/0132798 A1 | 6/2008 | Hong et al. |
| 2008/0133699 A1 | 6/2008 | Craw et al. |
| 2008/0141301 A1 | 6/2008 | Azzaro et al. |
| 2008/0146890 A1 | 6/2008 | LeBoeuf et al. |
| 2008/0146892 A1 | 6/2008 | LeBoeuf et al. |
| 2008/0154098 A1 | 6/2008 | Morris et al. |
| 2008/0154105 A1 | 6/2008 | Lemay |
| 2008/0165017 A1 | 7/2008 | Schwartz |
| 2008/0170600 A1 | 7/2008 | Sattler et al. |
| 2008/0171945 A1 | 7/2008 | Dotter |
| 2008/0177162 A1 | 7/2008 | Bae et al. |
| 2008/0200774 A1 | 8/2008 | Luo |
| 2008/0203144 A1 | 8/2008 | Kim |
| 2008/0208020 A1 | 8/2008 | Cinbis et al. |
| 2008/0221461 A1 | 9/2008 | Zhou et al. |
| 2008/0249594 A1 | 10/2008 | Dietrich |
| 2008/0287752 A1* | 11/2008 | Stroetz ............... A61B 5/14552 600/301 |
| 2009/0005662 A1 | 1/2009 | Petersen et al. |
| 2009/0006457 A1 | 1/2009 | Stivoric et al. |
| 2009/0010461 A1 | 1/2009 | Klinghult et al. |
| 2009/0010556 A1 | 1/2009 | Uchibayashi et al. |
| 2009/0030350 A1 | 1/2009 | Yang et al. |
| 2009/0054751 A1 | 2/2009 | Babashan et al. |
| 2009/0054752 A1 | 2/2009 | Jonnalagadda et al. |
| 2009/0069645 A1 | 3/2009 | Nielsen et al. |
| 2009/0082994 A1 | 3/2009 | Schuler et al. |
| 2009/0088611 A1 | 4/2009 | Buschmann |
| 2009/0093687 A1 | 4/2009 | Telfort et al. |
| 2009/0105548 A1 | 4/2009 | Bart |
| 2009/0105556 A1 | 4/2009 | Fricke et al. |
| 2009/0112071 A1 | 4/2009 | LeBoeuf et al. |
| 2009/0131761 A1 | 5/2009 | Moroney III et al. |
| 2009/0131764 A1 | 5/2009 | Lee et al. |
| 2009/0171177 A1 | 7/2009 | Hannula et al. |
| 2009/0175456 A1 | 7/2009 | Johnson |
| 2009/0177097 A1* | 7/2009 | Ma .................. A61B 5/14551 600/500 |
| 2009/0202098 A1* | 8/2009 | Chan ................ H04R 1/1066 381/380 |
| 2009/0214060 A1 | 8/2009 | Chuang et al. |
| 2009/0221888 A1 | 9/2009 | Wijesiriwardana |
| 2009/0227853 A1 | 9/2009 | Wijesiriwardana |
| 2009/0240125 A1 | 9/2009 | Such et al. |
| 2009/0253992 A1 | 10/2009 | Van Der Loo |
| 2009/0253996 A1 | 10/2009 | Lee et al. |
| 2009/0264711 A1 | 10/2009 | Schuler et al. |
| 2009/0270698 A1 | 10/2009 | Shioi et al. |
| 2009/0281435 A1 | 11/2009 | Ahmed et al. |
| 2009/0287067 A1 | 11/2009 | Dorogusker et al. |
| 2009/0299215 A1 | 12/2009 | Zhang |
| 2010/0004517 A1 | 1/2010 | Bryenton et al. |
| 2010/0022861 A1 | 1/2010 | Cinbis et al. |
| 2010/0045663 A1 | 2/2010 | Chen et al. |
| 2010/0100013 A1 | 4/2010 | Hu et al. |
| 2010/0113948 A1 | 5/2010 | Yang et al. |
| 2010/0168531 A1 | 7/2010 | Shaltis et al. |
| 2010/0172522 A1 | 7/2010 | Mooring et al. |
| 2010/0179389 A1 | 7/2010 | Moroney et al. |
| 2010/0185105 A1 | 7/2010 | Baldinger |
| 2010/0217098 A1 | 8/2010 | LeBoeuf et al. |

(56) References Cited

U.S. PATENT DOCUMENTS

| | | |
|---|---|---|
| 2010/0217099 A1 | 8/2010 | LeBoeuf et al. |
| 2010/0217102 A1 | 8/2010 | LeBoeuf et al. |
| 2010/0217103 A1 | 8/2010 | Abdul-Hafiz et al. |
| 2010/0222655 A1 | 9/2010 | Starr et al. |
| 2010/0228315 A1 | 9/2010 | Nielsen |
| 2010/0234714 A1 | 9/2010 | Mercier et al. |
| 2010/0268056 A1 | 10/2010 | Picard et al. |
| 2010/0274100 A1 | 10/2010 | Behar et al. |
| 2010/0274109 A1 | 10/2010 | Hu et al. |
| 2010/0292589 A1 | 11/2010 | Goodman |
| 2010/0298653 A1 | 11/2010 | McCombie et al. |
| 2010/0317937 A1 | 12/2010 | Kuhn et al. |
| 2011/0004106 A1 | 1/2011 | Iwamiya et al. |
| 2011/0028810 A1 | 2/2011 | Van Slyke et al. |
| 2011/0028813 A1 | 2/2011 | Watson et al. |
| 2011/0081037 A1 | 4/2011 | Oh et al. |
| 2011/0105869 A1 | 5/2011 | Wilson et al. |
| 2011/0112382 A1 | 5/2011 | Li et al. |
| 2011/0130638 A1 | 6/2011 | Raridan, Jr. |
| 2011/0142371 A1 | 6/2011 | King et al. |
| 2011/0288379 A1 | 11/2011 | Wu |
| 2012/0030547 A1 | 2/2012 | Raptis et al. |
| 2012/0095303 A1 | 4/2012 | He |
| 2012/0150052 A1 | 6/2012 | Buchheim et al. |
| 2012/0156933 A1 | 6/2012 | Kreger et al. |
| 2012/0179011 A1 | 7/2012 | Moon et al. |
| 2012/0190948 A1 | 7/2012 | Vetter et al. |
| 2012/0197093 A1 | 8/2012 | LeBoeuf et al. |
| 2012/0277548 A1 | 11/2012 | Burton |
| 2013/0053661 A1 | 2/2013 | Alberth et al. |
| 2013/0060098 A1 | 3/2013 | Thomsen et al. |
| 2013/0072765 A1 | 3/2013 | Kahn et al. |
| 2013/0131519 A1 | 5/2013 | LeBoeuf et al. |
| 2013/0245387 A1 | 9/2013 | Patel |
| 2013/0336495 A1 | 12/2013 | Burgett et al. |
| 2014/0051940 A1 | 2/2014 | Messerschmidt |
| 2014/0052567 A1 | 2/2014 | Bhardwaj et al. |
| 2014/0073486 A1 | 3/2014 | Ahmed et al. |
| 2014/0088433 A1 | 3/2014 | Shan |
| 2014/0100432 A1 | 4/2014 | Golda et al. |
| 2014/0127996 A1 | 5/2014 | Park et al. |
| 2014/0219467 A1 | 8/2014 | Kurtz |
| 2014/0236531 A1 | 8/2014 | Carter |
| 2014/0275852 A1 | 9/2014 | Hong et al. |
| 2014/0288436 A1 | 9/2014 | Venkatraman et al. |
| 2014/0323880 A1 | 10/2014 | Ahmed et al. |
| 2014/0378844 A1 | 12/2014 | Fei |
| 2015/0011898 A1 | 1/2015 | Romesburg |
| 2015/0018636 A1 | 1/2015 | Romesburg |
| 2015/0057967 A1 | 2/2015 | Albinali |
| 2015/0190085 A1 | 7/2015 | Nathan et al. |
| 2015/0250396 A1 | 9/2015 | Ahmed et al. |
| 2015/0265217 A1 | 9/2015 | Penders et al. |
| 2015/0289820 A1 | 10/2015 | Miller et al. |
| 2015/0342481 A1 | 12/2015 | Liu et al. |
| 2015/0366509 A1 | 12/2015 | Romesburg |
| 2016/0022220 A1 | 1/2016 | Lee et al. |
| 2016/0029964 A1 | 2/2016 | LeBoeuf et al. |
| 2016/0094899 A1 | 3/2016 | Aumer et al. |
| 2016/0287108 A1 | 10/2016 | Wei et al. |
| 2017/0034615 A1 | 2/2017 | Mankodi et al. |

FOREIGN PATENT DOCUMENTS

| | | |
|---|---|---|
| DE | 3910749 A1 | 10/1990 |
| EP | 1 297 784 A1 | 4/2003 |
| EP | 1 480 278 A2 | 11/2004 |
| EP | 2 077 091 A2 | 7/2009 |
| EP | 2 182 839 B1 | 10/2011 |
| GB | 2 408 209 A | 5/2005 |
| GB | 2 411 719 A | 9/2005 |
| JP | 7-241279 | 9/1995 |
| JP | 9-253062 | 9/1997 |
| JP | 9-299342 | 11/1997 |
| JP | 2000-116611 | 4/2000 |
| JP | 2001-025462 | 1/2001 |
| JP | 20030159221 | 6/2003 |
| JP | 2004-513750 A | 5/2004 |
| JP | 2004-283523 | 10/2004 |
| JP | 2005-040261 A | 2/2005 |
| JP | 2005-270544 A | 10/2005 |
| JP | 2007-044203 | 2/2007 |
| JP | 2007-185348 | 7/2007 |
| JP | 2008-136556 A | 6/2008 |
| JP | 2008-279061 A | 11/2008 |
| JP | 2009-153664 A | 7/2009 |
| JP | 2010-526646 | 8/2010 |
| JP | 2014-068733 A | 4/2014 |
| KR | 20-0204510 Y1 | 11/2000 |
| WO | WO 00/24064 | 4/2000 |
| WO | WO 2000/047108 A1 | 8/2000 |
| WO | WO 01/08552 A1 | 2/2001 |
| WO | WO 2002/017782 A2 | 3/2002 |
| WO | WO 2005/010568 A2 | 2/2005 |
| WO | WO 2005/020121 A1 | 3/2005 |
| WO | WO 2005/036212 A2 | 4/2005 |
| WO | WO 2005/110238 A1 | 11/2005 |
| WO | WO 2006/009830 A2 | 1/2006 |
| WO | WO 2006/067690 A2 | 6/2006 |
| WO | WO 2007/012931 A2 | 2/2007 |
| WO | WO 2007/023426 A2 | 3/2007 |
| WO | WO 2007/038432 A2 | 4/2007 |
| WO | WO 2007/053146 A1 | 5/2007 |
| WO | WO 2008/141306 A2 | 11/2008 |
| WO | WO 2011/127063 A1 | 10/2011 |
| WO | WO 2013/038296 A1 | 3/2013 |
| WO | WO 2014/092932 A1 | 6/2014 |
| WO | WO 2015/128226 A1 | 9/2015 |

OTHER PUBLICATIONS

Notification of Transmittal of the International Search Report and the Written Opinion of the Searching Authority dated Jul. 30, 2010 by the Korean Intellectual Property Office for corresponding international application No. PCT/US2010/021936.

Notification of Transmittal of the International Search Report and Written Opinion dated Aug. 26, 2010 by the Korean Intellectual Property Office for corresponding International Application No. PCT/US2010/021629.

International Search Report Corresponding to International Application No. PCT/US2012/022634; dated Aug. 22, 2012; 9 Pages.

"U.S. Army Fitness Training Handbook" by the Department of the Army, 2003, The Lyons Press, p. 17.

"Warfighter Physiological and Environmental Monitoring: A Study for the U.S. Army Research Institute in Environmental Medicine and the Soldier Systems Center", Massachusetts Institute of Technology Lincoln Laboratory, Final Report, Nov. 1, 2004, prepared for the U.S. Army under Air Force Contract F19628-00-C-0002; approved for public release.

Anpo et al. "Photocatalytic Reduction of $Co_2$ With $H_2$ O on Titanium Oxides Anchored within Micropores of Zeolites: Effects of the Structure of the Active Sites and the Addition of Pt" *J. Phys. Chem. B*, 101:2632-2636 (1997).

Bârsan et al. "Understanding the fundamental principles of metal oxide based gas sensors; the example of CO sensing with $SnO_2$ sensors in the presence of humidity" *Journal of Physics: Condensed Matter* 15:R813-R839 (2003).

Bott "Electrochemistry of Semiconductors" *Current Separations* 17(3):87-91 (1998).

Colligan, M. J. et al. in "The psychological effects of indoor air pollution", Bulletin of the New York Academy of Medicine, vol. 57, No. 10, Dec. 1981, p. 1014-1026.

De Paula Santos, U. et al, in "Effects of air pollution on blood pressure and heart rate variability: a panel study of vehicular traffic controllers in the city of Sao Paulo, Brazil", European Heart Journal (2005) 26, 193-200.

Ebert, T et al., "Influence of Hydration Status on Thermoregulation and Cycling Hill Climbing," Med. Sci. Sport Exerc. vol. 39, No. 2, pp. 323-329, 2007.

(56) References Cited

OTHER PUBLICATIONS

European Search Report corresponding to European Application No. 07862660.3 dated Apr. 25, 2012; 7 pages.
Falkner et al, "Cardiovascular response to mental stress in normal adolescents with hypertensive parents. Hemodynamics and mental stress in adolescents," *Hypertension* 1979,1:23-30.
Fleming et al., "A Comparison of Signal Processing Techniques for the Extraction of Breathing Rate from the Photopethysmorgram," World Academy of Science, Engineering and Technology, vol. 30, Oct. 2007, pp. 276-280.
Geladas et al., "Effect of cold air inhalation on core temperature in exercising subjects under stress," The American Physiological Society, pp. 2381-2387, 1988.
Gold, D.R. et al. in "Ambient Pollution and Heart Rate Variability", Circulation 2000, 101:1267-1273.
International Search Report corresponding to International Patent Application No. PCT/US2012/046446, dated Jan. 14, 2013, 3 pages.
International Search Report and Written Opinion of the International Searching Authority, corresponding to PCT/US2012/0948079, dated Oct. 9, 2012.
International Search Report and Written Opinion of the International Searching Authority, corresponding to PCT/US2007/025114, dated May 13, 2008.
Maomao et al., "Mobile Context-Aware Game for the Next Generation," $2^{nd}$ International Conference on Application and Development of Computer Games ADCOG 2003, p. 78-81.
Martins et al. "Zinc oxide as an ozone sensor" *Journal of Applied Physics* 96(3):1398-1408 (2004).
Maughan, R.J., "Impact of mild dehydration on wellness and on exercise performance," European Journal of Clinical Nutrition, 57, Suppl. 2, pp. S19-S23, 2003.
Maughan et al., "Exercise, Heat, Hydration and the Brain," Journal of the American College of Nutrition, vol. 26, No. 5, pp. 604S-612S, 2007.
Mostardi, R., et al., "The effect of increased body temperature due to exercise on the heart rate and the maximal aerobic power," Europ. J. Appl. Physiol, 33, pp. 237-245, 1974.
Nakajima et al., "Monitoring of heart and respiratory rates by photoplethyusmography using a digital filtering technique," Med. Eng. Phys., vol. 18, No. 5, Jul. 1996, pp. 365-372.
Notification of Transmittal of the International Search Report and the Written Opinion of the International Search Authority dated Sep. 16, 2010 by the Korean Intellectual Property Office for corresponding International Application No. PCT/US2010/024922.
Notification of Transmittal of the International Search Report and the Written Opinion of the International Search Authority dated Sep. 27, 2010 by the Korean Intellectual Property Office for corresponding International Application No. PCT/US2010/025216.
Notification of Transmittal of The International Search Report and the Written Opinion of the International Searching Authority, or the Declaration corresponding to International Application No. PCT/US2013/070271; dated Feb. 26, 2014; 13 pages.
Saladin et al. "Photosynthesis of $CH_4$ at a $TiO_2$ Surface from Gaseous $H_2O$ and $CO_2$" *J. Chem. Soc., Chem. Commun.* 533-534 (1995).
Shorten et al., "Acute effect of environmental temperature during exercise on subsequent energy intake in active men," Am. J Clin. Nutr. 90, pp. 1215-1221, 2009.
Skubal et al. "Detection and identification of gaseous organics using a $TiO_2$ sensor" *Journal of Photochemistry and Photobiology A: Chemistry* 148:103-108 (2002).
Skubal et al. "Monitoring the Electrical Response of Photoinduced Organic Oxideation on $TiO_2$ Surfaces" Manuscript submitted Oct. 2000 to SPIE Intl. Symposium on Environment & Industrial Sensing, Boston, MA, Nov. 5-8, 2000, sponsored by SPIE, 10 pp.
Thompson, M.W., "Cardiovascular drift and critical core temperature: factors limiting endurance performance in the heat?" J. Exerc. Sci. Fit, vol. 4, No. 1, pp. 15-24, 2006.

Zhang et al. "Development of Chemical Oxygen Demand On-Line Monitoring System Based on a Photoelectrochemical Degradation Principle" *Environ. Sci. Technol.*, 40(7):2363-2368 (2006).
Edmison et al., "E-Textile Based Automatic Activity Diary for Medical Annotation and Analysis," Proc. BSN 2006 Int. Workshop Wearable Implantable Body Sensor Netw. (2006), pp. 131-145, Apr. 3-5, 2006.
European Search Report, EP Application No. 13863449.8, dated Oct. 19, 2015, 3 pages.
European Search Report, EP Application No. 14743615.8, dated Oct. 12, 2015, 3 pages.
European Search Report, EP Application No. 14743839.4, dated Oct. 12, 2015, 3 pages.
Gibbs et al., "Reducing Motion Artifact in Wearable Bio-Sensors Using MEMS Accelerometers for Active Noise Cancellation," 2005 American Control Conference, Jun. 8-10, 2005, Portland, OR, USA, pp. 1581-1586.
International Preliminary Report on Patentability, PCT/US2014/012940, dated Jun. 17, 2015, 23 pages.
International Search Report and Written Opinion of the International Searching Authority, corresponding to International Patent Application No. PCT/US2014/012940, dated Oct. 16, 2014, 13 pages.
International Search Report corresponding to International Patent Application No. PCT/US2014/012909, dated May 13, 2014, 3 pages.
Notification Concerning Transmittal of International Preliminary Report on Patentability, PCT/US2014/012909, dated Jul. 28, 2015.
Notification of Transmittal of the International Search Report and the Written Opinion of the International Searching Authority, or the Declaration, PCT/US2015/014562, dated Oct. 28, 2015.
Notification of Transmittal of the International Search Report and the Written Opinion of the International Searching Authority, or the Declaration, PCT/US2015/042636, dated Oct. 29, 2015.
Notification of Transmittal of the International Search Report and the Written Opinion of the International Searching Authority, or the Declaration, PCT/US2015/042015, dated Oct. 29, 2015.
Notification of Transmittal of the International Search Report and the Written Opinion of the International Searching Authority, or the Declaration, PCT/US2015/042035, dated Oct. 29, 2015.
Wood et al., "Active Motion Artifact Reduction for Wearable Sensors Using Laguerre Expansion and Signal Separation," Proceedings of the 2005 IEEE Engineering in Medicine and Biology, $27^{th}$ Annual Conference, Shanghai, China, Sep. 1-4, 2005, pp. 3571-3574.
Notification of Transmittal of the International Search Report and the Written Opinion of the International Searching Authority, or the Declaration, PCT/US2015/046079, dated Dec. 29, 2015.
Communication pursuant to Article 94(3) EPC, European Patent Application No. 13863449.8, dated Nov. 5, 2015, 7 pages.
Communication pursuant to Article 94(3) EPC, European Patent Application No. 14743615.8, dated Dec. 23, 2015, 7 pages.
Communication pursuant to Article 94(3) EPC, European Patent Application No. 14743839.4, dated Dec. 23, 2015, 6 pages.
Communication pursuant to Article 94(3) EPC, European Patent Application No. 12820308.0, dated Feb. 3, 2016, 5 pages.
Notification of Transmittal of the International Search Report and Written Opinion of the International Search Authority dated May 26, 2016 by the Korean Intellectual Property Office for corresponding International Application No. PCT/US2016/019126.
Notification of Transmittal of the International Search Report and Written Opinion of the International Search Authority dated May 26, 2016 by the Korean Intellectual Property Office for corresponding International Application No. PCT/US2016/019132.
Asada, et al., "Mobile Monitoring with Wearable Photoplethysmographic Biosensors," IEEE Engineering in Medicine and Biology Magazine, May/Jun. 2003, pp. 28-40.
Bifulco et al., "Bluetooth Portable Device for Continuous ECG and Patient Motion Monitoring During Daily Life," Medicon 2007, IFMBE Proceedings 16, 2007, pp. 369-372.
Brodersen et al., "In-Ear Acquisition of Vital Signs Discloses New Chances for Preventive Continuous Cardiovascular Monitoring,"

(56) References Cited

OTHER PUBLICATIONS

4th International Workshop on Wearable and Implantable Body Sensor Networks (BSN 2007), vol. 13 of the series IFMBE Proceedings, pp. 189-194.
Celka et al., "Motion Resistant Earphone Located Infrared based Heart Rate Measurement Device," Proceedings of the Second IASTED International Conference on Biomedical Engineering, Feb. 16-18, 2004, Innsbruck, Austria, pp. 582-585.
Communication Pursuant to Article 94(3) EPC, EP 12 739 502.8, dated Jul. 19, 2016, 7 pages.
Communication Pursuant to Article 94(3) EPC, EP 14 743 615.8, dated Jul. 19, 2016, 7 pages.
Communication Pursuant to Article 94(3) EPC, EP 14 743 839.4, dated Jul. 20, 2016, 5 pages.
Comtois et al., "A Wearable Wireless Reflectance Pulse Oximeter for Remote Triage Applications," 2006 IEEE, pp. 53-54.
Comtois, Gary, W., "Implementation of Accelerometer-Based Adaptive Noise Cancellation in a Wireless Wearable Pulse Oximeter Platform for Remote Physiological Monitoring and Triage," Thesis, Worcester Polytechnic Institute, Aug. 31, 2007, 149 pages.
Duun et al., "A Novel Ring Shaped Photodiode for Reflectance Pulse Oximetry in Wireless Applications," IEEE Sensors 2007 Conference, pp. 596-599.
Geun et al., "Measurement Site and Applied Pressure Consideration in Wrist Photoplethysmography," The $23^{rd}$ International Technical Conference on Circuits/Systems, Computers and Communications, 2008, pp. 1129-1132.
Gibbs et al., "Active motion artifact cancellation for wearable health monitoring sensors using collocated MEMS accelerometers," Smart Structures and Materials, 2005: Sensors and Smart Structures Technologies for Civil, Mechanical, and Aerospace Systems, Proc. of SPIE, vol. 5765, pp. 811-819.
Haahr et al., "A Wearable "Electronic Patch" for Wireless Continuous Monitoring of Chronically Diseased Patients," Proceedings of the $5^{th}$ International Workshop on Wearable and Implantable Body Sensor Networks, in conjunction with the $5^{th}$ International Summer School and Symposium on Medical Devices and Biosensors, The Chinese University of Hong Kong, HKSAR, China, Jun. 1-3, 2008, pp. 66-70.
Jiang, Honghui, "Motion-Artifact Resistant Design of Photoplethysmograph Ring Sensor for Driver Monitoring," Thesis, Massachusetts Institute of Technology, Feb. 2004, 62 pages.
Kuzmina et al., "Compact multi-functional skin spectrometry set-up," Advanced Optical Materials, Technologies, and Devices, Proc. of SPIE, vol. 6596, 2007, p. 65960T-1 to 65960T-6.
Lee et al., "Respiratory Rate Detection Algorithms by Photoplethysmography Signal Processing," $30^{th}$ Annual International IEEE EMBS Conference, Vancouver, British Columbia, Canada, Aug. 20-24, 2008, pp. 1140-1143.
Lindberg et al., "Monitoring of respiratory and heart rates using a fibre-optic sensor," Med Biol Eng Comput, Sep. 1992, vol. 30, No. 5, pp. 533-537.
Luprano, Jean, "Sensors and Parameter Extraction by Wearable Systems: Present Situation and Future," pHealth 2008, May 21, 2008, 29 pages.
Lygouras et al., "Optical-Fiber Finger Photo-Plethysmograph Using Digital Techniques," IEEE Sensors Journal, vol. 2, No. 1, Feb. 2002, pp. 20-25.
Maguire et al., "The Design and Clinical Use of a Reflective Brachial Photoplethysmograph," Technical Report NUIM/SS/--/2002/04, Submitted Apr. 2002, Signals and Systems Research Group, National University of Ireland, Maynooth, Co. Kildare, Ireland, 13 pages.
Mendelson et al., "Measurement Site and Photodetector Size Considerations in Optimizing Power Consumption of a Wearable Reflectance Pulse Oximeter," Proceedings of the $25^{th}$ Annual International Conference of the IEEE EMBS, Cancun, Mexico, Sep. 17-21, 2003, pp. 3016-3019.
Mendelson et al., "Noninvasive Pulse Oximetry Utilizing Skin Reflectance Photoplethysmography," IEEE Transactions on Biomedical Engineering, vol. 35, No. 10, Oct. 1988, pp. 798-805.
Poh et al., "Motion Tolerant Magnetic Earring Sensor and Wireless Earpiece for Wearable Photoplethysmography," IEEE Transactions on Information Technology in Biomedicine, vol. 14, No. 3, May 2010, pp. 786-794.
Renevey et al., "Wrist-Located Pulse Detection Using IR Signals, Activity and Nonlinear Artifact Cancellation," IEEE EMBS, 2001, 4 pages.
Rhee et al., "Artifact-Resistant Power-Efficient Design of Finger-Ring Plethysmographic Sensors," IEEE Transactions on Biomedical Engineering, vol. 48, No. 7, Jul. 2001, pp. 795-805.
Shaltis, Phillip Andrew, Analysis and Validation of an Artifact Resistant Design for Oxygen Saturation Measurement Using Photo Plethysmographic Ring Sensors, Thesis, Massachusetts Institute of Technology, Jun. 2004, 103 pages.
Shin et al., "A Novel Headset with a Transmissive PPG Sensor for Heart Rate Measurement," ICBME 2008, Proceedings 23, 2009, pp. 519-522.
Spigulis et al, "Wearable wireless photoplethysmography sensors," Proc, of SPIE, vol. 6991, 2008, p. 69912O-1 to 69912O-7.
Takatani et al., "Optical Oximetry Sensors for Whole Blood and Tissue," IEEE Engineering in Medicine and Biology, Jun./Jul. 1994, pp. 347-357.
Vogel et al., "A System for Assessing Motion Artifacts in the Signal of a Micro-Optic In-Ear Vital Signs Sensor," $30^{th}$ Annual International IEEE EMBS Conference, Vancouver, British Columbia, Canada, Aug. 20-24, 2008.
Vogel et al., "In-Ear Heart Rate Monitoring Using a Micro-Optic Reflective Sensor," Proceedings of the $29^{th}$ Annual International Conference of the IEEE EMBS Cite Internationale, Lyon, France, Aug. 23-26, 2007, pp. 1375-1378.
Wang et al., "Multichannel Reflective PPG Earpiece Sensor With Passive Motion Cancellation," IEEE Transactions on Biomedical Circuits and Systems, vol. 1, No. 4, Dec. 2007, pp. 235-241.
Wang et al., "Reflective Photoplethysmograph Earpiece Sensor for Ubiquitous Heart Rate Monitoring," $4^{th}$ International Workshop on Wearable and Implantable Body Sensor Networks, 2007, vol. 13 of the series IFMBE Proceedings, pp. 179-183.
Wei et al. "A New Wristband Wearable Sensor Using Adaptive Reduction Filter to Reduce Motion Artifact," Proceedings of the $5^{th}$ International Conference on Information Technology and Application in Biomedicine, in conjunction with the $2^{nd}$ International Symposium & Summer School on Biomedical and Health Engineering, Shenzhen, China, May 30-31, 2008, pp. 278-281.
Wood, Levi Benjamin, "Motion Artifact Reduction for Wearable Photoplethysmogram Sensors Using Micro Accelerometers and Laguerre Series Adaptive Filters," Thesis, Massachusetts Institute of Technology, Jun. 2008, 74 pages.
Han et al., "Artifacts in wearable photoplethysmographs during daily life motions and their reduction with least mean square based active noise cancellation method," Computers in Biology and Medicine, 42, 2012, pp. 387-393.
Extended European Search Report, EP Application No. 16164775.5 dated Sep. 13, 2016, 7 pages.
Notification of Transmittal of the International Search Report and the Written Opinion of the International Searching Authority, or the Declaration, PCT/US2016/041842, dated Oct. 21, 2016, 5 pages.
Notification of Transmittal of International Preliminary Report on Patentability, PCT/US2015/041562, dated Oct. 20, 2016, 14 pages.
Notification of Transmittal of International Preliminary Report on Patentability, PCT/US2015/042636, dated Oct. 20, 2016, 7 pages.
Notification of Transmittal of International Preliminary Report on Patentability, PCT/US2015/042015, dated Oct. 20, 2016, 10 pages.
Notification of Transmittal of International Preliminary Report on Patentability, PCT/US2015/042035, dated Oct. 20, 2016, 8 pages.
Notification of Transmittal of International Preliminary Report on Patentability, PCT/US2015/046079, dated Oct. 20, 2016, 10 pages.
Gong, H. et al.; "Cardiovascular effects of ozone exposure in Human Volunteers"; Am. J. Resp. Grit. Care Med 1998; 158:538-546.

(56) References Cited

OTHER PUBLICATIONS

McDonnell, W. F. et al; "Pulmonary effects of ozone during exercise: dose-response characteristics"; Journal of Applied Physiology; 1983, vol. 54 No. 5. p. 1345-1352.

Watkinson, W. P.; "Cardiovascular and systemic Responses to Inhaled Pollutants in Rodents: Effects of Ozone and Particulate Matter"; Environmental Health Perspectives; vol. 109; Supplement 4, Aug. 2001; p. 539-546.v.

Van Marken W. D. et. al.; "Individual variation in the relation between body temperature and energy expenditure in response to elevated ambient temperature"; Physiology & Behavior 73 (2001)235-242.

Van Ooijen, A. M. J. et. al.; "Seasonal changes in metabolic and temperature responses to cold air in humans"; Physiology & Behavior 82 (2004) 545- 553.

Van Ooijen, A. M. J. et. al.; "Individual differences in body temperature and the relation to energy expenditure: the influence of mild cold"; Journal of Thermal Biology 26 (2001) 455-459.

Westerterp-Piantenga, M.S.; et al.; "Energy Metabolism in women during short exposure to the thermoneutral zone"; Physiology & Behavior 75 (2002) 227-235.

Extended European Search Report, European Application No. 16184560.7, dated Dec. 20, 2016, 9 pages.

Extended European Search Report, European Application No. 16183137.5, dated Jan. 12, 2017, 12 pages.

Communication pursuant to Article 94(3) EPC, European Application No. 12 739 502.8, dated Nov. 30, 2016, 6 pages.

Notification of Transmittal of the International Search Report and the Written Opinion of the International Searching Authority, or the Declaration, PCT/US2016/046273, dated Nov. 25, 2016, 24 pages.

Notification of Transmittal of the International Search Report and the Written Opinion of the International Searching Authority, or the Declaration, PCT/US2016/058098, dated Jan. 10, 2017, 13 pages.

Communication with Supplementary European Search Report, European Application No. 15830336.2, dated Jun. 7, 2017, 8 pp.

Communication with European Search Report, European Application No. 17176280.0, dated Oct. 2, 2017, 10 pp.

Comtois et al., "A Comparative Evaluation of Adaptive Noise Cancellation Algorithms for Minimizing Motion Artifacts in a Forehead-Mounted Wearable Pulse Oximeter", *Proceedings of the 29th Annual International Conference of the IEEE EMBS*, Lyon, France, August 23-26, 2007, pp. 1528-1531.

Han et al. "Development of a wearable health monitoring device with motion artifact reduced algorithm" *International Conference on Control, Automation and Systems 2007 (ICCAS 2007)*, Seoul, Korea, Oct. 17-20, 2007, pp. 1581-1584.

Lee et al., "A Mobile Care System With Alert Mechanism", *IEEE Transactions on Information Technology in Biomedicine*, vol. 11, No. 5, Sep. 2007, pp. 507-517.

Webster, J. G. Design of Pulse Oximeters. IOP Publishing Ltd., 1997, Cover page, pp. i-xvi, pp. 34-159.

\* cited by examiner

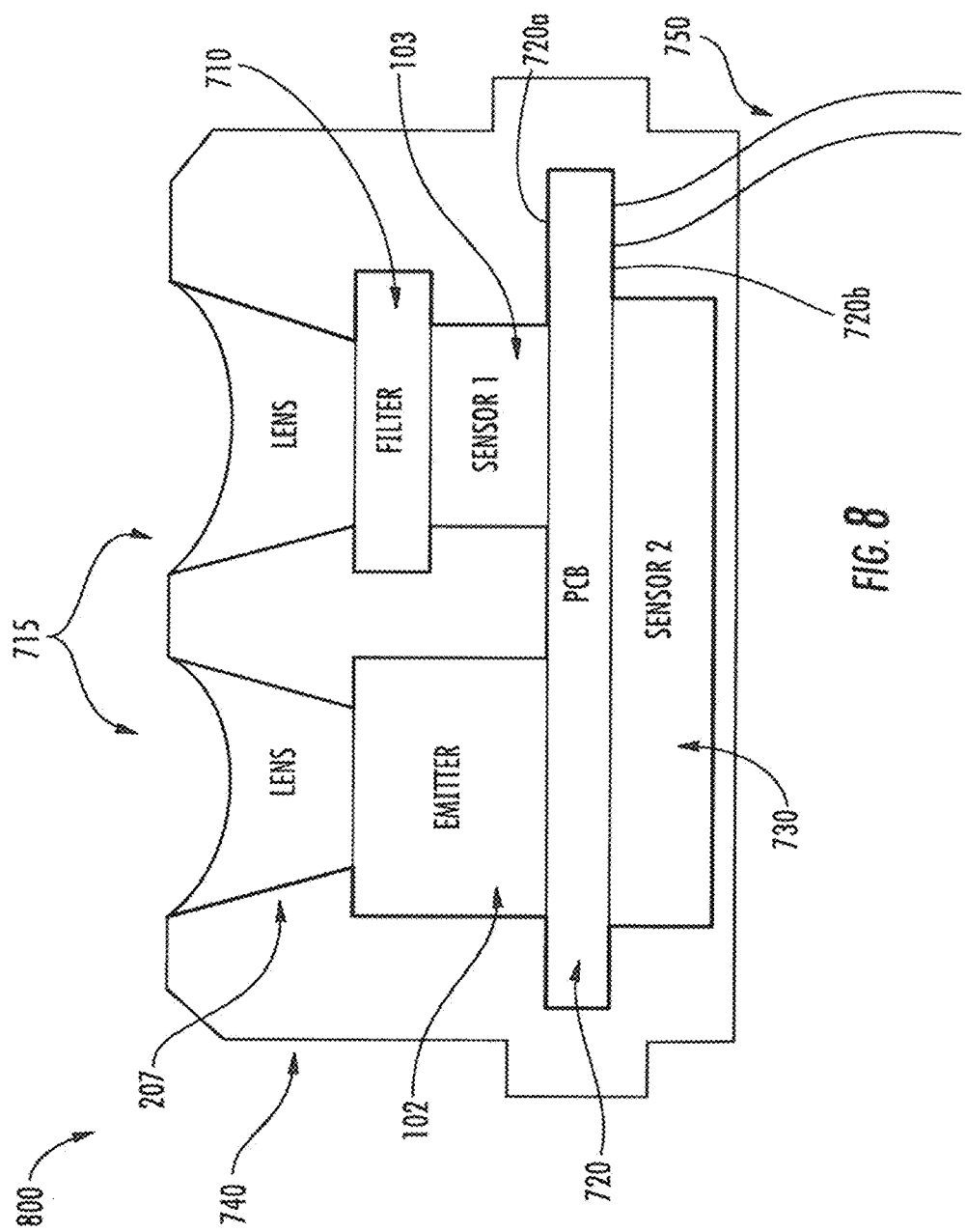

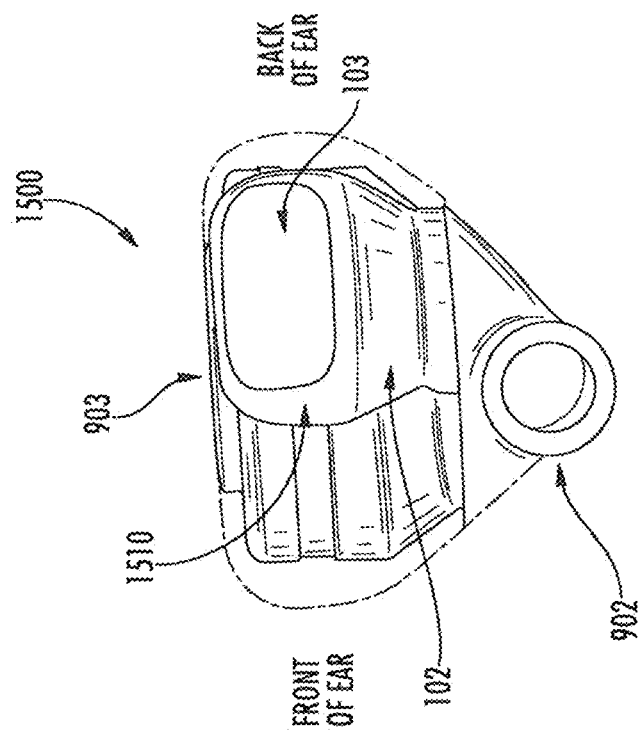
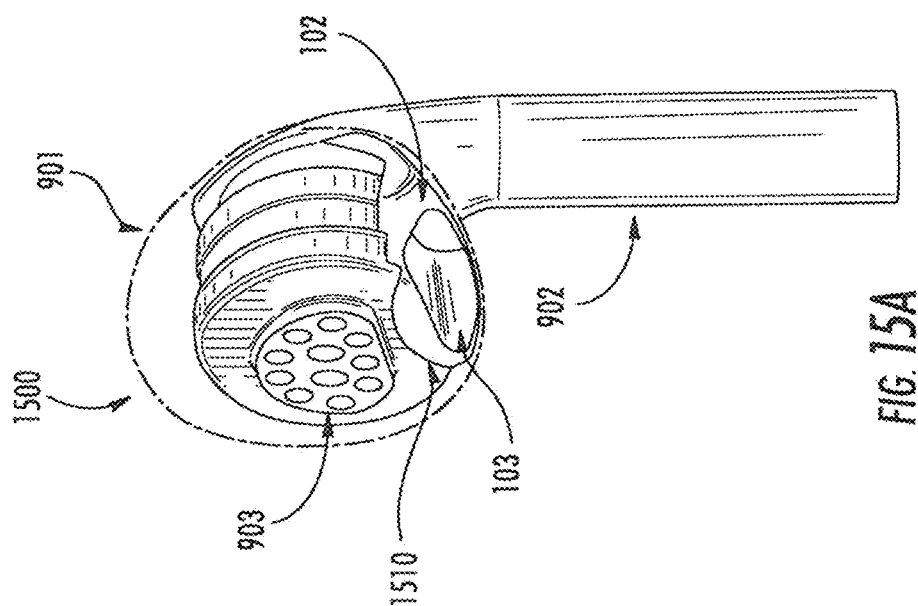
FIG. 15B
FIG. 15A

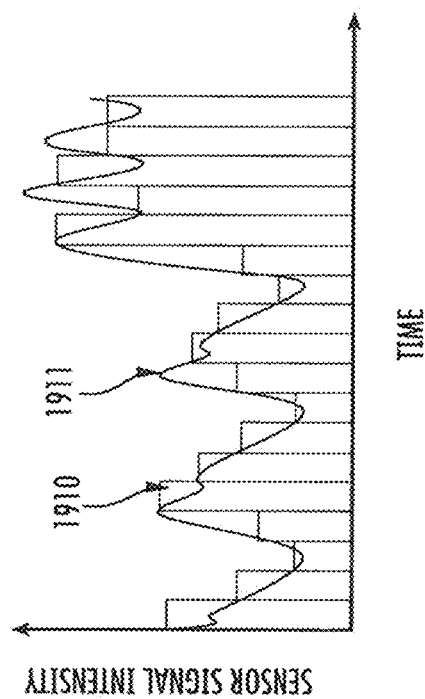
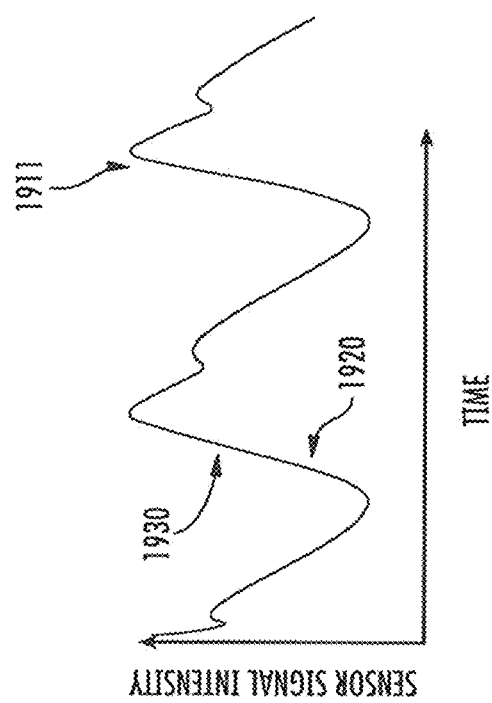

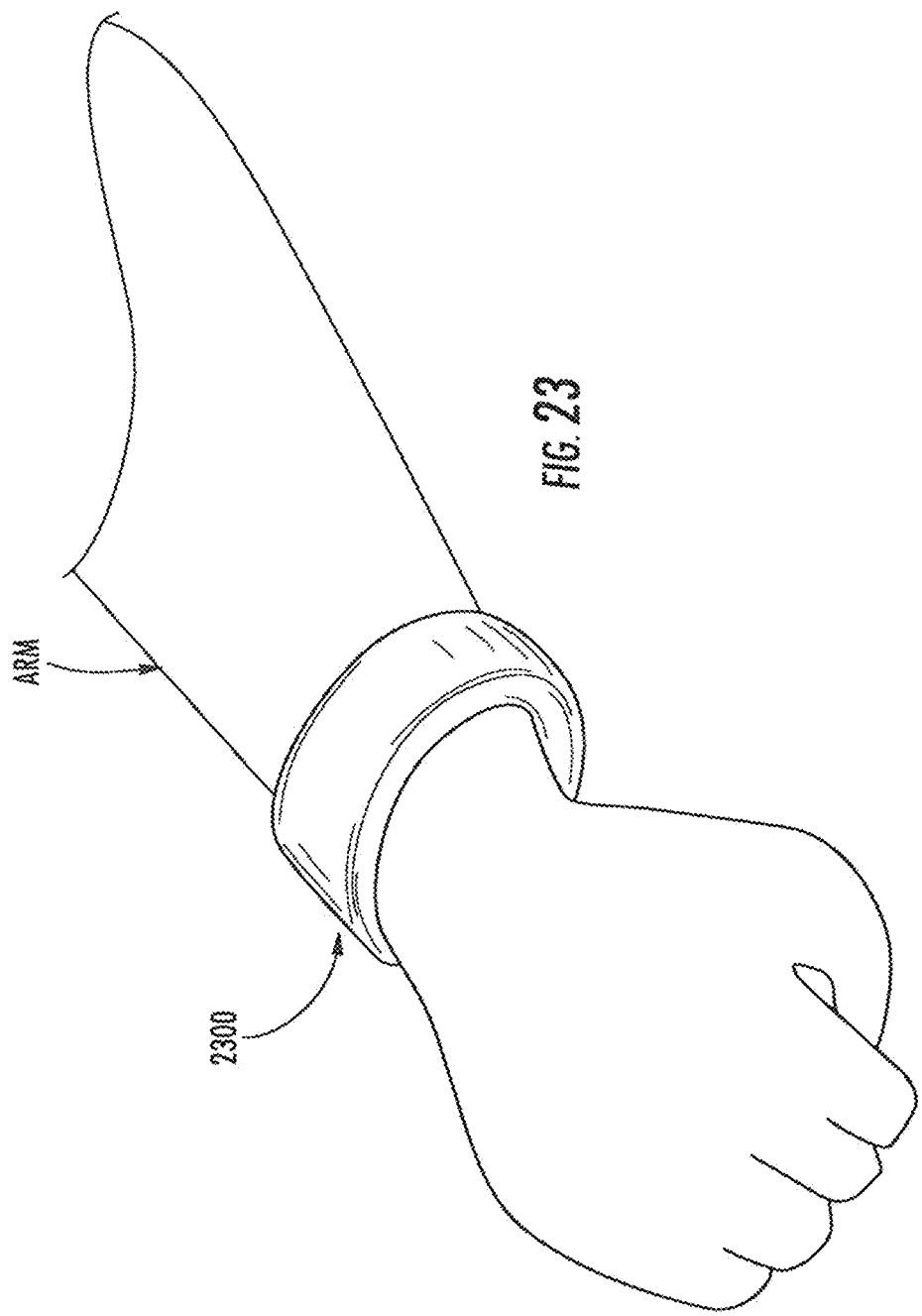

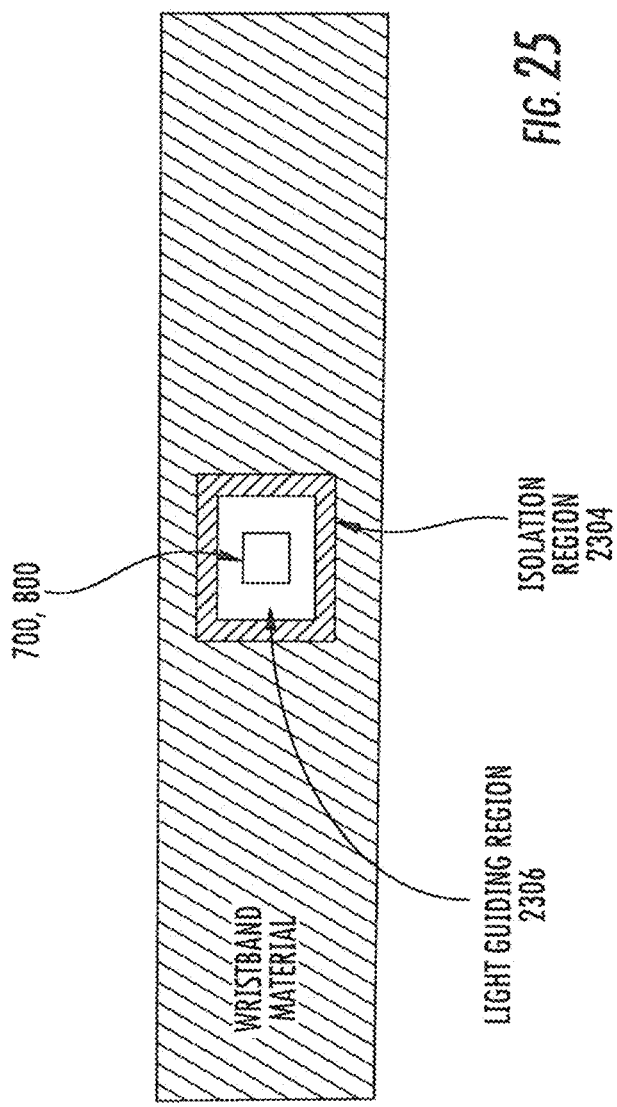

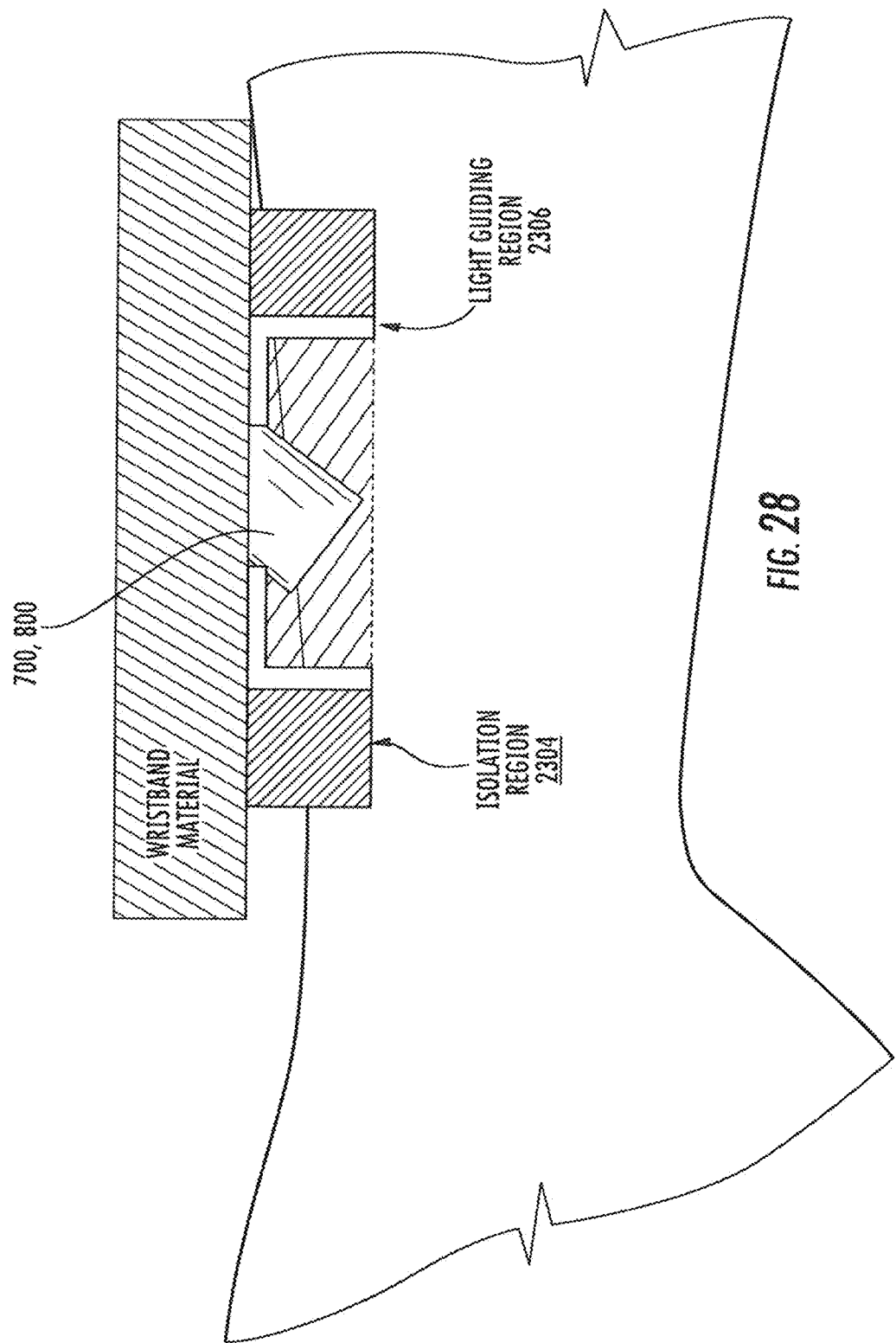

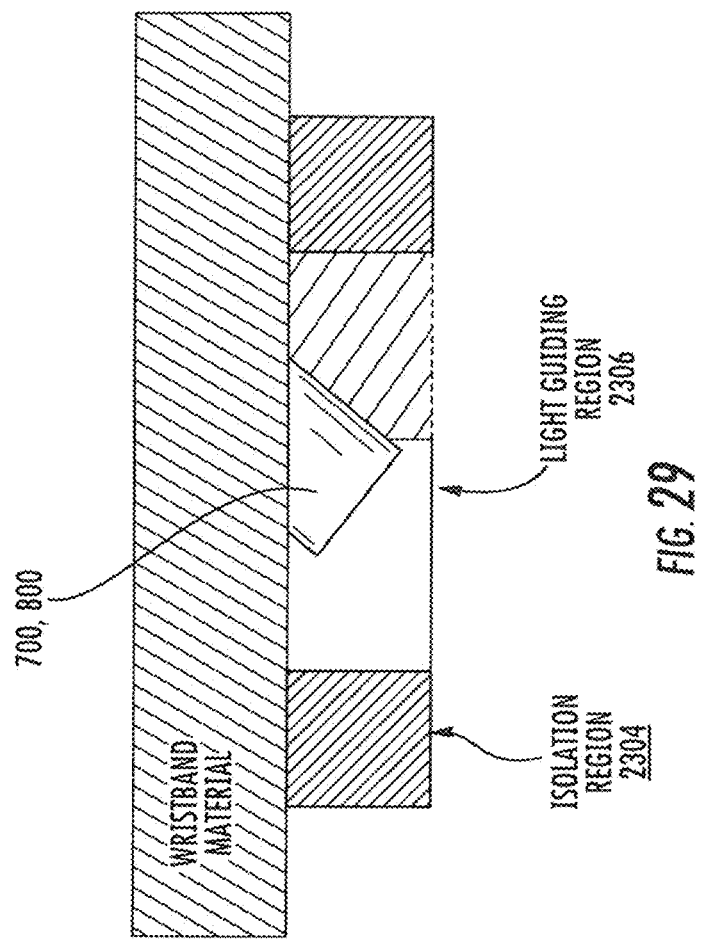

HEADSETS WITH ANGLED SENSOR MODULES

RELATED APPLICATIONS

This application is a continuation application of U.S. patent application Ser. No. 14/511,692, filed Oct. 10, 2014, which is a continuation application of U.S. patent application Ser. No. 13/358,102, filed Jan. 25, 2012, now U.S. Pat. No. 8,888,701, which claims the benefit of and priority to U.S. Provisional Patent Application No. 61/436,664 filed Jan. 27, 2011, the disclosures of which are incorporated herein by reference as if set forth in their entireties.

FIELD OF THE INVENTION

The present invention relates generally to monitoring apparatus and methods and, more particularly, to physiological monitoring apparatus and methods.

BACKGROUND OF THE INVENTION

There is growing market demand for personal health and environmental monitors, for example, for gauging overall health, fitness, metabolism, and vital status during exercise, athletic training, work, public safety activities, dieting, daily life activities, sickness, and physical therapy. However, traditional wearable health monitors cannot measure physiological information accurately in typical daily environments. For example, environmental interference from sunlight, temperature changes, and motion-coupled environmental noise can present measurement artifacts on wearable health monitors. These measurement artifacts can reduce sensor accuracy, generate false measurements, and prevent accurate health, fitness, and vital status monitoring. As such, improved ways of removing or preventing environmental interference from measurements taken from wearable sensors are needed.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a medium (e.g., physiological material of a subject), having a region of interest, is monitored via a sensor module having at least one energy emitter for interrogating the medium with energy to generate an energy response associated with the medium, at least one circuit to drive at least one energy emitter, at least one detector for detecting the energy response associated with the medium, a filter that removes time-varying environmental interference from the energy response signal, and a processor that controls operations of the energy emitter, detector, and filter.

According to some embodiments of the present invention, a wearable monitoring apparatus includes a housing (e.g., an earpiece, earbud, etc.), and a sensor module disposed within or attached to the housing. The housing is configured to be attached to a body of a subject, for example the ear. The sensor module includes an energy emitter, a detector, a filter, and at least one processor. The energy emitter directs energy (e.g., optical energy, acoustic energy, ultrasonic energy, electromagnetic radiation, electrical energy, mechanical energy, magnetic energy, nuclear energy, etc.) at a target region of the subject and the detector detects an energy response signal from the subject. The energy response signal is associated with a physiological condition of the subject (e.g., heart rate, pulse pressure, respiration rate, lactic threshold, blood pressure, volume of blood flow through a blood vessel, blood metabolite level, blood oxygen level, size of at least one blood vessel, etc.). The filter removes or attenuates time-varying environmental interference from the energy response signal, wherein the time-varying environmental interference is caused by one or more of the following: sunlight, ambient light, airflow, temperature, etc.

The at least one processor controls operations of the energy emitter, detector, and/or filter. In some embodiments of the present invention, the at least one processor is configured to process the detected energy response signal and produce an extracted energy response signal.

In some embodiments of the present invention, the energy emitter emits pulsed or modulated energy.

In some embodiments of the present invention, the energy emitter comprises at least one optical emitter, and the detector comprises at least one optical detector. Exemplary optical emitters include, but are not limited to, laser diodes (LDs), light-emitting diodes (LEDs), and organic light-emitting diodes (OLEDs). Exemplary optical detectors include, but are not limited to, photodetectors, photodiodes, phototransistors, photoactive resistors, photomultiplier tubes, photomultiplier diodes, photodetector modules, and the like.

In some embodiments of the present invention, at least one portion of the housing comprises optically transmissive material through which light from the at least one optical emitter can pass. In some embodiments of the present invention, at least one portion of the housing comprises material configured to attenuate (e.g., reduce or block) light reaching the at least one optical detector at one or more selected wavelengths.

In some embodiments of the present invention, the monitoring apparatus includes at least one analog-to-digital (ADC) converter that converts analog signals generated by the detector to digital signals.

According to some embodiments of the present invention, a monitoring apparatus includes a housing configured to be attached to the ear of a subject, and a sensor module disposed within or attached to the housing. The sensor module includes an optical emitter, a detector, a motion/position sensor, a filter, and at least one processor that controls operations of the optical emitter, detector, and/or filter. The optical emitter directs optical energy at a target region of the subject and the detector detects an optical energy response signal from the subject, wherein the energy response signal is associated with a physiological condition of the subject. Light-opaque material surrounds at least part of the sensor module to prevent ambient light from interfering with the detector. Output from the motion/position sensor is associated with the motion or position between the housing and ear of the subject. The filter removes or attenuates time-varying environmental interference from the optical energy response signal, wherein the time-varying environmental interference is caused by one or more of the following: sunlight, ambient light, airflow, and temperature.

According to some embodiments of the present invention, a sensor module includes a printed circuit board (PCB), in some cases having opposite first and second sides, an optical emitter attached to at least one side of the PCB, an optical detector attached to at least one side of the PCB adjacent to the optical emitter, an optical filter overlying at least a portion of the optical detector, and light-opaque material adjacent to the optical detector. The optical filter is configured to attenuate (e.g., reduce or block) light at one or more selected wavelengths, and the light-opaque material prevents ambient light from interfering with the optical detector.

In some embodiments of the present invention, the optical filter has a surface area greater than a surface area of the optical detector, and the optical filter overlies the optical detector such that a periphery of the optical filter overlaps a periphery of the optical detector.

In some embodiments of the present invention, light-opaque material surrounds the optical emitter and optical detector such that the optical emitter and optical detector are not in direct optical communication with each other. In some embodiments of the present invention, the light-opaque material includes a first aperture in communication with the optical emitter, and a second aperture in communication with the optical detector.

In some embodiments of the present invention, the sensor module includes a lens positioned above at least one of the optical emitter and filter. The lens may include respective first and second portions configured to matingly engage respective first and second apertures in the light-opaque material.

In other embodiments of the present invention, a first lens is positioned within the first aperture and is in optical communication with the optical emitter, and a second lens is positioned within the second aperture and is in optical communication with the optical detector. The first lens focuses light emitted by the optical emitter and the second lens focuses light toward the optical detector.

In some embodiments of the present invention, a second optical detector is attached to the PCB second side.

According to other embodiments of the present invention, an earbud for a headset includes a housing that is configured to be positioned within an ear of a subject, a speaker, and at least one sensor module disposed within or attached to the housing. The at least one sensor module includes a printed circuit board (PCB) having opposite first and second sides, an optical emitter attached to at least one side of the PCB that directs electromagnetic radiation at a target region of the ear, an optical detector attached to at least one side of the PCB adjacent to the optical emitter that detects an energy response signal associated with a physiological condition of the subject from the subject, and an optical filter overlying at least a portion of the optical detector, wherein the optical filter is configured to attenuate (e.g., reduce or block) light at one or more selected wavelengths. A filter may be included that removes time-varying environmental interference from the energy response signal. Time-varying environmental interference may be caused by one or more of the following: sunlight, ambient light, airflow, temperature, etc. The at least one sensor module may include at least one processor that controls operations of the optical emitter, optical detector, and/or filter.

In some embodiments of the present invention, the optical filter has a surface area greater than a surface area of the optical detector, and the optical filter overlies the optical detector such that a periphery of the optical filter overlaps a periphery of the optical detector.

In some embodiments of the present invention, light-opaque material surrounds the optical emitter and optical detector such that the optical emitter and optical detector are not in direct optical communication with each other. In some embodiments of the present invention, the light-opaque material includes a first aperture in communication with the optical emitter, and a second aperture in communication with the optical detector.

In some embodiments of the present invention, the at least one sensor module include a lens positioned above at least one of the optical emitter and filter. The lens may include respective first and second portions configured to matingly engage respective first and second apertures in the light-opaque material.

In other embodiments of the present invention, a first lens is positioned within the first aperture and is in optical communication with the optical emitter, and a second lens is positioned within the second aperture and is in optical communication with the optical detector. The first lens focuses light emitted by the optical emitter and the second lens focuses light toward the optical detector.

In some embodiments of the present invention, a second optical detector is attached to the PCB second side.

In some embodiments of the present invention, one or more portions of the earbud housing include optically transmissive material through which light from the optical emitter can pass.

In some embodiments of the present invention, one or more portions of the housing include material configured to attenuate (e.g., reduce or block) light reaching the optical detector at one or more selected wavelengths.

In some embodiments of the present invention, the at least one sensor module includes an analog-to-digital (ADC) converter that converts analog signals generated by the optical detector to digital signals.

In some embodiments of the present invention, the at least one sensor module includes at least one motion/position sensor attached to at least one side of the PCB.

In some embodiments of the present invention, the at least one sensor module housing includes a soft material which deforms when inserted within an ear and that facilitates retention of the earbud within an ear. In other embodiments, the at least one sensor module housing has a shape that facilitates retention of the earbud within an ear.

In some embodiments of the present invention, a portion of the at least one sensor module housing includes optically transmissive material through which light from the optical emitter can pass, and wherein the housing includes a soft material adjacent to the optically transmissive material which deforms when inserted within an ear and that facilitates retention of the earbud within an ear.

In some embodiments of the present invention, a portion of the at least one sensor module housing includes material configured to diffuse light from the optical detector and/or diffuse light to the optical detector.

In some embodiments of the present invention, the at least one sensor module comprises two sensor modules in spaced apart relationship.

According to other embodiments of the present invention, a method of monitoring at least one physiological property of a subject includes directing pulsed energy at a target region of the subject via an energy emitter, obtaining a first energy response signal from the subject when the emitter is on, obtaining a second energy response signal from the subject when the emitter is off, and processing the first and second energy response signals via an interference filter to produce a processed energy response signal that is associated with a physiological condition (e.g., heart rate, pulse pressure, respiration rate, lactic threshold, blood pressure, volume of blood flow through a blood vessel, blood metabolite level, blood oxygen level, size of at least one blood vessel, etc.) of the subject, wherein the filter removes or attenuates time-varying environmental interference caused by one or more of the following: sunlight, ambient light, airflow, temperature, etc. Directing pulsed energy at a target region may include directing energy selected from the group consisting of optical energy, acoustic energy, ultrasonic energy, electromagnetic radiation, electrical energy, magnetic energy, mechanical energy, nuclear energy, etc.

In some embodiments of the present invention, the interference filter employs a spectral method to remove or attenuate time-varying environmental interference. In some embodiments of the present invention, the interference filter employs an FIR filtering method to remove or attenuate time-varying environmental interference.

In some embodiments of the present invention, the processed energy response signal is transmitted to a remote device, for example wirelessly transmitted.

In some embodiments of the present invention, the environmental interference may comprise ambient light, sunlight, room light, wind, sound, mechanical interference, electrical interference, temperature changes, or the like.

In some embodiments of the present invention, the geometrical configuration of an emitter and detector may be oriented to maximize the collection of the energy response signal associated with physiological conditions and to minimize the collection of the unwanted scattered light response.

In some embodiments, multiple emitters, detectors, lenses, light guides, and/or diffusion regions may be employed within a sensor module.

Emitters and detectors, according to some embodiments of the present invention, may be configured to generate a more universal earbud sensor design. In some embodiments, this may be achieved by employing a diffusion area.

In some embodiments of the present invention, an earbud may comprise an interchangeable tip, wherein optical coupling may be integrated within the earbud to communicate light to/from the ear region through the interchangeable tip.

In some embodiments of the present invention, a physiological condition monitored, such as heart rate, for example, may be modulated to improve filtering and then demodulated to generate the desired output.

In some embodiments of the present invention, an interference filter may employ at least one motion/position sensor to remove interference from a desired physiological signal, such as to remove motion-coupled sunlight interference from a heart rate signal.

According to some embodiments of the present invention, a wearable monitoring apparatus includes a substrate configured to be attached to a body of a subject, and a sensor module attached to the substrate. The substrate may be configured to surround a portion of a body, and may be flexible. For example, the substrate may be a wristband, armband, legband, neckband, waistband, ankleband, footband, handband, ringband, headband, etc. In other embodiments, the substrate is configured to be adhesively attached to the body of the subject, similar to a bandage.

The sensor module includes an energy emitter, a detector, a filter, and at least one processor. The energy emitter directs energy (e.g., optical energy, acoustic energy, ultrasonic energy, electromagnetic radiation, electrical energy, mechanical energy, magnetic energy, nuclear energy, etc.) at a target region of the subject and the detector detects an energy response signal from the subject. The energy response signal is associated with a physiological condition of the subject (e.g., heart rate, pulse pressure, respiration rate, lactic threshold, blood flow, blood pressure, volume of blood flow through a blood vessel, blood metabolite level, blood oxygen level, size of at least one blood vessel, etc.). The filter removes or attenuates time-varying environmental interference from the energy response signal, wherein the time-varying environmental interference is caused by one or more of the following: sunlight, ambient light, airflow, temperature, etc.

The at least one processor controls operations of the energy emitter, detector, and/or filter. In some embodiments of the present invention, the at least one processor is configured to process the detected energy response signal and produce an extracted energy response signal.

In some embodiments of the present invention, the energy emitter emits pulsed or modulated energy.

In some embodiments of the present invention, the energy emitter comprises at least one optical emitter, and the detector comprises at least one optical detector. Exemplary optical emitters include, but are not limited to, LDs, LEDs, and OLEDs. Exemplary optical detectors include, but are not limited to, photodetectors, photodiodes, phototransistors, photoactive resistors, photomultiplier tubes, photomultiplier diodes, photodetector modules, and the like.

In some embodiments of the present invention, the apparatus includes optically transmissive material through which light from the at least one optical emitter can pass. In some embodiments of the present invention, the apparatus includes material configured to attenuate (e.g., reduce or block) light reaching the at least one optical detector at one or more selected wavelengths.

In some embodiments of the present invention, the monitoring apparatus includes at least one ADC converter that converts analog signals generated by the detector to digital signals.

The detectors that may be incorporated into headsets, earbuds, and/or substrates (e.g., wristbands, armbands, legbands, neckbands, waistbands, anklebands, footbands, handbands, ringbands, headbands, etc.) according to some embodiments of the present invention, may be configured to detect and/or measure one or more of the following types of physiological information/conditions: heart rate, pulse rate, breathing rate, blood flow, $VO_2$, $VO_2max$, heartbeat signatures, cardio-pulmonary health, organ health, metabolism, electrolyte type and/or concentration, physical activity, caloric intake, caloric metabolism, blood metabolite levels or ratios, blood pH level, physical and/or psychological stress levels and/or stress level indicators, drug dosage and/or dosimetry, physiological drug reactions, drug chemistry, biochemistry, position and/or balance, body strain, neurological functioning, brain activity, brain waves, blood pressure, cranial pressure, hydration level, auscultatory information, auscultatory signals associated with pregnancy, physiological response to infection, skin and/or core body temperature, eye muscle movement, blood volume, inhaled and/or exhaled breath volume, physical exertion, exhaled breath physical and/or chemical composition, the presence and/or identity and/or concentration of viruses and/or bacteria, foreign matter in the body, internal toxins, heavy metals in the body, anxiety, fertility, ovulation, sex hormones, psychological mood, sleep patterns, hunger and/or thirst, hormone type and/or concentration, cholesterol, lipids, blood panel, bone density, organ and/or body weight, reflex response, sexual arousal, mental and/or physical alertness, sleepiness, auscultatory information, response to external stimuli, swallowing volume, swallowing rate, sickness, voice characteristics, voice tone, voice pitch, voice volume, vital signs, head tilt, allergic reactions, inflammation response, auto-immune response, mutagenic response, DNA, proteins, protein levels in the blood, water content of the blood, pheromones, internal body sounds, digestive system functioning, cellular regeneration response, healing response, stem cell regeneration response, etc.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

FIG. 8 illustrates a sensor module with a concave lens configuration, according to some embodiments of the present invention.

FIG. 15A is a side perspective view of a multi-detector earbud comprising two separate optical coupling areas, according to some embodiments of the present invention.

FIG. 15B is a bottom plan view of the earbud of FIG. 15A.

FIGS. 19A and 19B are graphs illustrating digital sampling of a detector signal, according to some embodiments of the present invention.

FIG. 23 is a perspective view of a monitoring apparatus including a sensor module of FIG. 7 or FIG. 8, according to some embodiments of the present invention, and wherein the monitoring apparatus is adapted to fit around a wrist of a person.

FIG. 25 is a plan view of the sensor module of the monitoring apparatus of FIG. 23.

FIG. 28 illustrates the sensor module of the monitoring apparatus of FIG. 23 in contact with the skin of a subject.

FIG. 29 is an enlarged side view of the sensor module of the monitoring apparatus of FIG. 23, according to other embodiments of the present invention.

DETAILED DESCRIPTION

Figure 1:
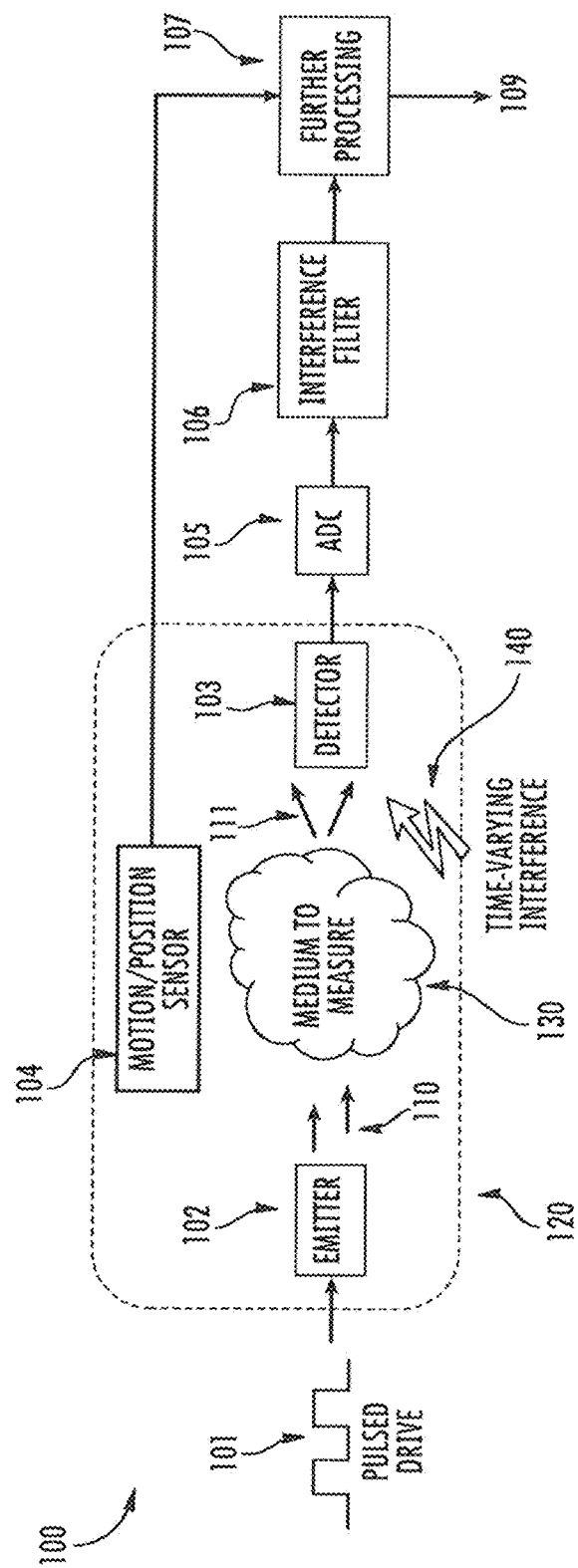
FIG. 1 schematically illustrates an interference filtering apparatus and method, according to some embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second, and the like, are used herein to describe various features/elements, these features/elements should not be limited by these terms. These terms are only used to distinguish one feature/element from another feature/element. Thus, a first feature/element discussed below could be termed a second feature/element, and similarly, a second feature/element discussed below could be termed a first feature/element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "headset" includes any type of device or earpiece that may be attached to or near the ear (or ears) of a user and may have various configurations, without limitation. Headsets as described herein may include mono headsets (one earbud) and stereo headsets (two earbuds), earbuds, hearing aids, ear jewelry, face masks, headbands, and the like.

The term "modulated energy", as used herein, refers to energy (e.g., optical energy, acoustic energy, ultrasonic energy, electromagnetic radiation, electrical energy, magnetic energy, mechanical energy, nuclear energy, etc.) that is emitted in pulses and/or that is emitted such that the amplitude, frequency, phase, or intensity is varied. A pulsed energy source modulates by effectively multiplying by a waveform that is a periodic sequence of zeros and ones.

The term "real-time" is used to describe a process of sensing, processing, or transmitting information in a time frame which is equal to or shorter than the minimum timescale at which the information is needed. For example, the real-time monitoring of pulse rate may result in a single average pulse-rate measurement every minute, averaged over 30 seconds, because an instantaneous pulse rate is often useless to the end user. Typically, averaged physiological and environmental information is more relevant than instantaneous changes. Thus, in the context of embodiments of the present invention, signals may sometimes be processed over several seconds, or even minutes, in order to generate a "real-time" response.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature. However, in some cases, the term "psychological" is called-out separately to emphasize aspects of physiology that are more closely tied to conscious or subconscious brain activity rather than the activity of other organs, tissues, or cells.

The term "body" refers to the body of a subject (human or animal) who may wear a headset incorporating embodiments of the present invention.

In the included figures, various embodiments will be illustrated and described. However, it is to be understood that embodiments of the present invention are not limited to those worn by humans.

The terms "creature" and "subject", as used herein, are interchangeable and include humans and animals.

The human ear is an ideal location for wearable health and environmental monitors. The ear is a relatively immobile platform that does not obstruct a person's movement or vision. Headsets located at an ear have, for example, access to the inner-ear canal and tympanic membrane (for measuring core body temperature), muscle tissue (for monitoring muscle tension), the pinna and earlobe (for monitoring blood gas levels), the region behind the ear (for measuring skin temperature and galvanic skin response), and the internal carotid artery (for measuring cardiopulmonary functioning), etc. The ear is also at or near the point of exposure to: environmental breathable toxicants of interest (volatile organic compounds, pollution, etc.); noise pollution experienced by the ear; and lighting conditions for the eye. Furthermore, as the ear canal is naturally designed for transmitting acoustical energy, the ear provides a good location for monitoring internal sounds, such as heartbeat, breathing rate, and mouth motion.

Wireless, Bluetooth®-enabled, and/or other personal communication headsets may be configured to incorporate physiological and/or environmental sensors, according to some embodiments of the present invention. As a specific example, Bluetooth® headsets are typically lightweight, unobtrusive devices that have become widely accepted socially. Moreover, Bluetooth® headsets are cost effective, easy to use, and are often worn by users for most of their waking hours while attending or waiting for cell phone calls. Bluetooth® headsets configured according to embodiments of the present invention are advantageous because they provide a function for the user beyond health monitoring, such as personal communication and multimedia applications, thereby encouraging user compliance. Exemplary physiological and environmental sensors that may be incorporated into a Bluetooth® or other type of headsets include, but are not limited to accelerometers, auscultatory sensors, pressure sensors, humidity sensors, color sensors, light intensity sensors, pressure sensors, etc.

Optical coupling into the blood vessels of the ear may vary between individuals. As used herein, the term "coupling" refers to the interaction or communication between excitation light entering a region and the region itself. For example, one form of optical coupling may be the interaction between excitation light generated from within a light-guiding earbud and the blood vessels of the ear. Light guiding earbuds are described in co-pending U.S. Patent Application Publication No. 2010/0217102, which is incorporated herein by reference in its entirety. In one embodiment, this interaction may involve excitation light entering the ear region and scattering from a blood vessel in the ear such that the intensity of scattered light is proportional to blood flow within the blood vessel. Another form of optical coupling may be the interaction between excitation light generated by an optical emitter within an earbud and the light-guiding region of the earbud.

Embodiments of the present invention are not limited to headsets that communicate wirelessly. In some embodiments of the present invention, headsets configured to monitor an individual's physiology and/or environment may be wired to a device that stores and/or processes data or there may be a combination of wired and wireless communications. In some embodiments, this information may be stored on the headset itself. Furthermore, embodiments of the present invention are not limited to earbuds. In some embodiments, the invention may be employed around another part of the body, such as a digit, finger, toe, limb, wrist, ankle, around the nose or earlobe, or the like. In other embodiments, the invention may be integrated into a patch, such as a bandage that sticks on a person's body.

FIG. 1 illustrates an interference filtering apparatus/method 100, according to some embodiments of the present invention. A medium 130, preferably physiological material of a living subject, comprises at least one target region of interest 120 which is interrogated by energy 110, preferably modulated energy, such as pulsed energy, generated by an energy emitter 102. A pulsed driving circuit 101 is used to drive at least one energy emitter 102 at one or more pulsed frequencies to interrogate at least one target region of at least one medium 130 with the pulsed energy 110. The energy may be in the form of electromagnetic, acoustical, mechanical, nuclear, electrical, magnetic, thermal, or other forms of energy, but typically optical energy from the electromagnetic spectrum. The energy reaching the medium 130 can interact with the medium to generate at least one energy response signal 111, such as an optical scatter signal 111 between emitted optical energy 110 and the medium 130. The energy response 111 caused by this interaction is detected by at least one detector 103, configured to detect energy in the forms described above, but typically in the form of optical energy scattered from the medium 130. A motion/position sensor 104 may be configured to measure movement, positional changes, or inertial changes in the vicinity of the medium 130. The outputs of the detector 103 may be sent to at least one analog-to-digital convertor (ADC) 105 and the digitized output may be sent to at least one interference filter 106, which is configured to remove the effects of time-varying environmental interference 140 from the signal output of the detector 103. At least one motion/position sensor 104 may be incorporated in the interference filtering method 100 to provide a reference signal for removing the effects of motion from the extracted energy response signal 111 to produce a desired signal 109. For example, the output of the interference filter 106 may be further processed by signal extraction filter 107 to extract accurate information from the medium 130, and this signal extraction filter 107 may utilize the output of the motion/position sensor 104 to remove motion artifacts from the desired signal (the extracted energy response signal) 109. At least one signal processor (not shown) may be used to control the operations of the energy emitter 102, detector 103, filter 106, and/or other components of the interference filtering method 100.

In some embodiments of the present invention, a monitoring apparatus is configured to be a wearable monitor for monitoring at least one physiological condition of the wearer. In such an embodiment, pulsed electromagnetic energy 110 from at least one electromagnetic emitter 102, typically an optical emitter, is directed towards at least one physiological region 130, typically the ear region, of a subject. Examples of optical emitters include light-emitting diodes (LEDs), laser diodes (LDs), lamps, organic emitters (such as OLEDs), and the like. The sensor components (102, 103, and 104) may be integrated within the ear region 120 in the form-factor of an earbud or other ear-worn form-factor such that the measurement medium 130 comprises blood vessels and/or blood flow within the ear region. The intensity of the pulsed optical energy 110 is modulated by at least one pulsed driving circuit 101 such that the intensity is time-varying with at least two states, preferably an on state and an off state. This time-varying energy generates a time-varying energy response, typically an optical interaction response, such as optical absorption, modulation, scatter, transmission, luminescence, or the like, from the physiological region 130. A first optical interaction response is obtained by at least one detector 103, typically an optical detector, when the pulsed optical energy 110 is in the on state. A second energy response, in this case a second optical interaction response, is obtained by the optical detector 103 when the pulsed optical energy 110 is in the off state. (In some cases, other optical interaction responses may be collected in other modulated states of the pulsed energy 110.) The first and second energy response signals are digitized by at least one ADC 105 and the digitized signals are processed via an interference filter 106 to produce a processed energy response signal that is associated with a physiological condition of the subject, wherein the filter removes time-varying environmental interference caused by an interferant, such as sunlight, ambient light, airflow, temperature, etc. The output of the interference filter 106 is then processed by a signal extraction filter 107 to accurately extract at least one physiological property of the subject. A motion/position sensor 104 may be configured to measure the motion/position between the medium 130 and the emitter 102, the detector 103, and/or the time-varying interference 140, for example, caused by motion of the subject. The output signal of the motion sensor 104 may provide a motion artifact reference to the signal extraction filter 107 such that the motion/position information may be selectively removed from the desired signal output. Incorporating a motion sensor in embodiments of the present invention may be particularly important because time-varying interference, such as sunlight hitting an earbud, is often modulated by motion, and monitoring and subtracting this motion from the desired output may be critical to generating an accurate physiological signal in the midst of daily life activities of the subject.

Figure 2:
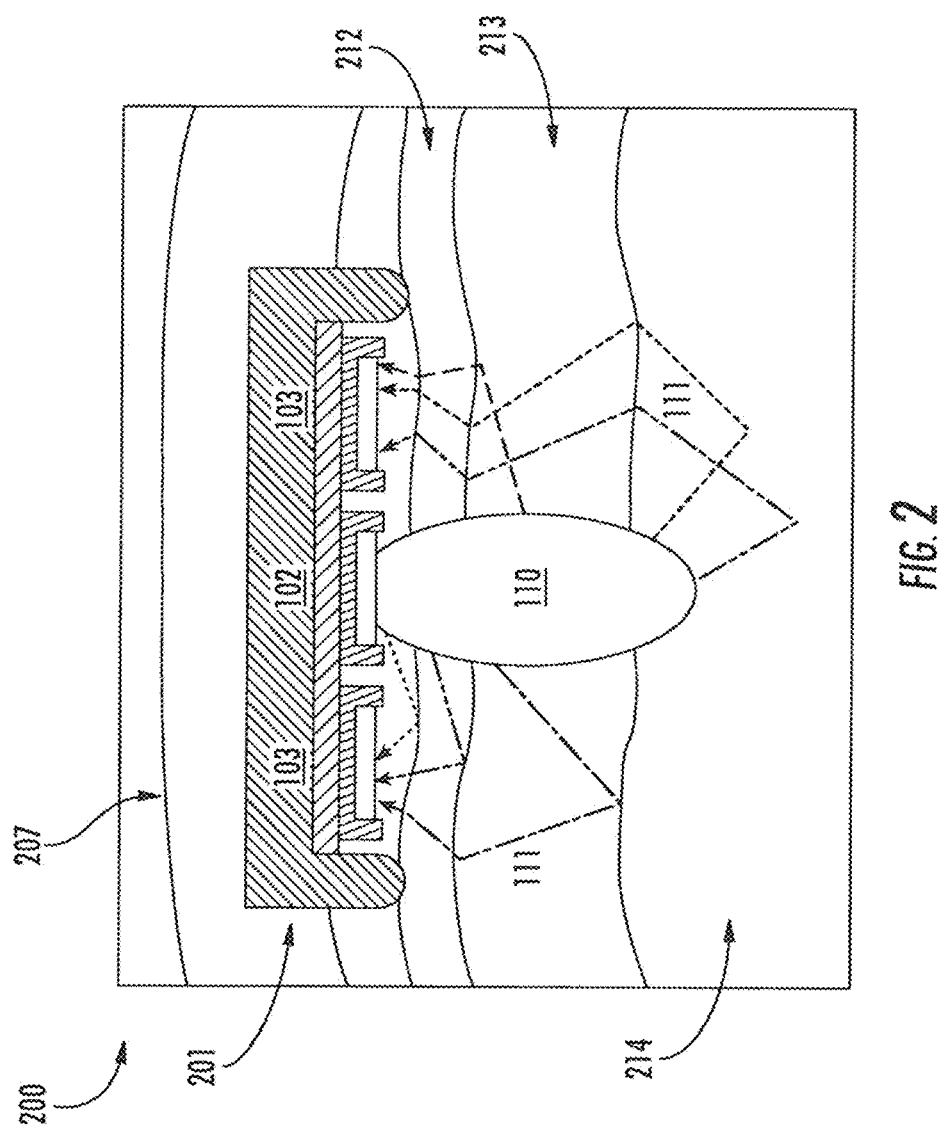
FIG. 2 illustrates a multi-wavelength reflection-mode pulse oximetry apparatus that may be utilized in accordance with some embodiments of the present invention.

Various forms of energy 110 can be used to interrogate one or more mediums 130 and to characterize those mediums by detectors 103 configured to detect the energy responses caused by the interaction of the energy 110 with the medium 130. For example, optical energy 110 can be used to interrogate a target region of skin and blood 130 to provide information regarding a physiological condition of a subject, such as a measure of blood oxygen levels of the subject by pulse oximetry. A specific example of the optophysiological interaction between light and a physiological medium 130 comprising the skin, blood vessels, and blood of a subject is shown in the reflective optical detection configuration 200 of FIG. 2. At least one sensor module 207, disposed within at least one housing configured to be attached to a body of a subject, may be in physical proximity to the skin of the subject, as shown in the reflective pulse oximetry setup 200 where reflected optical wavelengths 111 are measured, as opposed to measuring transmitted optical wavelengths. Optical emitter and optical detector wavelengths for pulse oximetry and photoplethysmography may include virtually any wavelength of electromagnetic radiation, but particularly useful are UV, visible, and IR wavelengths. In the illustrated embodiment, an optical source-detector assembly 201, including an optical emitter 102 and optical detectors 103, is integrated into sensor module 207 to generate optical wavelengths 110 and monitor the resulting scattered optical energy 111. The optical source-detector assembly 201 may contain one or more optical sources emitting one or more optical wavelengths, as well as one or more optical detectors detecting one or more optical wavelengths. The epidermis 212, dermis 213, and subcutaneous 214 layers of skin tissue of a human are shown in FIG. 2 for reference. The scattered optical energy 111 may be modulated in intensity by changes in physiological condition, such as: changes in blood flow in the blood vessels, changes in physical motion of the body, changes in blood metabolite levels (such as blood gases, bilirubin, glucose, lactic acid, and the like), respiration, heart rate, pulse pressure, blood pressure, and other physiological changes. In some cases, the scattered optical energy 111 may be luminescent or preferentially polarized energy from the skin, blood, blood metabolites, drugs, or other materials in the body. Thus, the energy response signal 111 may contain information associated with at least one physiological condition of the subject.

Figure 3:
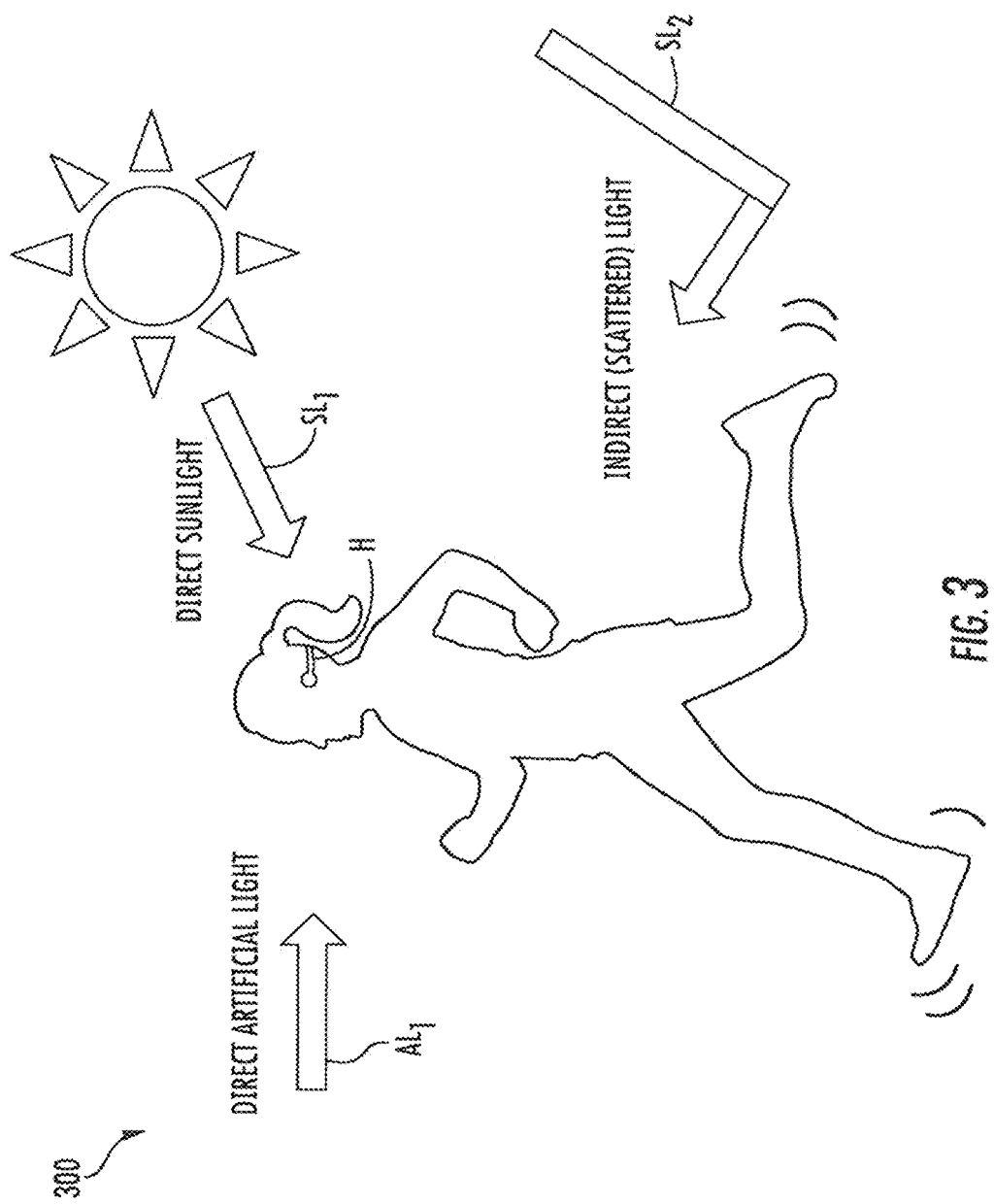
FIG. 3 illustrates various types of time-varying environmental interference.
Figure 4B:
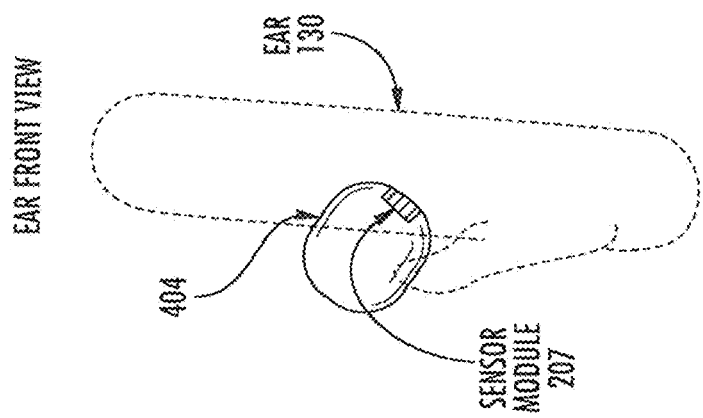
FIG. 4B is a front view of a human ear with an earbud monitor, according to some embodiments of the present invention, inserted therein.
Figure 4A:
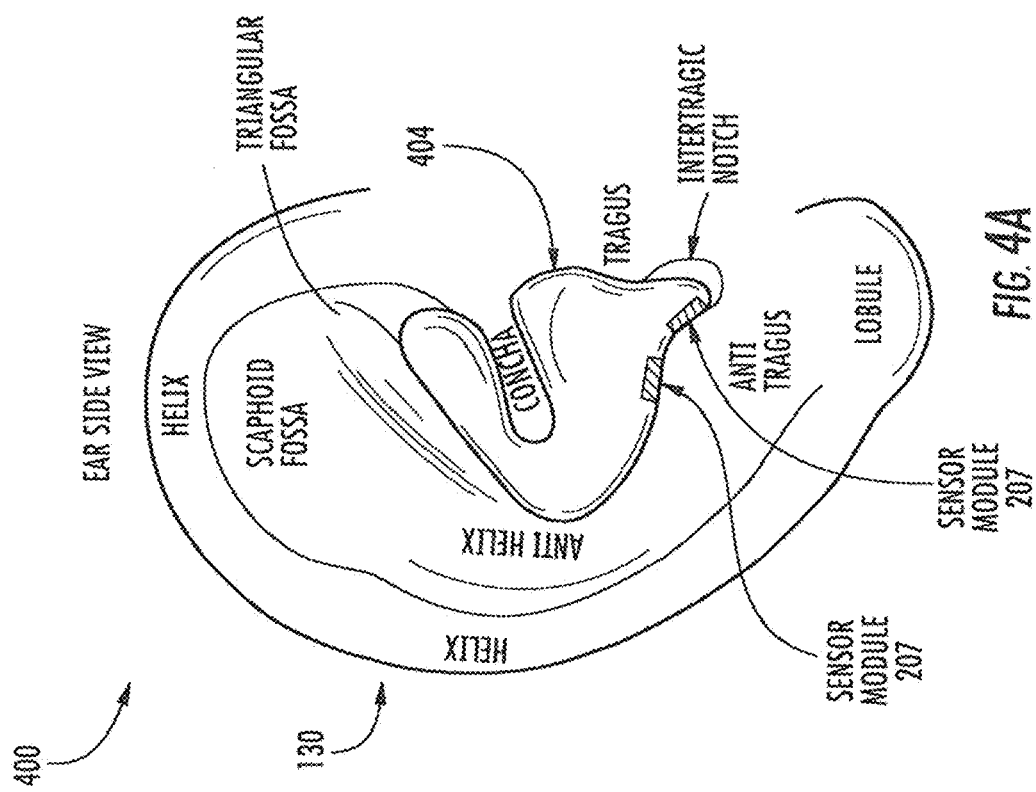
FIG. 4A is a side view of a human ear with an earbud monitor, according to some embodiments of the present invention, inserted therein.

In real-world environments, the energy response signal 111 collected by a wearable sensor module 207 may be corrupted by time-varying environmental interference 140 (FIG. 1). Moreover, the energy response signal 111 may be even further corrupted by motion of the subject in a time-varying environment. For example, the motion caused by running may cause motion with respect to the emitter 102, detector 103, and medium 130 (in this case tissue of the subject), and this motion may cause an unwanted signal on the detector 103. Moreover, the time-varying environmental interference 140 (FIG. 1) may be caused by, or exacerbated by, the motion of the subject. A specific example of time-varying interference in a real-world environment 300 is summarized in FIG. 3. In FIG. 3, the runner is wearing an audio headset H containing biometric monitoring technology, such as Valencell's Healthset® brand technology (Valencell, Inc., Raleigh, N.C.), where at least one photoplethysmography sensor module 207 (FIG. 2) is included within a biometric audio earbud 404 as shown in FIG. 4. The sensor module 207 may contain at least one optical emitter 102, at least one optical detector 103, and at least one processor to measure heart rate, respiration rate, pulse pressure, motion, and/or other physiological conditions near the ear region 130 of the subject. These types of measurements may be achieved by detecting the optical scatter response 111 from the ear region as summarized in FIG. 2. However, direct sunlight $SL_1$, indirect sunlight $SL_2$ and/or artificial light $AL_1$ from the environment may pass into the audio headset H. Time-varying sunlight $SL_1$, $SL_2$ and artificial ambient light $AL_1$ may impart time-varying optical interference 140 on the optical detector 103 embedded within the audio headset H. For example, a time-varying interference signal 140 (FIG. 1) from environmental light may impart substantial artifacts on an energy response signal 111 (FIG. 1) in many real life scenarios, such as when clouds pass through the sky, when a subject runs through shadows, when a subject runs to/from an artificial light source, and/or various thereof. These time-varying artifacts may be difficult to distinguish from the desired time-varying signals associated with time-varying physiological conditions. For example, the interference frequencies associated with a time-varying change in shadows, or the harmonics of these interference frequencies, may correspond with at least one signal frequency associated with footsteps, respiration, or heart rate, and the optical energy response 111 may contain convoluted information comprising interference signals and desired physiological signals.

Figure 5:
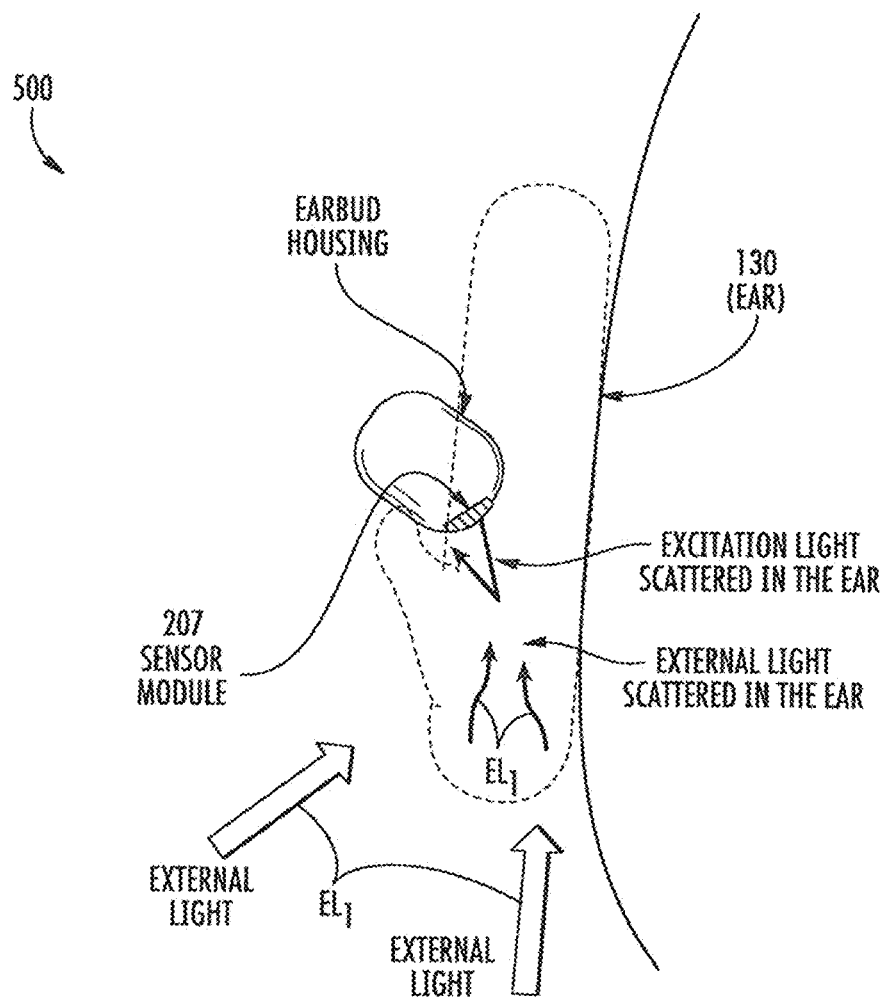
FIG. 5 is a schematic illustration of how external light interference can pass through a human ear and reach an optical detector in an earbud monitor attached to the ear.

The aforementioned time-varying interference signal 140 (FIG. 1) from direct sunlight $SL_1$ during jogging may be considered to be "direct interference", in that interfering sunlight may be detected directly by the optical detector 103. However, there may be cases where the interference may reach the optical detector 103 indirectly, causing the same signal processing challenges as with direct interference. For example, FIG. 5 summarizes how external light $EL_1$ from the sun or other external source can pass through the ear region and reach the optical detector 103 embedded within the sensor module 207. It may be difficult to distinguish this external light from the scattered excitation light associated with at least one physiological condition of the subject.

To address these problems, a novel embodiment of the interference filtering method and apparatus 100 is to employ both novel filtering methods and novel optomechanical earbud designs to: 1) remove sunlight from the desired signal response 109 (FIG. 1) and 2) prevent sunlight from reaching the detector 103 in the first place. Embodiments of the present invention described herein employ at least one of these approaches, but typically both, to teach how to make a wearable monitor, such as an earbud monitor, that may provide accurate information on physiological conditions in the midst of environmental noise, such as noise from ambient light and/or sunlight.

Figure 6:
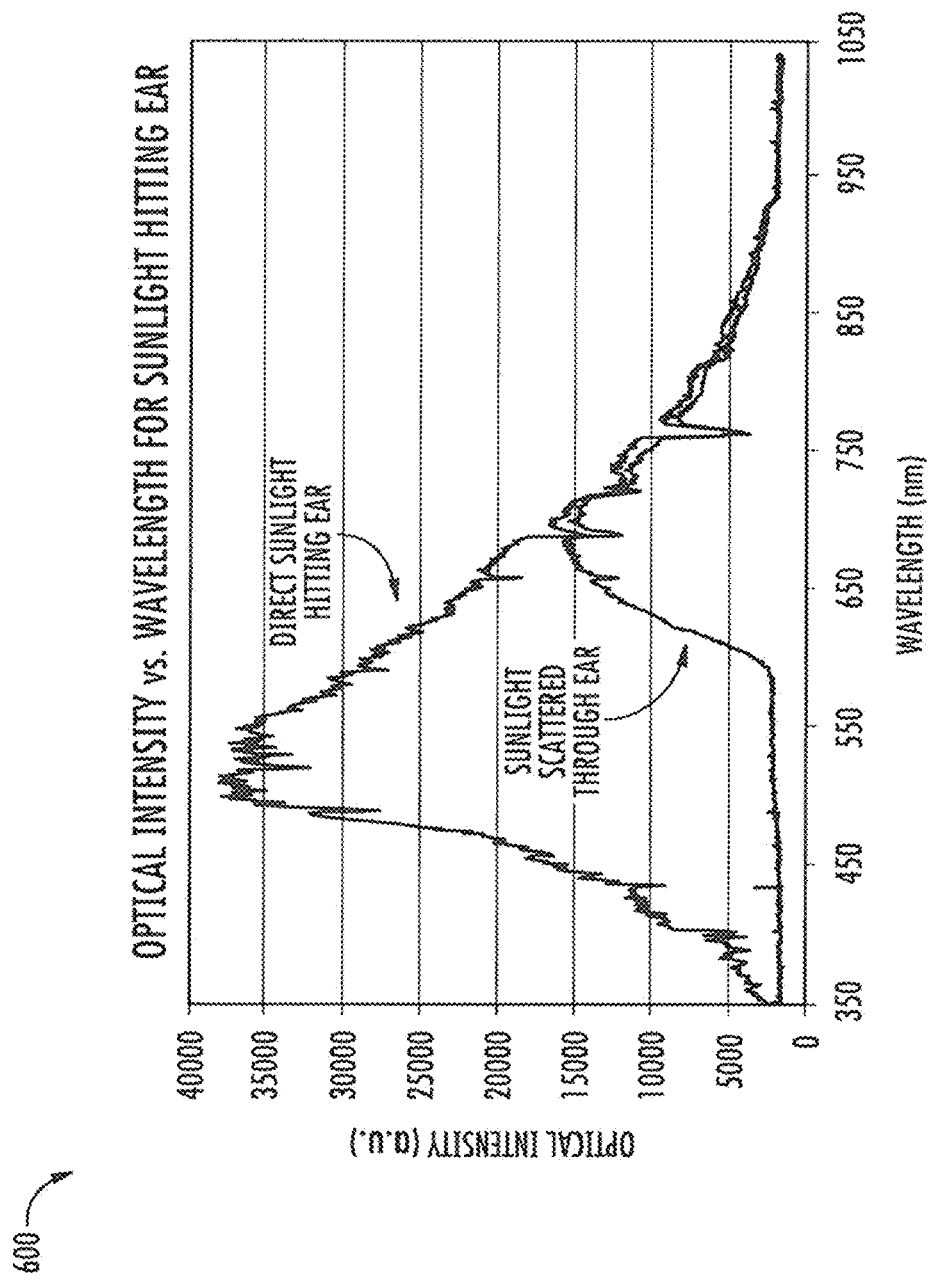
FIG. 6 is a comparison graph showing optical detector intensity vs. wavelength for direct sunlight exposure and indirect sunlight exposure caused by scattering through the ear region.

An experiment was performed by the Applicant to address the magnitude of the aforementioned sunlight convolution problem for an earbud physiological monitor. In this experiment, an optical spectrometer was optically coupled to a light guide embedded within an earbud worn by a subject in an outdoor sunlight environment. The only light reaching the spectrometer was light guided by an earbud-embedded light guide, positioned in the same basic region as the sensor module 207 shown in FIGS. 4 and 5. Thus, the light guide was guiding light from the ear region on one end towards the input of the spectrometer at the other end. Because the light guide was covered at one end by the spectrometer and at another end by the ear of the subject, the only significant light reaching the light guide was light generated by external light $EL_1$ passing through the ear, as shown in FIG. 5. With the earbud worn by the subject, a first spectrogram was taken of this indirect external sunlight scattered through the ear. The earbud was then removed and pointed directly at the sun, and a second spectrogram was taken of direct sunlight hitting the ear with the earbud directly facing the sun to provide a comparison graph 600, as shown in FIG. 6. The comparison graph 600 shows that sunlight at wavelengths shorter than 600 nm is greatly attenuated through the subject's ear, whereas sunlight at wavelengths longer than 650 nm is minimally absorbed through the subject's ear.

In light of the comparative graph 600 of FIG. 6, one approach to reducing the effects of sunlight on the optical response signal 111 (FIG. 1) is to choose an optical emitter 102 (FIG. 1) that emits light at wavelengths shorter than 600 nm and to choose an optical detector 103 (FIG. 1) having an optical filter that blocks light having wavelengths longer than 600 nm or that passes light within an optical bandwidth provided by the optical emitter 102 (FIG. 1). For example, a 400 to 500 nm optical emitter 102 (FIG. 1) may provide 400-500 nm optical excitation 110 (FIG. 1) to the ear region 130 (FIG. 1), and an optical detector 103 (FIG. 1) having a 400-500 nm optical filter may be used to detect the energy response signal 111 (FIG. 1) with low interference 140 (FIG. 1) from sunlight. While this method may be employed, the apparent benefits may be deceiving because the intensity of the optical scatter signal associated with physiological information may be orders of magnitude smaller than the sunlight interference—even with the combined attenuation effects of the optical filtering method and the strategic sensor module placement between the earbud housing and ear region (as shown in FIGS. 4 & 5). A better approach for attenuating the optical interference signal may be to employ optical filters within the optical detectors 103 such that the only wavelengths passing into an optical detection window may be wavelengths that are naturally attenuated by the earth's atmosphere. For example, there are several attenuation bands for sunlight well-known in the art due to the absorption of sunlight by $O_2$, $O_3$, $CO_2$, and $H_2O$ in the atmosphere. The sharp absorption peak near 763 nm in FIG. 6 is just one example. Thus, a novel design for rejecting sunlight interference may incorporate at least one optical emitter that generates optical wavelengths within at least one sunlight attenuation band combined with at least one bandpass-filtered optical detector, incorporating at least one optical bandpass filter to pass only wavelengths falling within this attenuation band.

Sunlight is quite powerful and intense, and any sunlight reaching an optical detector 103 (FIG. 1) may completely saturate the detector 103 and make it virtually impossible to extract a physiological signal from the optical scatter signal 111 (FIG. 1) coming from the human body. Unfortunately, it may be difficult to make a plastic or metal earbud housing light-tight under standard commercial manufacturing processes. For example, most commercial audio headsets include a housing made of plastic, and this plastic may be molded to include clamshells for assembly. Furthermore, commercial earbuds may be composed of multiple separate pieces that must be aligned and snapped together or adhesively attached. However, the longer wavelengths of sunlight, especially IR light, can leak through such plastic material, the clamshell regions of the plastic housing, or the bordering regions between separate plastic pieces. Furthermore, many audio headsets require openings in the material between the earbud housing and audio speaker cavity such that sound can travel freely between the tympanic membrane and the audio speaker. Sunlight may also travel between these small openings and undesirably reach the detector 103. Sunlight scattering from unwanted openings in the plastic enclosure may scatter within the clamshells of the enclosure and reach the optical detector 103.

Figure 7:
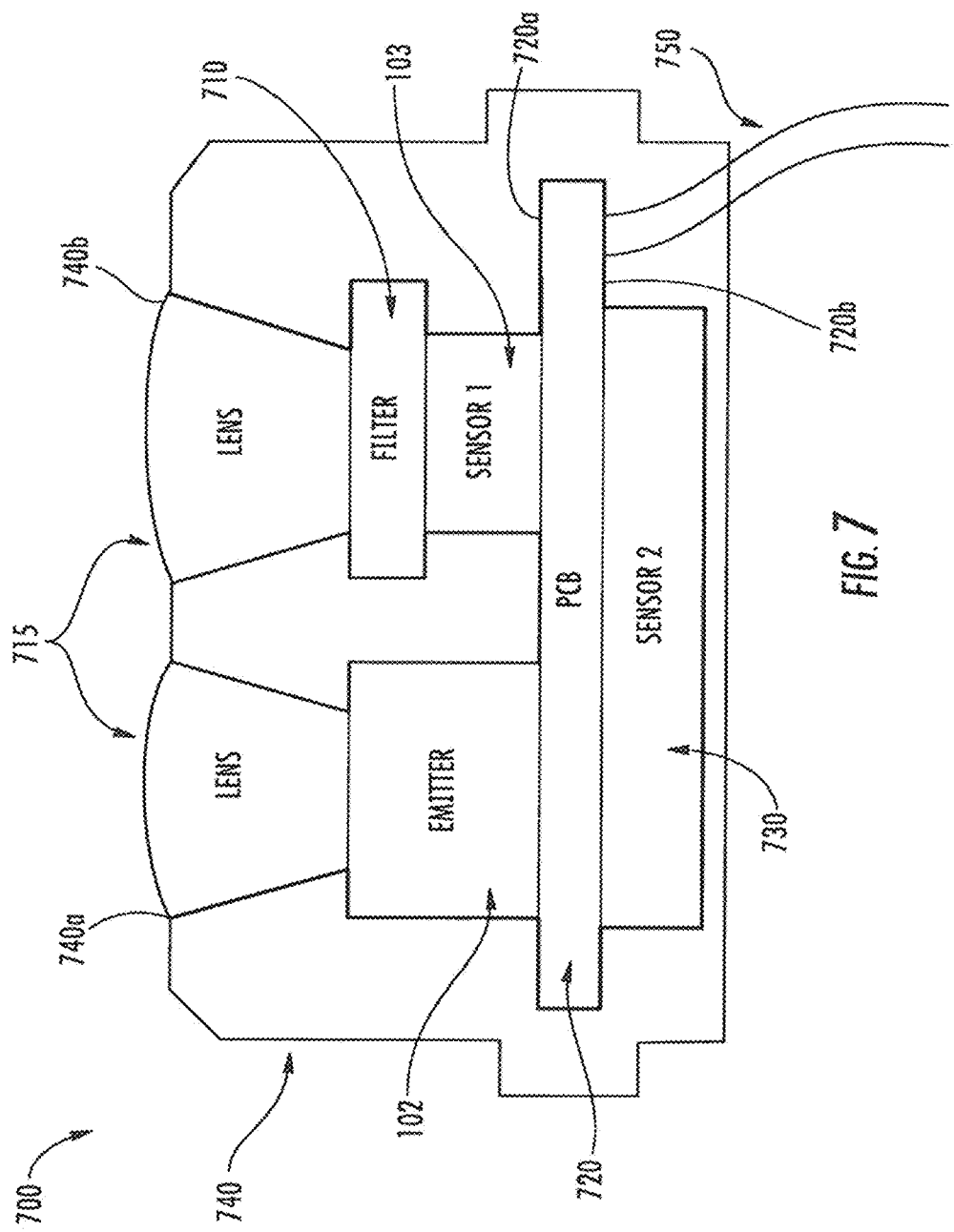
FIG. 7 illustrates a sensor module with a convex lens configuration, according to some embodiments of the present invention.

According to some embodiments of the present invention, a sensor module 700 with an overmolded design, as shown in FIG. 7, may be employed to remedy the problems associated with sunlight leaking towards the optical detector 103. In this design, an overmold layer 740 surrounds the components of the sensor module 700 to prevent light leakage into any spot along the periphery of the sensor module 700. The overmold layer 740 comprises a light-opaque material surrounding the optical emitter 102 and optical detector 103 such that the optical emitter 102 and optical detector 103 are not in direct optical communication with each other. The light-opaque material of the overmold layer 740 may include a first aperture 740*a* in communication with the optical emitter 102, and a second aperture 740*b* in communication with the optical detector 103. Thus, the only device regions having access to outside light may be the regions of the optical emitter 102 and detector 103, but these may be covered by at least one optical filter 710 tuned to a wavelength region of interest. If utilized, the wavelength pass-band of an optical filter covering the emitter 102 should be tuned to the emitter wavelength band so that all other light is blocked. If utilized, the wavelength pass-band of the optical filter 710 covering the detector 103 should be tuned to at least one wavelength band associated with the optical scatter 111 (FIG. 1) of interest from the medium 130 (FIG. 1) so that all other light is blocked.

In some embodiments of the present invention, an optical filter for the emitter 102 and detector 103 may be the same filter, such as may be the case for optical scatter 111 (FIG. 1) detection by the detector 103 where all light other than the emitter light of interest may be blocked by the filter 710. According to some embodiments of the present invention, the optical filter 710 covering the detector 103 is configured to block unwanted sunlight but still allow wavelengths from the optical emitter 102 to pass therethrough. In some embodiments of the present invention, the optical filter 710 over the detector 103 is configured to pass wavelengths centered around 930 nm, and the optical emitter 102 is configured to emit wavelengths centered around 930 nm. According to some embodiments of the present invention, the optical filter 710 may have a surface area greater than a surface area of the optical detector 103. In some embodiments of the present invention, the optical filter 710 overlies the optical detector 103 such that a periphery of the optical filter 710 overlaps a periphery of the optical detector 103, as shown in FIG. 7 and FIG. 8.

To guide light from the optical emitter 102 towards the skin 130 of a subject and to direct light from the skin 130 to the optical detector 103, lenses 715 may be utilized, as illustrated in FIG. 7. The lenses 715 may be physically separated lenses (as shown in FIGS. 7 and 8) or combined or conjoined lenses. In some embodiments of the present invention, there is no optical coupling between the emitter lens 715 and detector lens 715. For this reason, a barrier region may be incorporated in the case where the lenses are combined or conjoined. Separated lenses may be isolated by at least one light opaque barrier region greater than 50 μm in thickness. Light opaque plastic, rubber, metal, or polymeric material are a few examples of good choices for the light opaque region. The optical lenses 715 may be designed for the desired optical coupling between the skin/blood vessel region and the emitter 102 or detector 103. For example, a convex lens design (such as that of FIG. 7) placed over the emitter 102 may focus light onto the skin, and a concave lens design (such as that of FIG. 8) placed over the emitter 102 may diverge light over the skin region. In the other direction, a convex lens design placed over the detector 103 may capture more light over a broader region and direct that light towards the detector 103, whereas a concave lens may collimate light towards the detector 103.

The optical lenses 715 may be separate from the overmold layer 740 or may be part of the overmold layer 740. For example, the overmold layer 740 may be comprised of material that is transparent to light 110 (FIG. 1) coming from the emitter 102. In such case, the lenses 715 may integral with the overmold layer 740. In other cases, the optical lenses 715 may be comprised of different material than the overmold layer 740, such that the lenses 715 may fit within the overmold layer 740 and be matingly engaged with the overmold layer 740.

As shown in FIGS. 7 and 8, the emitter 102 and detector 103 may be integrated within a circuit board 720 assembly, such as a printed circuit board (PCB) assembly. The PCB board 720 may have opposite first and second sides 720a, 720b, with at least one optical emitter and optical detector adjacent to each other on the first side 720a, and with at least one secondary sensor 730 on the second side 720b. The secondary sensor 730 may be integrated within the PCB 720 for sensing another parameter. In one particular embodiment, the secondary sensor 730 may serve as a motion/position sensor 104 (FIG. 1). Connections or wiring 750 may be used to connect the sensor module 700 to another apparatus, connector, PCB, circuit, or the like. For example, electrical wiring or fiber optic cables may be overmolded such that sunlight cannot pass through the interface between the wires/cables and the overmold layer 740.

Another benefit of the overmolded design of FIGS. 7 and 8 is that it may also provide resistance to water, humidity, sweat, wind, and other environmental interferants. For example, an overmolded plastic design around the emitters 102 and detectors 103, combined with overmolded or glued lenses 715, may at least partially encapsulate the emitters 102 and detectors 103 and hence at least partially isolate these devices from the environment.

Figure 9B:
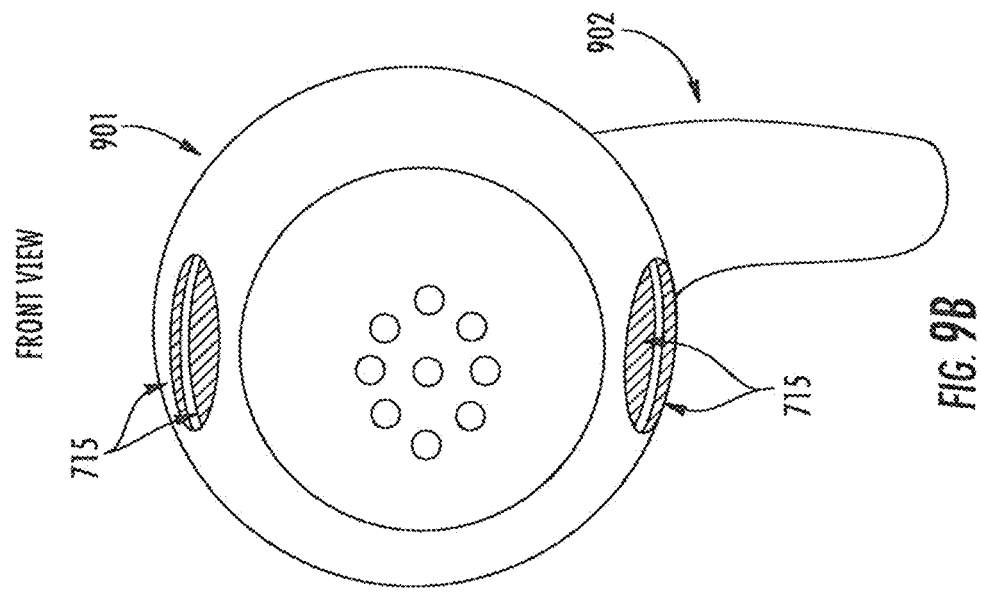
FIG. 9B is a front perspective view of the earbud monitor of FIG. 9A.
Figure 9A:
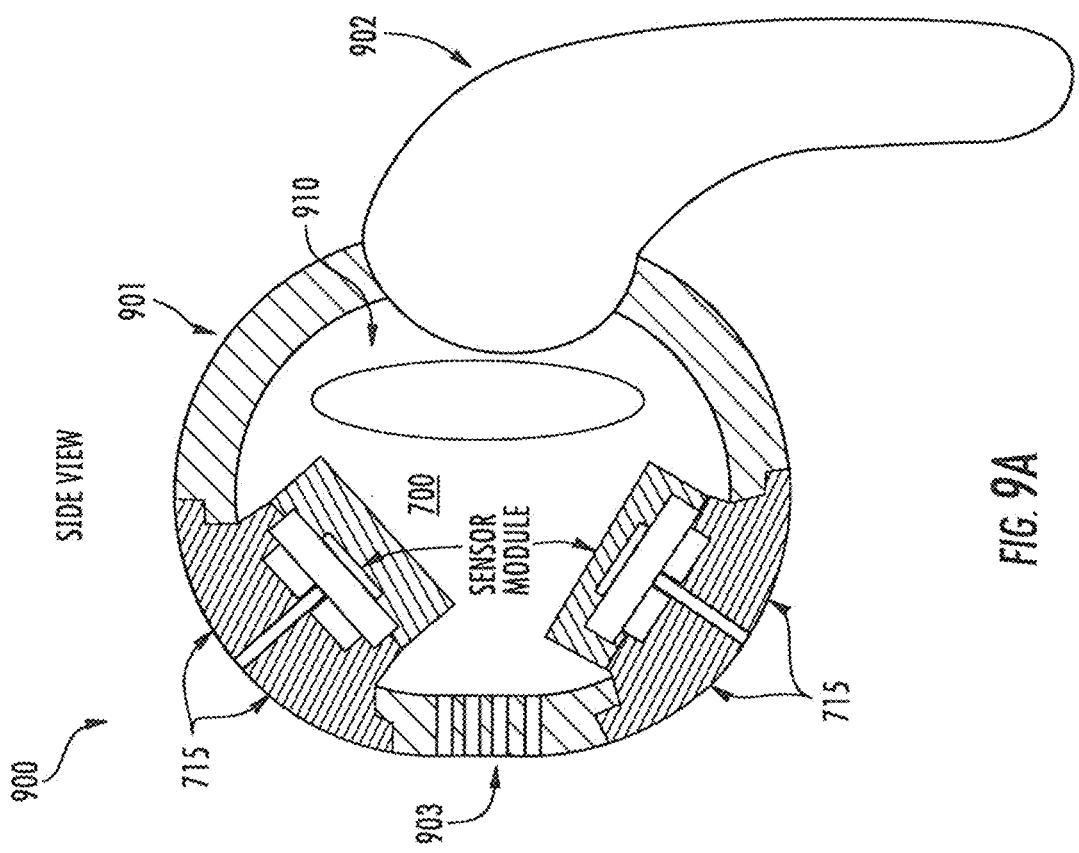
FIG. 9A is a rear perspective view of an earbud monitor, according to some embodiments of the present invention.

FIGS. 9A and 9B illustrate an environmentally protected earbud 900 that can incorporate overmolded sensor modules 700, 800, according to some embodiments of the present invention. In the illustrated embodiment, at least two sensor modules 700 are shown to emphasize that multiple sensor locations can be used, as long as the sensor modules 700 are configured to direct energy towards the ear and detect the energy response from the ear. Additionally, having multiple sensor modules 700 located around the earbud housing 901 may help with: a) making the environmentally protected earbud 900 work uniformly well on a variety of persons having a variety of differing ear physiology and/or b) enabling additional sensor functionality, such as the ability to sense blood gas levels, blood metabolite levels, pulse pressure, blood pressure, glucose, and a variety of other physiological metrics or analytes. At least one supporting arm 902 may be connected to the earbud housing 901 to support a wire, electrical connections, and/or provide additional support around the ear. For example, a supporting arm 902 may be used to house wires or wrapped around the ear to further support the earbud housing 901 within the ear.

In some embodiments of the present invention, an additional optical filter (e.g., 710, FIGS. 7 and 8) may be utilized that serves (or also serves) as an attenuation filter, such as a "neutral density filter", gelatin filter, opaque material, or other optical attenuation filter or filtering materials. In one embodiment, an optical filter 710 may serve as both an optical wavelength filter and an attenuation filter. Because sunlight is so powerful, it may be beneficial to reduce sunlight interference as much as possible, even if that means also reducing the amount of optical scatter 111 (FIG. 1) of interest from the medium 130 (FIG. 1). To offset this unwanted reduction in optical scatter 111, the intensity of the optical emitter 102 may be increased to increase the ratio of physiological optical scatter 111 from blood vessels with respect to unwanted sunlight.

Figure 10:
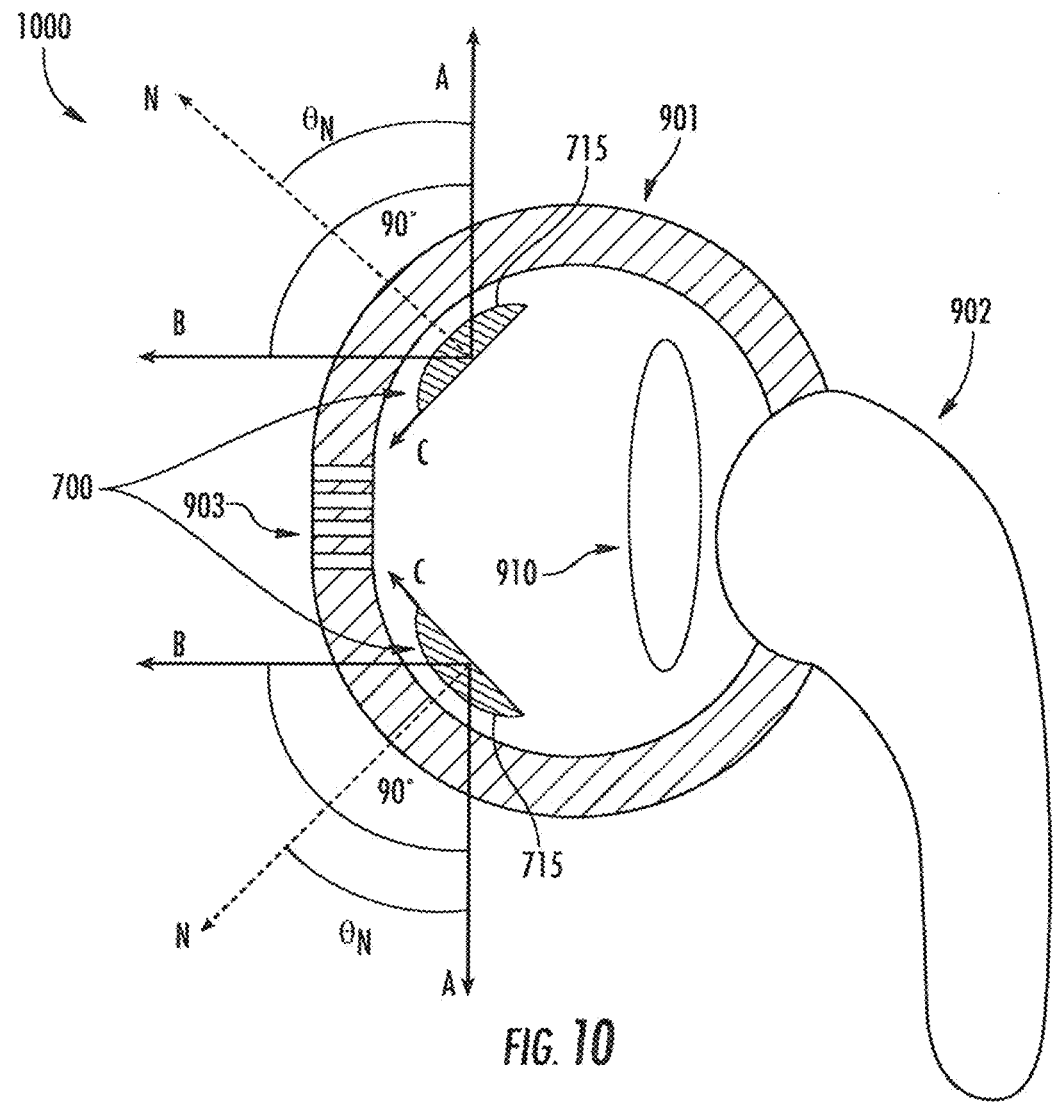
FIG. 10 illustrates the angling preferences for sensor modules within an earbud monitor, according to some embodiments of the present invention.

The angling of the sensor modules 700, 800 (FIGS. 7 and 8) within the earbud housing 901 may be designed to direct light towards the ear and detect light from the ear while rejecting as much environmental light (such as sunlight) as possible. As shown in FIG. 10, angling the normal "N" of the lens 715 between the perpendicular lines "A" & "B", where "A" is perpendicular to earth ground and "B" is parallel to earth ground, would help achieve this goal. Phrased another way, the angle "$\theta_N$" between "N" and "A" or "N" and "B" would preferably be less than 90°. The lens 715 placement and angle does not obstruct the audio cavity between the speaker 910 and the earbud housing opening(s) 903, which helps couple light to the ear canal. For this reason, in some cases, angle "$\theta_N$" approximating 45° may be utilized for limiting the sensor module 700 exposure to outside light while also limiting the obstruction of the audio cavity by the sensor module 700.

The lenses 715 described herein may be comprised of any material that is at least partially transparent to the wavelengths of light generated by the emitter 102 and/or the desired wavelengths of light detected by the detector 103. In some embodiments of the present invention, the lenses 715 are completely transparent to the light of interest, but in other embodiments of the present invention the lenses 715 may be configured to diffuse, attenuate, disperse, or redistribute light uniformly across the lens. For example, a lens 715 incorporating diffusing material, placed over the emitter 102, may help spread more light from the emitter more uniformly across the area of the lens such that a broader physiological region may be excited by optical radiation. Similarly, a diffusing lens configuration placed over the detector 103 may help detect light from a broader area of the body and direct that light towards the detector 103. Some plastic materials contain scattering centers or materials that tend to scatter light. For example, silicones may be used to diffuse light in a lens. Partially opaque lenses may also be used to provide diffusion or internal scattering of light within a lens. Additionally, roughened surfaces, such as roughened plastic or glass, may encourage diffuse optical scatter without greatly attenuating the intensity of light. Other methods of creating optical diffusion or scattering in light-guiding materials such as lenses may be utilized.

Figure 11:
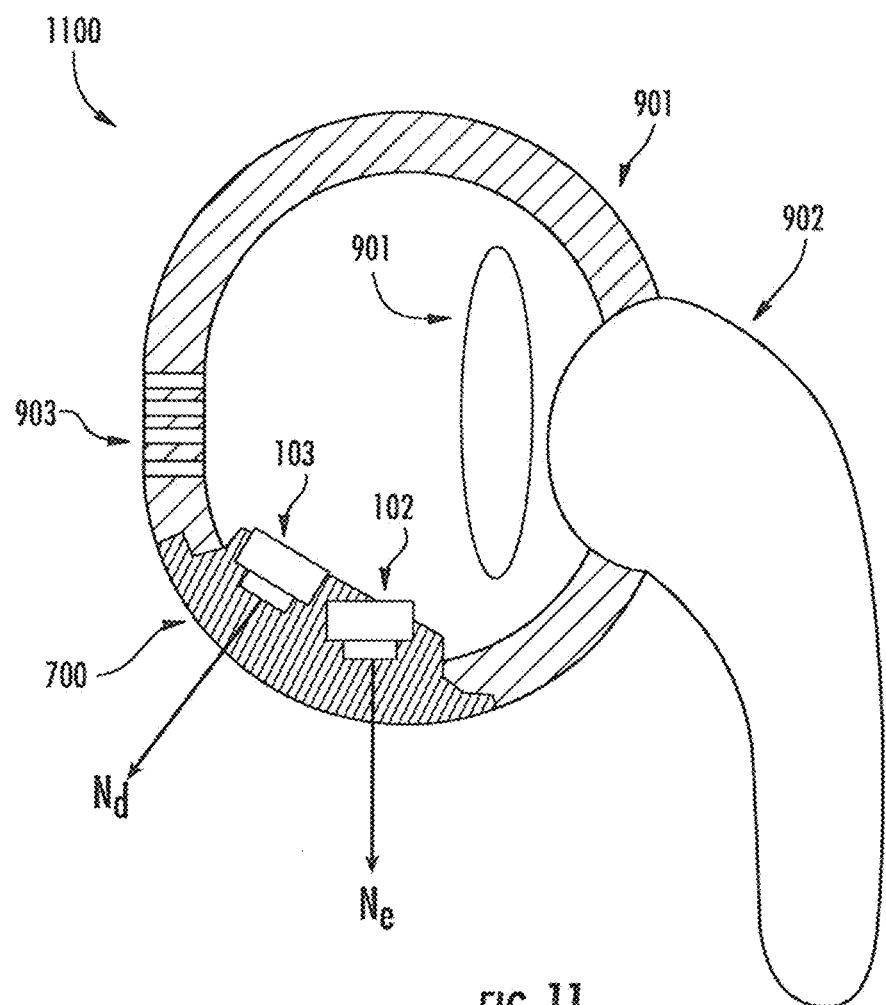
FIG. 11 illustrates an earbud monitor, according to some embodiments of the present invention, that increases physiological signal and reduces environmental noise.

The angled emitter-detector earbud configuration 1100 of FIG. 11 may be employed to maximize the collection, by the detector 103, of the scattered light response 111 (FIG. 1) related to physiological conditions and to minimize the collection of the unwanted scattered light response 111 (FIG. 1) not related to physiological conditions. Angling the emitter 102 with respect to the detector 103 can prevent unwanted light generated by the emitter, such as that scattered by the outer surface of the skin, from reaching the detector 103. While at the same time, desired light that is guided into the blood vessels, scattered within physiological material 130, and coupled into the detector 103 may contain desired optical information associated with physiological changes. The higher the angle between the emitter an detector, the less the intensity of optical energy that may be detected by the detector 103. However, the higher the angle, the higher the ratio of desired optical signal to undesired optical signal. In some embodiments of the present invention, the angle between the normal "$N_e$" of the optical emitter and the normal of the optical detector "$N_d$" is between 0° and 90°. The position of the emitter 102 and detector 103 as shown in FIG. 11 may be reversed, providing the same effect. However, the optical emitter 102 may be located near the portion of the ear having a higher density of blood vessels, such that the optical energy will be more greatly modulated by physiological conditions (such as blood flow, blood gas levels, and the like) and such that the optical energy detected by the detector 103 will be more indicative of physiological conditions and less indicative of unwanted optical scatter (such as skin reflectance) or motion-related scatter (such as motion caused by running, jogging, or talking).

It should be noted that the angling of the emitters 102 or detectors 103 in the right location within not only the earbud housing 901, but also within the ear itself, may be critical for blocking out sunlight 140 while still generating a strong enough physiological signal from the ear region. For this reason, the earbud 1100 (FIG. 11) may also employ at least one earpiece fitting, or other additional mounting support, to keep the earbud in place within the ear and/or keep the sensor module 700, 800 directed at the right angle within the ear. Several types of earpiece fittings are well known in the art, such as: ear hooks, ear clips, ear pads, ear loops, concha support, headbands, and the like. A specific example of a supportive earpiece fitting, a concha support that loops around the concha-helix area of the ear, is shown in the earbud 404 of FIG. 4. In some embodiments of the present invention, the earpiece fitting supports the earbud within the ear while also placing pressure against the earbud to keep the sensor module in place, away from outside light interference.

At least part of the earbud housing 901 (FIG. 11) or sensor module 700 (FIG. 11) may comprise a soft material which deforms when inserted within the ear and that facilitates retention of the earbud within the ear. For example, the shape of earbud housing 901 shown in FIG. 11 may facilitate retention of the earbud 1100 within the ear because it may be shaped to mate or engage with the concha or outer ear canal of the ear. Furthermore, if part of the earbud 1100 comprises a soft material, such as soft plastic, polymer, silicone, or rubber, the material may deform when the earbud 1100 is inserted within the ear such that this part of the earbud 1100 mates or engages with the ear. The sensor modules of FIGS. 7 and 8 may be integrated within the earbud housing 901, such that at least a portion of the housing 901 may comprise optically transmissive material to allow light to move from the emitter 102 to the ear region or from the ear region to the detector 103. The soft deforming material may be adjacent to the optically transmissive material or may comprise at least part of the optically transmissive material itself. For example, the lenses 715 of FIG. 9 may be comprised of optically transparent material that is also soft, such as silicone or transparent plastic, polymer, rubber, or the like. In another embodiment, a second layer of soft, yet transparent, material may cover the lenses 715.

Figure 12A:
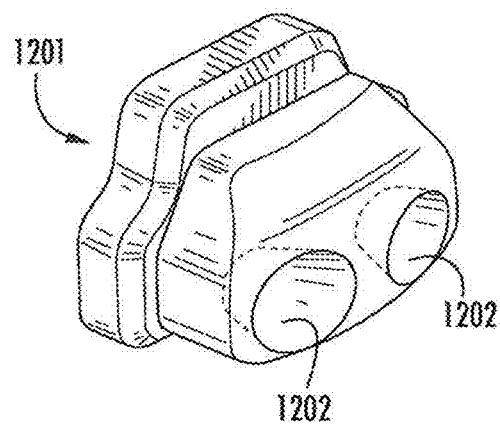
FIG. 12A is a perspective view of a sensor module, according to some embodiments of the present invention.
Figure 12B:
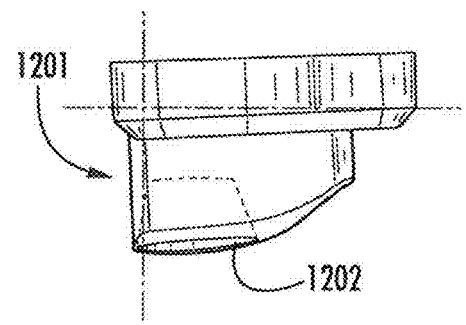
FIG. 12B is a side view of the sensor module of FIG. 12A.
Figure 12C:
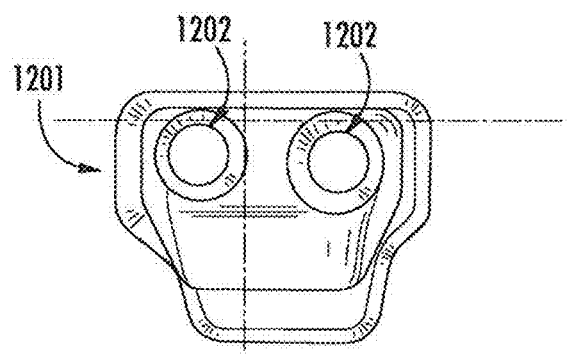
FIG. 12C is a top plan view of the sensor module of FIG. 12A.
Figure 13C:
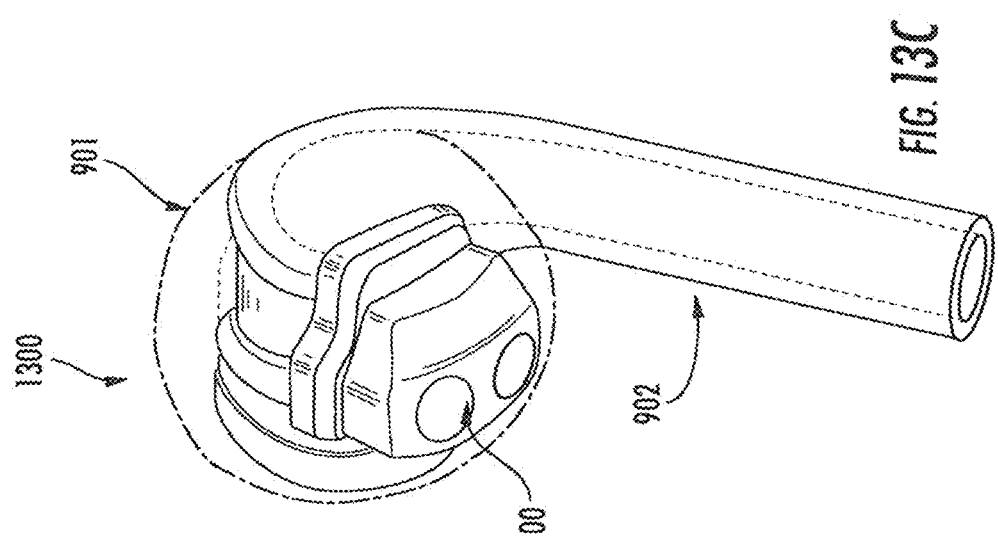
FIG. 13C is a side perspective view of the earbud of FIG. 13A.
Figure 13B:
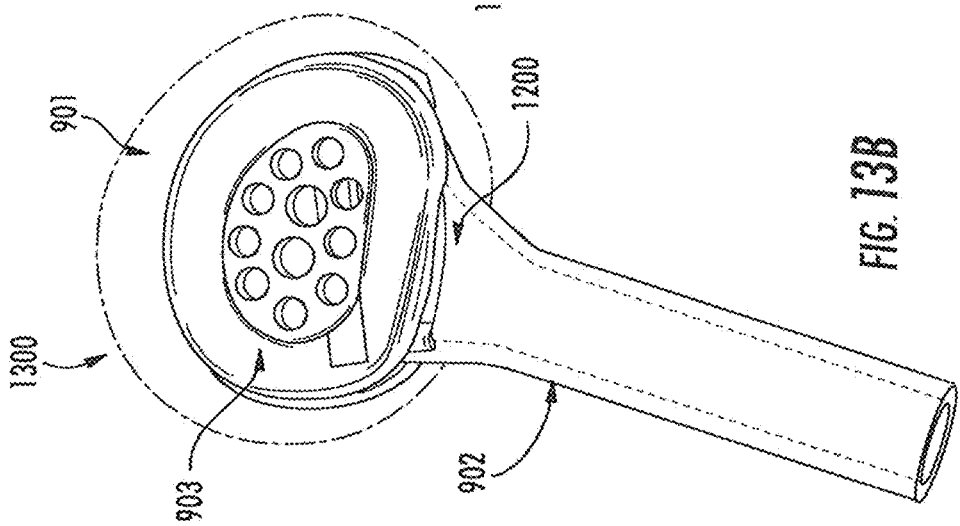
FIG. 13B is a front perspective view of the earbud of FIG. 13A.
Figure 13A:
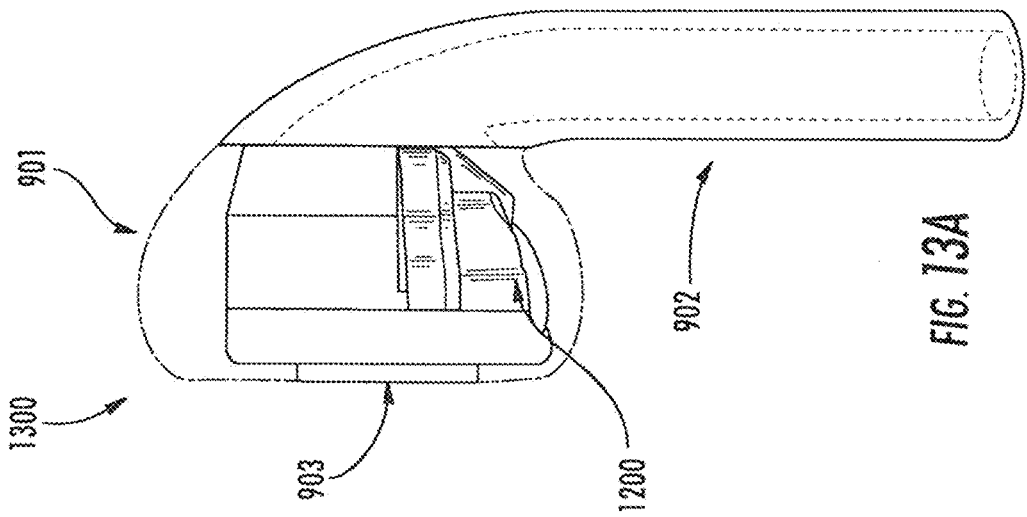
FIG. 13A is a side view of an earbud comprising the sensor module of FIGS. 12A-12C, according to some embodiments of the present invention.

An exemplary overmolding configuration of a sensor module 1201 is illustrated in FIGS. 12A-12C. The sensor module 1201 is shown without an emitter, detector, or lenses, but rather with recesses/apertures 1202 showing where lenses may be located. Exemplary dimensions are also presented in FIG. 12. In some embodiments of the present invention, dimensions are on the order of millimeters or less, such that the sensor module 1201 can fit within a small-sized earbud without obstructing, or minimally obstructing, the audio cavity. In the illustrated embodiment, an emitter and detector to be used with the sensor module 1201 can be arranged in a line that is parallel with the antitragus. This arrangement is illustrated in FIGS. 13A-13C. However, embodiments of the present invention are not limited to any particular set of dimensions or to any shape or configuration.

Figure 14:
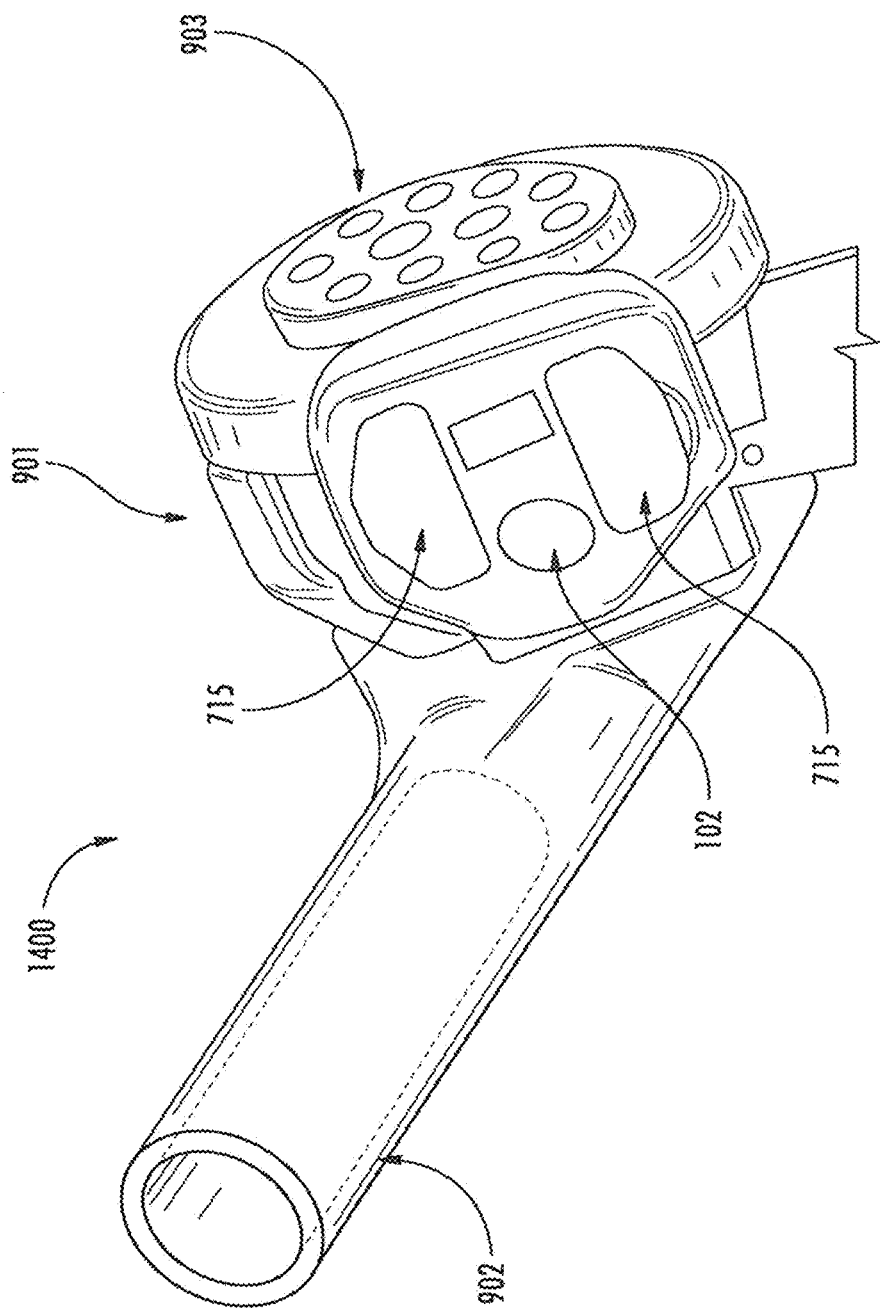
FIG. 14 is a bottom perspective view of a multi-detector earbud, according to some embodiments of the present invention.

FIG. 14 illustrates a multi-detector earbud 1400, similar to the earbud 1300 of FIGS. 13A-13C, but where two separate optical detectors (not shown) are covered by two separate optical lenses 715. An optical emitter 102 is located between the two optical lenses 715. Employing multiple optical detectors may provide several benefits: 1) more scattered light collection, providing stronger signal strength, 2) additional information on scattered light collection for improving physiological assessments, 3) light collection at different wavelengths for measuring blood constituents, pulse pressure, skin, color, and the like, and 4) other benefits. For example, light entering the ear may scatter throughout several blood vessels, and without multiple detectors, signal information may be lost. Additionally, blood flow scatter collected from the front of the ear may be more indicative of blood flow through the carotid artery system, whereas blood flow scatter collected from the back of the ear may be more indicative of the capillary or venous system. The difference between these two signals may be processed with algorithms to generate an assessment of pulse pressure, blood pressure, cardiac output, and the like. Lastly, collecting light at different wavelengths, and processing these signals collectively, can be used to generate assessments of blood gas levels, such as blood oxygen ($SpO_2$) and carbon dioxide ($SpCO_2$), blood hemoglobin types and levels, or other blood constituents and their respective concentration levels. Multiple wavelengths may be generated by a signal multiwavelength optical emitter, multiple optical emitters, optically filtered optical emitters, or the like. In such case, multiple optical emitters 102 may be located between the two optical filters 715.

FIGS. 15A-15B show a multi-detector earbud 1500, where two separate optical detectors 103 are covered by two separate optical lenses, at least one optical emitter is covered by at least one optical lens, and where the emitter 102 and detector 103 configuration is oriented perpendicularly to the antitragus (as that shown in FIG. 11). In FIGS. 15A-15B, the optical detectors 103, emitters 102, and lenses are not readily visible as they are surrounded, at least in part, by an optical coupling area 1510. The lenses (not shown) may cover each separate emitter 102 and detector 103 as shown in FIGS. 7 and 8. Note that in this configuration, the emitter-detector module 700, 800 of FIGS. 7 and 8 is oriented towards the back of the ear (near the back of the head). This arrangement may serve two purposes: 1) sunlight may be further blocked from reaching the detectors 103, as the back of the ear may serve as a shield and 2) there may be less motion artifacts convoluting the desired blood flow signals, as the detectors 103 may be oriented away from mouth-motion-prone areas located near the front of the ear. Another feature of the earbud 1500 of FIGS. 15A and 15B is that an optical coupling area 1510 is located on top of the optical emitter 102 and surrounding (but not covering) the optical detector 103. This optical coupling area 1510 may help diffuse, scatter, and/or guide light from the optical emitter to couple with a broader area of the ear region. Having a broader coupling area may help excite more regions of the ear with optical energy 110 (FIG. 1) and reduce the chance that the optical energy may miss important blood vessels, which may be located in different regions for different persons. Thus, such a design may promote a more universal design for a biometric earbud. Without an optical coupling area 1510, the optical energy 110 from the optical emitter(s) 102 may miss blood vessels in different persons due to physiological differences that may exist between different people. Alternatively, the optical coupling area 1510 may be configured to cover the optical detector 103 area and not the optical emitter 102 area, such that more light is guided from different regions of the ear and coupled into the detector 103. Alternatively, a plurality of optical diffusion areas may be configured to cover the emitter 102 and detector 103 separately.

The material selection for the optical coupling region 1510 may be any type of optically transmissive material. For example, a plastic, rubber, silicone, or other soft, moldable material may be used. In some embodiments, the material may intentionally contain scattering centers or may contain partially opaque regions to promote optical scatter and generate a uniform, diffuse optical beam across the optical coupling area 1510. In some embodiments, the material may be roughened, as with roughened plastic or glass, to generate scattering centers.

Figures 16A, 16B:
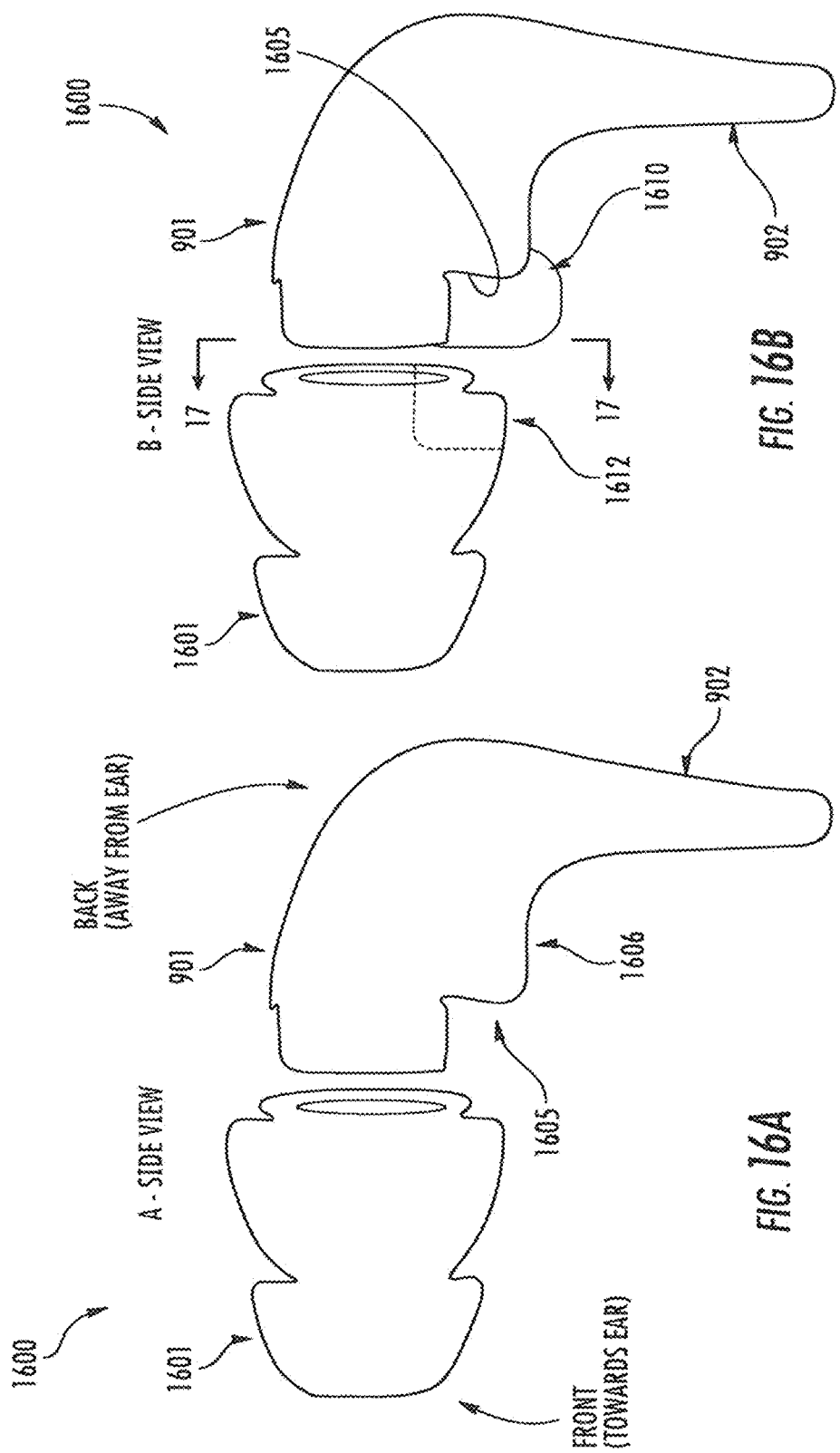
FIG. 16A is an exploded side view of a headphone and a replaceable/interchangeable earbud tip, according to some embodiments of the present invention.
FIG. 16B is an exploded side view of a headphone and a replaceable/interchangeable earbud tip, according to other embodiments of the present invention.

FIGS. 16A-16B illustrate an exemplary headphone 1600 having a replaceable/interchangeable earbud tip 1601. An interchangeable tip 1601 can provide the benefit of allowing larger or smaller tips on the end of the earbud housing 901 to accommodate larger or smaller ears. A typical commercially available headphone structure may look like the embodiment illustrated in FIG. 16A. In FIG. 16B, an optical sensor module 700 is integrated into the bottom of the headphone housing 901, in the region near the antitragus, in a form-fitted shape 1610 designed to make contact with the antitragus region. However, this may increase the size of the housing by a few millimeters in multiple dimensions. For this reason, the interchangeable earbud tip 1601 may be modified with a form-mating region 1612 to mate with the form-fitted region 1610 and thus accommodate the change in size imposed by the optical sensor module 700.

According to other embodiments of the present invention, optical coupling and waveguiding are incorporated into a headphone. For example, at least one emitter (not shown) and at least one detector (not shown) may be integrated into a sensor module and stationed within an earbud housing 901 of the headphone 1600 of FIG. 16A without the addition of a form-fitted shape 1610 (FIG. 16B) or mating region 1612 (FIG. 16B). Optical excitation of the ear region can be generated by guiding light from an emitter to an interchangeable earbud tip 1601 and into the ear region or by guiding scattered light from the ear region into the earbud tip 1601 and into an optical detector. To couple light from an optical emitter into the earbud tip 1601, the optical emitter may be positioned in the earbud face 1605 region to direct light towards the earbud tip 1601. In some embodiments of the present invention, the optical detector is positioned in the earbud bottom region 1606 (FIG. 16A) to receive light from the bottom of the ear. Similarly, to couple light from the earbud tip 1601 to an optical detector, the detector may be located in the front earbud face region 1605 (FIG. 16A) to receive light from the earbud tip 1601.

In some embodiments of the present invention, the optical emitter is positioned within the earbud bottom region 1606 (FIG. 16A). Using the interchangeable earbud tip 1601 as a light guide, the earbud material is made of at least partially transparent materials, which are transparent to the wavelength of interest. Additionally, an earbud material having a higher index of refraction than air may be used so that more light is guided along the earbud tip 1601 and less light is scattered away from the earbud tip 1601. Additionally, intermediate regions between the earbud face 1605 and the earbud tip 1601 may be utilized in order to promote optical coupling between the two regions. For example, a lens (not shown) or other light guiding region may be placed over the emitters or detectors to promote this optical coupling.

Figure 17:
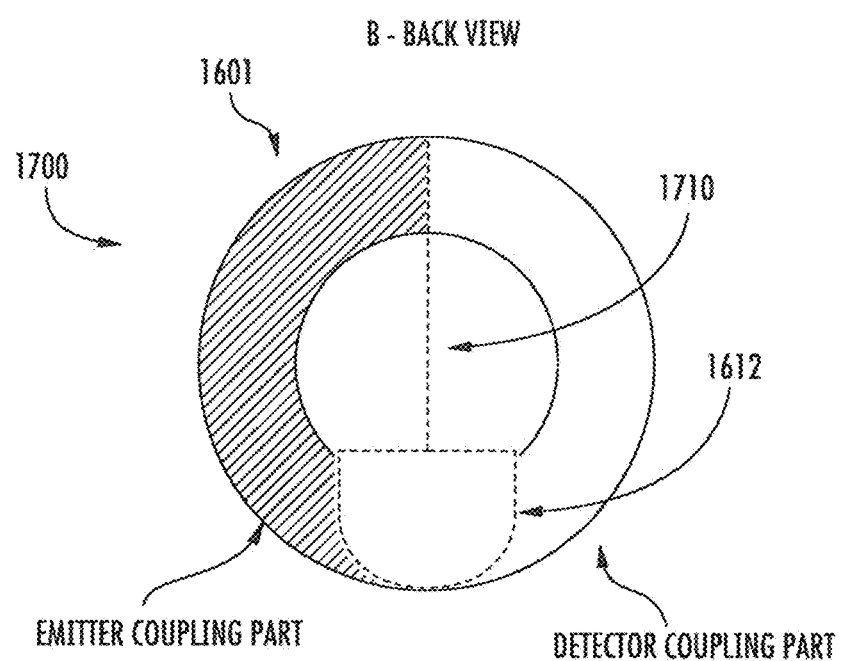
FIG. 17 is a rear view of the earbud tip of FIG. 16B taken along lines 17-17, and illustrating at least two separate parts supporting at least two separate optical paths.

Referring to FIG. 16B, in some embodiments of the present invention, emitter(s) and detector(s) may both be positioned in the earbud face 1605 region to direct light towards the earbud tip 1601. In this manner, the earbud tip 1601 may help: 1) direct light from the emitter to the ear region and 2) direct light from the ear region to the detector. However, optical scatter interference associated with light from an emitter bouncing around in, around, and about the earbud tip 1601 may convolute a desired optical scatter signal (e.g., 111, FIG. 1) associated with physiological information (such as blood flow in the ear region). To reduce this unwanted convolution of undesired optical scatter, the earbud tip 1601 may include at least two separate parts, as shown in FIG. 17. The earbud tip 1601 illustrated in FIG. 17 is separated by an optical barrier 1710, with one part coupled to the optical emitter and another part coupled to the optical detector. Each part may support at least one separate optical path isolated by at least one optical barrier 1710. For example, one part may direct light from the emitter to the ear region and another part may direct light to the detector from the ear region. The optical barrier 1710 may be any material that is partially or completely opaque to the light wavelength of interest or any interface which reduces light transmission or communication between the two earbud tip parts. For example, the earbud tip 1601 may be molded from two (or more) separate materials (plastic, rubber, silicone, and the like) separated by: 1) an opaque material (plastic, rubber, silicone, paint, and the like) or 2) at least one interface between the two (or more) separate materials. The interface may be as simple as the natural interface between the two separate materials or as complex as by specially treating the interface by heat, light, abrasion, dissolving, chemical application, or the like. A roughened interface may help scatter light away from the interface and help keep the optical paths isolated within each respective part. It is important to note that such a multi-part earbud tip design may require a mating region 1612 to help align the earbud coupling part and detector coupling part with the emitter(s) and detector(s) respectively. As a further note, this design should not be limited to the two earbud tip parts (the emitter coupling part and detector coupling part) shown in FIG. 17. In one embodiment, multiple earbud tip parts may be employed to direct light from multiple separate emitters and/or multiple separate detectors located along the earbud housing 1901. Moreover, multiple separate materials may be used in each part, such that each part may provide different optical filtering or conditioning properties. Such a design may be particularly important for multiwavelength spectroscopy of the ear region.

An exemplary filter processes samples 1910, the off/on samples 1920/1930 respectively, taken from a digitized physiological sensor signal 1911 generated by a detector (e.g., 103, FIG. 1) as shown in FIGS. 19A-19B. A pulsed emitter (e.g., 102, FIG. 1) generates a pulsed beam of light such that some samples 1920 represent signal 1911 from a detector with the emitter turned off and other samples 1930 represent signal 1911 from the detector with the emitter turned on. Both types of samples 1920 and 1930 may contain environmental noise from environmental interferants, but only emitter-on samples 1930 contain physiological information generated by the emitter energy. The digitized samples taken from detector signal 1911, provided by an ADC (e.g., 105, FIG. 1), are processed by an interference filter (e.g., 106, FIG. 1) and the output of the interference filter may be directed for further processing (represented by 107, FIG. 1).

Figure 18:
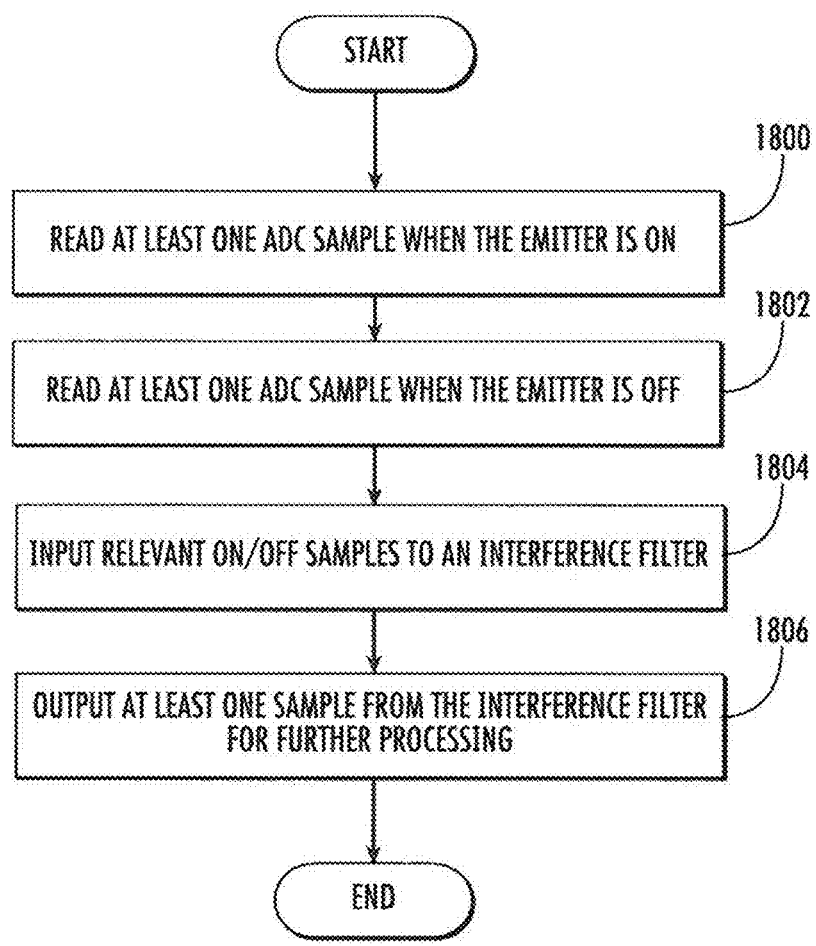
FIG. 18 is a flowchart of operations for removing environmental noise from a sensor signal, according to some embodiments of the present invention.

These operations are summarized in FIG. 18, which is a flow chart of operations for removing environmental noise from a sensor signal via an interference filter, according to some embodiments of the present invention. At Block 1800, at least one ADC sample is read when the emitter is on. At Block 1802, at least one ADC sample is read when the emitter is off. At Block 1804, relevant on/off samples are input to an interference filter. At Block 1806, at least one sample from the interference filter is output for further processing.

An interference filter (e.g., 106, FIG. 1) utilized according to embodiments of the present invention, may vary in nature and complexity. For example, an interference filter may subtract temporally neighboring emitter-off samples 1920 (FIG. 19A) from temporally neighboring emitter-on samples 1930 (FIG. 19A) and output a "subtraction" signal for further processing. In this embodiment, the subtraction may involve subtracting temporally neighboring on/off samples, averaging temporally neighboring on samples and averaging temporally neighboring off samples and then subtracting the average off samples from the average on samples, or by other approaches to subtracting off signals 1920 from on signals 1930. When choosing a subtraction approach, it is important to consider the emitter pulsing frequency and sampling approach. For example, choosing a frequency that is too low may result in unsatisfactory subtraction, as the dynamic environmental conditions between off-states 1920 and on-states 1930 may be too abrupt for the sampling frequency, such that the physiological state of interest is not properly characterized by the interference filter. Thus, the sampling frequency may need to be much higher than the Nyquist frequency required for characterizing the signal in a stationary environment. As a specific example, if an interference filter (e.g., 106, FIG. 1) is being used to remove sunlight interference (e.g., $SL_1$, $SL_2$, FIG. 3), from a photoplethysmogram 1911 (FIGS. 19A, 19B), and if the desired processed output from the final filtering is heart rate, then the Nyquist criteria for pulsing the emitter may be $2 \times f_{max}$, where $f_{max}$ is the maximum heart rate of interest, which is likely to be somewhere around 200 beats/minute (BPM) or 3.33 Hz.

However, a person running through alternating shadows may generate a sunlight interference frequency greater than 10 Hz. In such case, it may be desirable to select a sampling frequency greater than twice the sunlight interference frequency, which in this case would be greater than 20 Hz. Samples that are temporally neighboring (located close to each other in time) may be averaged in this case to help remove noise associated with unintended transients. For example, the off samples 1920 (FIGS. 19A, 19B) that come before, and/or after, a given on sample 1930 (FIGS. 19A, 19B) may be averaged and then that average may be subtracted from the on sample 1930 (or average of the on samples), and this final result may be passed along for further processing.

As another example, a batch of data may be defined to consist of: 1) a set number of on/off optical detector samples, for instance 6 interleaved on/off samples, 2) a set number of motion sensor samples, for instance 3 samples (one for each on/off optical sample), and 3) a time delay. The time delay may be adjusted to generate the desired batch rate or batch frequency. The 6 on/off optical samples may be input to a multi-tap filter, for instance an M-tap weighted sum filter, and the output may be defined as 1 output per batch for the interference filter. If the optical on/off samples are extended to fill the whole batch period by "N" samples, then the decimation factor is "N", and the effective sample rate is N*batch rate. The parameters for adjustment in this filter may then be N and M, where M is the number of taps in the filter. The batch rate may be chosen to avoid aliasing of interfering harmonics from the desired physical condition monitored, such as the heart rate. For example, batch rate may be chosen as 10*HRmax, where HRmax is the maximum heart rate to be measured. The batch rate may dominate the MIPS (million instructions per second) used by a signal processor, such as a DSP (digital signal processor), since it affects the spectral transform of the desired output signal. In this filtering embodiment, to minimize aliasing from interfering sunlight-shadow changes on the desired heart rate output signal (especially for running or cycling through shadows), a increasing the N and/or M may be preferred.

Another example of a batch may include nine (9) optical segments per batch: off-on-off-on-off-on-off-on-off. Within a given batch, the average of the "off" samples may be subtracted from the average of the "on" samples, providing one output per batch. This would generate a decimation factor of nine (9). Additional batch configurations and on/off configurations may be used in this invention.

It should be noted that the modulated light 110 may be pulsed completely on or completely off, or it may be pulsed partially on or partially off. In some embodiments, for example, the modulated light may be sinusoidal. A benefit of complete on/off pulsing is that it may better-facilitate the signal processing methodologies outlined herein for attenuating environmental noise and motion-coupled environmental noise from one or more output signals.

Figure 20:
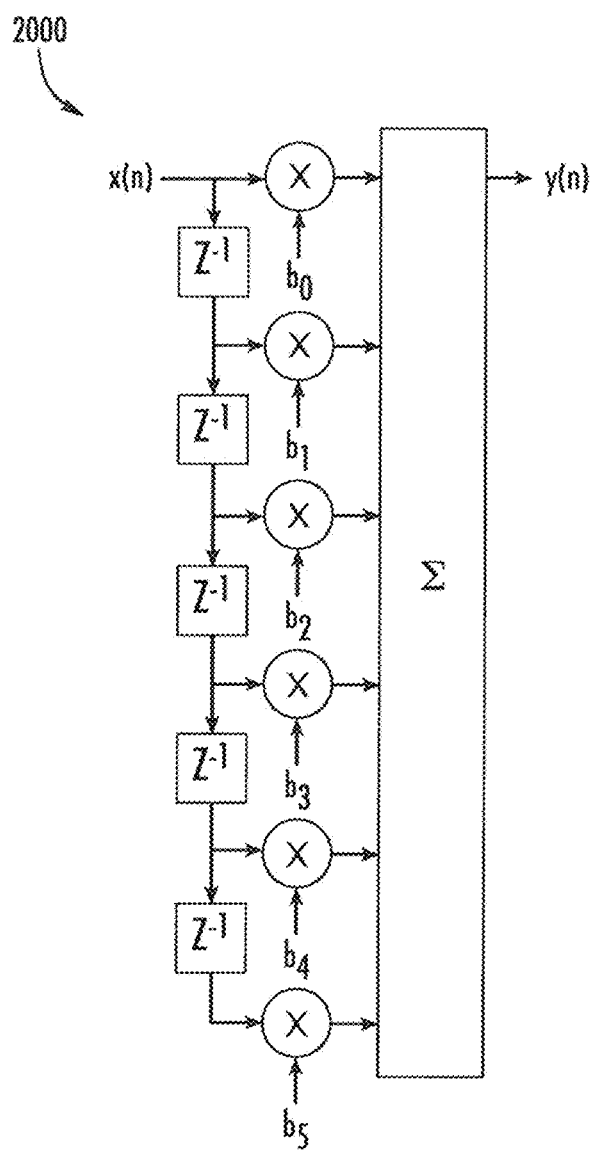
FIG. 20 is a schematic illustration of an interference filter, according to some embodiments of the present invention.

A finite impulse response (FIR) version of an interference filter, according to some embodiments of the present invention, levering the pulsed-emitter on/off sampling rate, is presented in FIG. 20 and identified as 2000. The illustrated interference filter 2000 employs a delay of "n" samples according to $Z^{-n}$. Coefficients in the filter "$b_n$" allow multi-tap filtering. Pulsing an emitter (e.g., 102, FIG. 1) and selectively sampling on/off signals, as described herein, may modulate the physiological signal to a higher frequency. Thus, the output y(n) of the interference filter 2000 may be decimated to demodulate the output back into the baseband. A specific example of a decimation-by-2 algorithm may reject odd-numbered samples such that the decimated signal, w(m), may be described by even-numbered samples according to w(m)=y(2*m).

Figure 21:
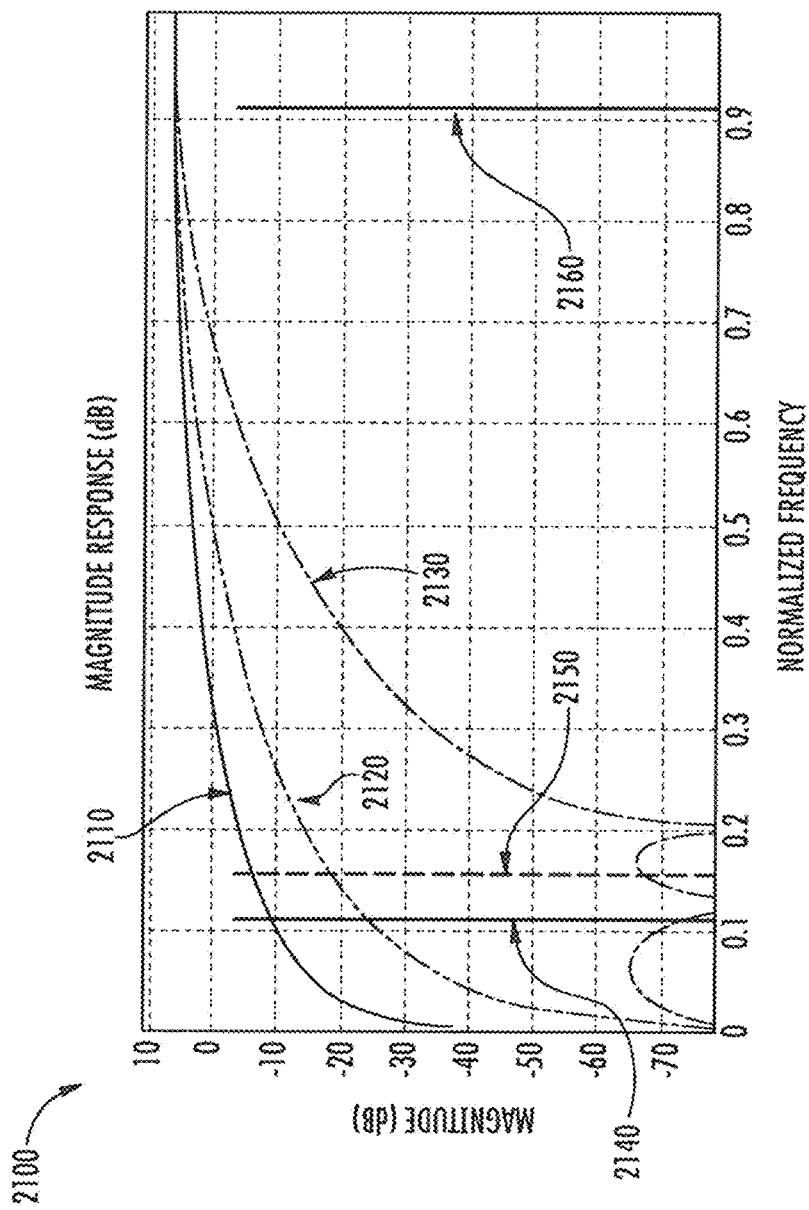
FIG. 21 is a graph that illustrates magnitude responses for several interference filters, according to some embodiments of the present invention.

Examples of filters embodying the interference filter 2000, for removing sunlight interference from a PPG signal 1911 (FIGS. 19A, 19B) to extract heart rate, according to embodiments of the present invention, are illustrated in the plot 2100 of FIG. 21. The plot 2100 presents the magnitude response (in dB) for each interference filter vs. normalized frequency (1=Nyquist). Also shown in FIG. 21 is a representation of the modulated heart rate 2160 modulated by the emitter on/off sample rate, the demodulated heart rate 2140 demodulated by decimation, and the interference frequency associated with dynamic sunlight noise 2150. As a specific example for the previously described "subtraction filter" 2110, the FIR coefficients may be [b1 b2]=[1 −1]. A filter 2120 for subtracting the temporally neighboring off-samples 1920, coming before and after a given on-sample 1930, may employ coefficients of [−0.05 1 −0.5]. A filter 2130 using multiple on/off samples may employ coefficients of [−0.07 0.3 −0.6 0.6 −0.3 0.07].

It should be noted from FIG. 21 that interference filter 2000 may reject more unwanted sunlight than less complex filters. Because the dominant sunlight noise frequencies 2150 may be located at lower frequencies, and because the modulated heart rate signal frequency 2160 may be located at a much higher frequency, most or all of the sunlight noise 2150 may be rejected by the interference filter 2130. Then through demodulation in further-processing (e.g., 107, FIG. 1), the heart rate signal may be returned to the baseband so that real-time heart rate may be extracted.

An interference filtering method, according to some embodiments of the present invention, may employ a motion/position sensor (e.g., 104, FIG. 1) to further remove interference from a desired physiological signal (e.g., 109, FIG. 1). For the case of sunlight interference (e.g., 140, FIG. 1) on an earbud sensor module (e.g., 207, FIG. 2), outdoor sunlight may more strongly illuminate an ear and detector 103 in the sensor module 207 than the emitter 102 in the sensor module 207. While an interference filter (e.g., 2130, FIG. 21) may effectively remove the baseband frequencies of this interference, harmonics caused by motion-induced sunlight noise may dominate the digitized signal near the frequencies of the modulated desired information (e.g., 2160, FIG. 21). The step rate of a person running or jogging may be the strongest component of this interference. Moreover, because a person running or jogging may be moving through varying sunlight intensity, the interference signal may be a convolution of motion-coupled-sunlight changes in time. A technique for removing sunlight interference, according to some embodiments of the present invention, utilizes a motion or position sensor (e.g., 104, FIG. 1), such as an inertial sensor, accelerometer, pedometer, gyroscope, microelectromechanical sensor, capacitive sensor, inductive sensor, optical motion sensor, or the like. The step rate may be measured as the peak frequency in the spectrum of the signal coming from motion/position sensor 104 or as the frequency of the spectral peak of the signal coming from the motion/position sensor 104. For example, the processed spectrum may employ differentiation or integration to generate a processed motion/position signal, and the peak frequency of this processed spectrum may be more indicative of the step rate. Harmonics and aliased harmonics of the step rate may determine the frequencies of interference to ignore in the desired-information spectrum. For example, the emitter pulse rate minus eight times the step rate (aliased 8th harmonic) may be the frequency of strong interference in the frequency space of the modulated heart rate (e.g., 2160, FIG. 21), and frequencies within a pre-determined range may be set to zero in the desired-information spectrum.

It should be noted that a motion/position sensor (e.g., 104, FIG. 1) utilized in accordance with some embodiments of the present invention may come from a broad range of sensors: inertial sensor, accelerometer, pedometer, gyroscope, microelectromechanical sensor, capacitive sensor, electrical sensor, inductive sensor, optical motion sensor, or the like. This is because many types of sensors may be either intentionally or unintentionally sensitive to motion and/or position. However, in some embodiments of the present invention, a sensor 104 (FIG. 1) and/or processing algorithm are utilized that can identify motion signals from physiological, environmental, or other signals not directly associated with motion. In some embodiments of the present invention, at least one optical detector (e.g., 103, FIG. 1) may also serve as a motion sensor. Motion-related changes in scattered light (e.g., 111, FIG. 1) may be several times greater than blood-flow related changes in scattered light. Thus, the output of at least one detector 103 may be processed with a digital filter, such as a spectral filter, adaptive filter, threshold filter, or the like, to identify only motion-related signals and remove these signals from the desired response (e.g., 109, FIG. 1). Such processing may identify motion-related signals from physiological-related signals. In some embodiments of the present invention, by employing multiple optical detectors (e.g., 102, FIG. 1), motion-related signals may be identified from physiological-related signals by processing signals from the multiple detectors using an algorithm, such as a spectral algorithm. An example of a spectral processing algorithm for identifying motion-related signals, according to some embodiments of the present invention, is to generate a spectral representation of all signals in all detectors (e.g., 102, FIG. 1), identify key frequencies in each signal, and subtract, reduce, or remove all frequencies in common with each detector output. This type of filtering technique may work well because physiological signals may generate similar spectral peaks for all detectors (e.g., 102, FIG. 1) but motion signals may generate dissimilar spectral peaks in at least one detector (e.g., 103, FIG. 1). Another example of processing the detectors (e.g., 102, FIG. 1) to identify and remove motion-related signals is to position at least one detector in a location that does not "see" optical scatter (e.g., 111, FIG. 1) from the body/ear region but instead sees optical scatter from the earbud housing (e.g., 901, FIGS. 9A, 9B) or other material that may move in synchronization with the body. For example, the secondary sensor 730 (FIG. 7) may be an optical detector that measures light scattered from the earbud itself; because the sensor 730 may be facing the earbud and not the ear, only light scatter from the earbud may be detected.

Figure 22C:
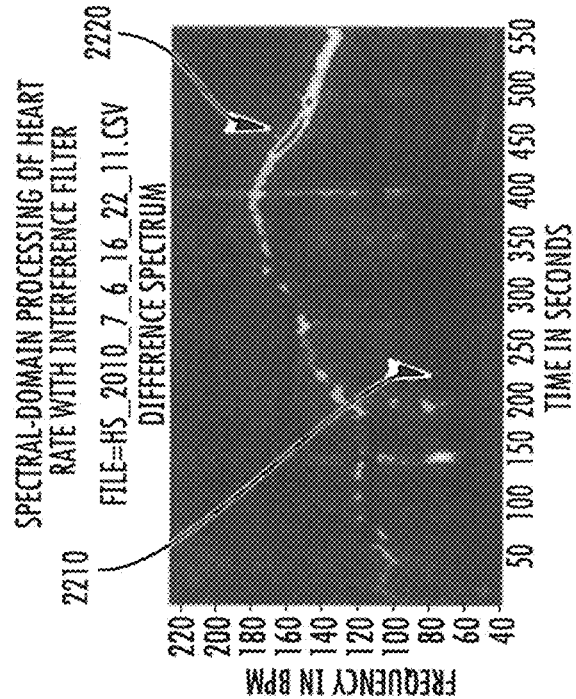
FIGS. 22A-22D are graphs of the processed heart rate signal output of an earbud module employing two different filter configurations, according to some embodiments of the present invention.
Figure 22D:
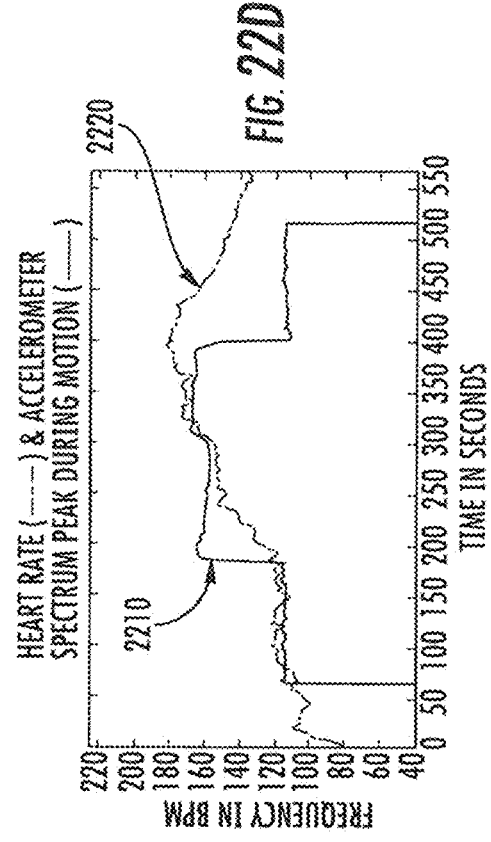
Figure 22A:
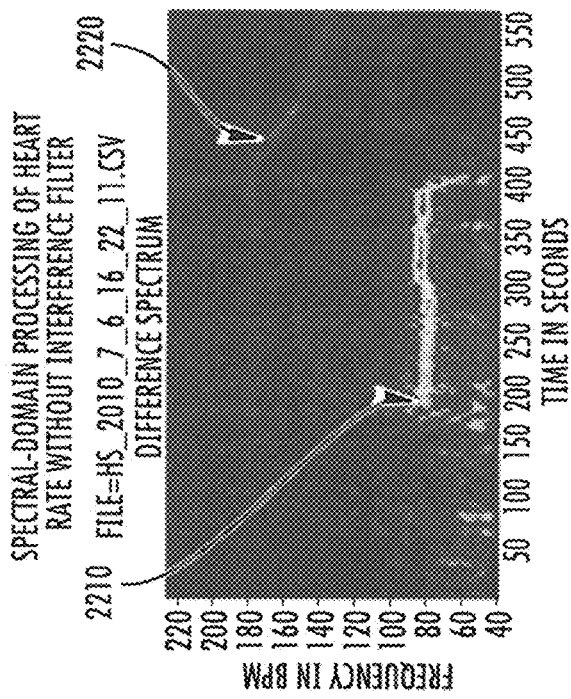
Figure 22B:
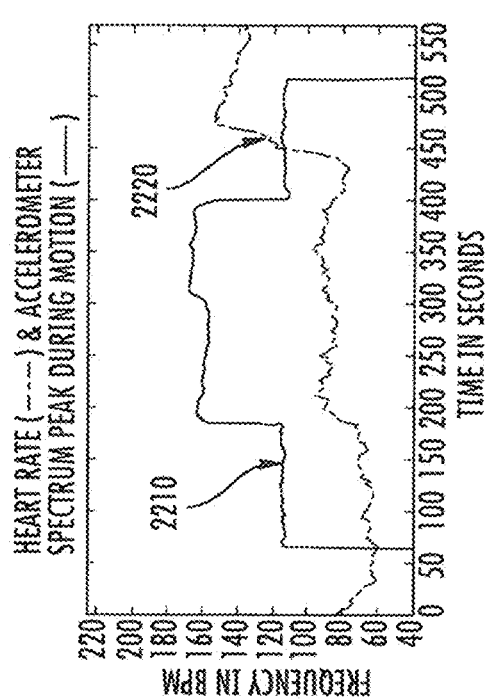

FIGS. 22A-22D are graphs of a processed heart rate signal output 109 of an earbud module (e.g., earbud module 207, 700, FIGS. 2, 7) employing two different filter configurations, according to some embodiments of the present invention. The graphs illustrated in FIGS. 22A-22D were generated from data collected from a user wearing an earbud (e.g., 404, FIGS. 4A, 4B) during an outdoor run. FIGS. 22A and 22C show relative spectrograms of frequency vs. time, where the strongest spectral signals show the brightest relative intensities. FIGS. 22B and 22D show the estimates of step rate 2210 and heart rate 2220 following further processing 107 to extract the desired frequencies of interest. FIG. 22A shows the spectrogram of the digitized sensor output from an optical detector (e.g., 103, FIG. 1) following the ADC process (e.g., 105, FIG. 1) without employing an interference filter (e.g., 106, FIG. 1). FIG. 22C shows the spectrogram of the same digitized sensor output of FIG. 22A following signal processing via the interference filter 2130 of FIG. 21. FIG. 22A shows a great deal of broadband noise from sunlight, the strongest signal appears to be the step rate signal 2210, and the heart rate spectrum 2220 appears very faint with respect to the step rate signal. In contrast, FIG. 22C shows substantially less broadband noise from sunlight, the strongest signal appears to be the heart rate signal 2220, and the step rate signal 2210 appears very faint with respect to the heart rate signal. Through further filtering (e.g., 107, FIG. 1), the heart rate 2220 and step rate 2210 may be extracted, as shown in FIGS. 22B and 22D. FIG. 22B shows that the estimated heart rate signal 2200 is incorrect and does not match that of the spectrogram illustrated in FIG. 22A. In contrast, FIG. 22D shows that the estimated heart rate signal 2200 is correct and does match that of the spectrogram illustrated in FIG. 22C. Namely, the advanced interference filter 2130 is able to remove enough unwanted sunlight interference that the heart rate spectrum may be more easily extracted by spectral algorithms 107 (FIG. 1) designed to pick out the strongest frequency as heart rate.

Monitoring apparatus, according to embodiments of the present invention can be adapted to fit around various parts of the body, such as an arm, leg, neck, etc. For example, monitoring apparatus, according to embodiments of the present invention can be implemented as a substrate, such as a wristband, armband, legband, neckband, waistband, ankleband, footband, handband, ringband, headband, or the like. The substrate may be flexible and may be configured to surround all or a portion of a body of a subject. The substrate may be configured to be attached to a body of a subject adhesively, similar to a bandage. The location of a sensor module (e.g., 700, 800) may be virtually any place along the skin of a subject; however, better PPG results may be obtained when a sensor module is placed along an major artery.

Figure 24:
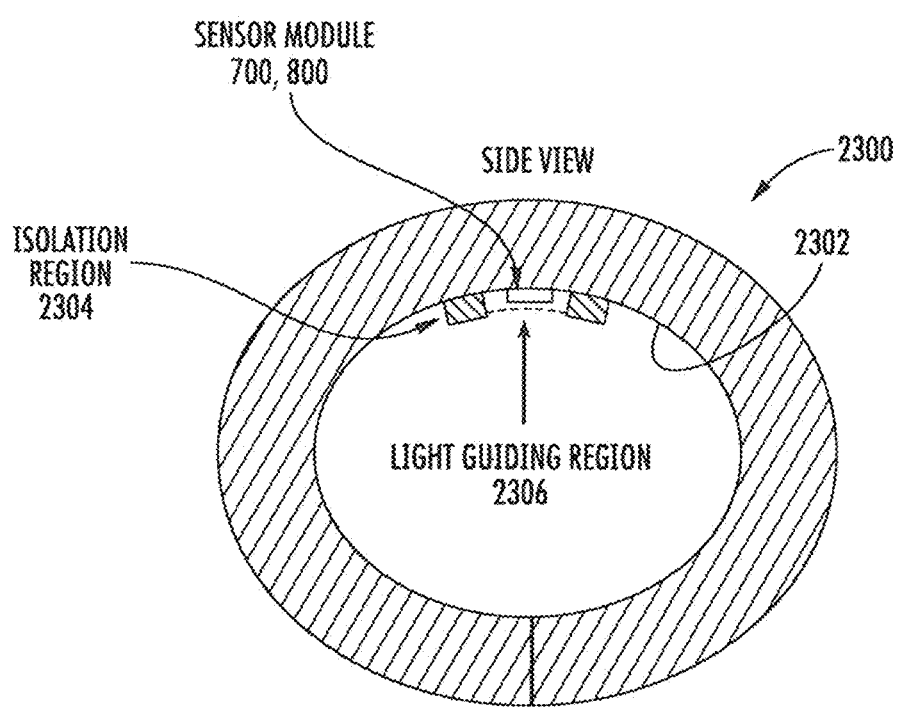
FIG. 24 is a side view of the monitoring apparatus of FIG. 23.

Referring to FIGS. 23-29, an exemplary wristband monitoring apparatus 2300 is illustrated. The wristband 2300 houses a power source, circuitry, a sensor module, and electronics as described above with respect to the various earbud embodiments. As illustrated in FIG. 24, a sensor module 700, 800 is positioned on the inside surface 2302 of the wristband 2300. The sensor module 700, 800 may include an isolation region 2304 that is configured to keep the sensor module 700, 800 stable with respect to the subject's wrist during use so as to reduce motion artifacts. The isolation region may be constructed out of any sturdy material, but for comfort, a foamy and/or flexible sturdy material may be utilized. Furthermore, the isolation region 2304 may further shield against environmental interference such as sunlight, external temperature, wind, and the like.

Figure 27:
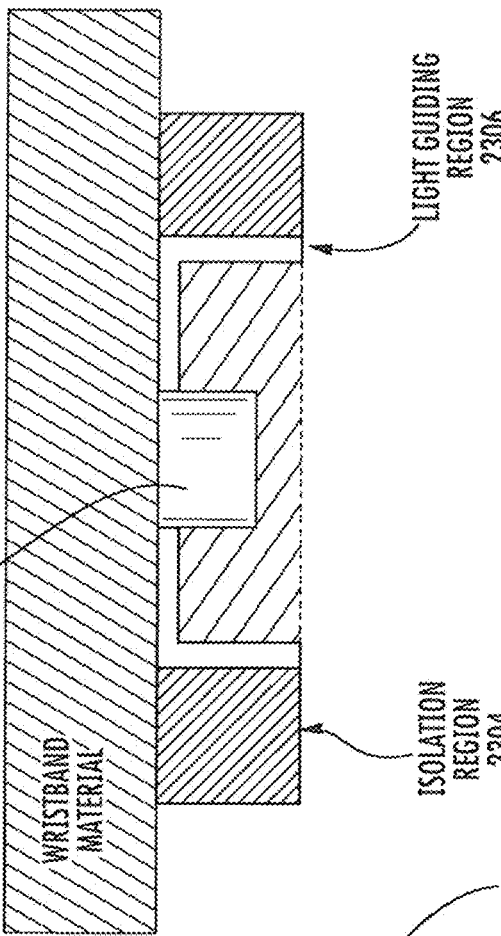
FIG. 27 is an enlarged side view of the sensor module of the monitoring apparatus of FIG. 23.
Figure 26:
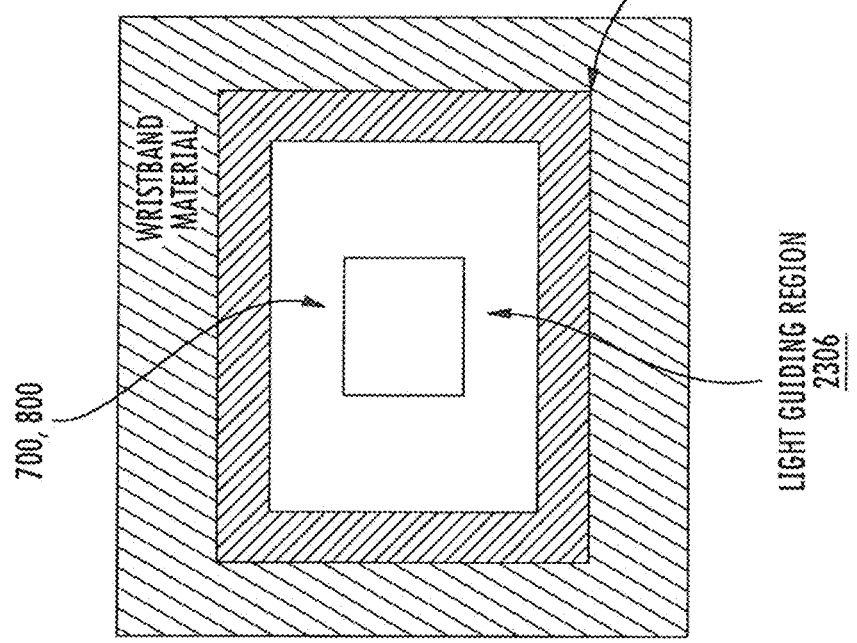
FIG. 26 is an enlarged plan view of the sensor module of the monitoring apparatus of FIG. 23.

In some embodiments of the present invention, a light guiding region 2306 may surround or partially surround the sensor module 700, 800 and/or isolation region 2304, as illustrated in FIGS. 24-27. In FIGS. 24-26, the light guiding region 2306 surrounds the sensor module 700, 800. In FIG. 27, the light guiding region 2306 partially surrounds the sensor module 700, 800. The light guiding region 2306 helps direct light to and/or from the sensor module 700, 800 and a blood flow region within the body part. In some embodiments, the light guiding region 2306 may be a reflector, such as a metal, metallic alloy, mylar, mica, reflective plastic, reflective textile, or the like. In other embodiments, the light guiding region 2306 may be a transparent light guide, such as transparent silicone, polymers, rubbers, textiles, glass, epoxies, glues, or the like. In the case of a reflective layer, the sensor module 700, 800 is at least partially exposed. In the case of a transparent light-guiding layer, the sensor module 700, 800 may be completely covered.

Referring to FIGS. 28 and 29, the sensor module 700, 800 may be tilted with respect to a body part region (e.g., the wrist area) of a subject. In the illustrated embodiments of FIGS. 28 and 29, the sensor module 700, 800 is tilted towards the wrist (away from the upper arm). The embodiment illustrated in FIG. 28 has a light guiding region 2306 with a different configuration from the light guiding region 2306 illustrated in the embodiment of FIG. 29. The tilting of the sensor module 700, 800 serves at least the following functions: 1) protection from sunlight and 2) improvement of coupling between light from the sensor module 700, 800 and blood flow in the body part (i.e., wrist area). Sunlight immunity may be improved in this fashion because a human's wrist is typically pointed away from sunlight, and so pointing the sensor module down along the arm may help prevent environmental (i.e., sunlight) interference. Also, pointing the sensor module 700, 800 towards the wrist may increase the surface area of blood flow exposed to the sensor module 700, 800, thus increasing the blood flow signal intensity for PPG and the like.

The processing of signals generated by the sensor module 700, 800 in the wristband embodiments of FIGS. 23-29 may be similar or identical to that described above with respect to the earbud embodiments.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A headset, comprising:
a housing defining an audio cavity, wherein the housing comprises first and second openings;
a speaker located within the audio cavity, wherein the housing comprises at least one aperture through which sound from the speaker can pass; and
first and second sensor modules within the housing in spaced-apart, angled relationship to each other, wherein the first sensor module is in communication with the first opening and is configured to direct electromagnetic radiation at a first target region of an ear of a person wearing the headset and to detect a first energy response signal therefrom, wherein the second sensor module is in communication with the second opening and is configured to direct electromagnetic radiation at a second target region of the ear and to detect a second energy response signal therefrom, wherein a direction normal to the first opening is angled relative to a direction from the speaker to the at least one aperture in the housing by less than ninety degrees (90°), and wherein a direction normal to the second opening is angled relative to the direction from the speaker to the at least one aperture in the housing by less than ninety degrees (90°).

2. The headset of claim 1, wherein the first and second sensor modules are on opposing sides of the direction from the speaker to the at least one aperture.

3. The headset of claim 1, wherein the first and second sensor modules each comprise at least one optical emitter and at least one optical detector, wherein the at least one optical emitter of each of the first and second sensor modules is selected from the group consisting of laser diodes (LDs), light-emitting diodes (LEDs), and organic light-emitting diodes (OLEDs).

4. The headset of claim 3, wherein each of the first and second optical sensor modules comprises light-opaque material configured to prevent ambient light from interfering with the respective at least one optical detector.

5. The headset of claim 3, wherein each of the first and second optical sensor modules comprises light-opaque material at least partially surrounding the respective at least one optical emitter and the respective at least one optical detector such that the respective at least one optical emitter and the at least one optical detector are not in direct optical communication with each other.

6. The headset of claim 1, further comprising at least one processor that controls operations of the first and second sensor modules, and that is configured to process the detected energy response signals.

7. The headset of claim 1, further comprising first and second lenses, wherein the first lens is configured to guide the electromagnetic radiation from the first sensor module towards the first target region of the ear and to direct the first energy response signal from the first target region to the first sensor module, and wherein the second lens is configured to guide the electromagnetic radiation from the second sensor module towards the second target region of the ear and to direct the second energy response signal from the second target region to the second sensor module.

8. The headset of claim 1, wherein the first energy response signal and the second energy response signal are each associated with one or more physiological metrics of the subject, and wherein the one or more physiological metrics comprise one or more of the following: heart rate, pulse pressure, respiration rate, lactic threshold, blood pressure, volume of blood flow through a blood vessel, blood metabolite level, blood oxygen level, blood gas level, glucose, and size of at least one blood vessel.

9. The headset of claim 1, further comprising:
a pulsed driving circuit configured to cause each of the first and second sensor modules to generate periodic time-varying pulses of the electromagnetic radiation having on and off states; and
an analog-to-digital converter configured to digitize an analog output of each of the first and second optical sensor modules.

10. The headset of claim 1, wherein the headset is an earbud.

11. The headset of claim 1, wherein the headset is a hearing aid.

12. A headset, comprising:
a housing defining an audio cavity;
a speaker located within the audio cavity, wherein the housing comprises at least one aperture through which sound from the speaker can pass, and wherein the housing comprises first and second openings on opposite sides of the at least one aperture, wherein a direction normal to the first opening is angled relative to a direction normal to the second opening, wherein the direction normal to the first opening is angled relative to a direction from the speaker to the at least one aperture in the housing by less than ninety degrees (90°), and wherein the direction normal to the second opening is angled relative to the direction from the speaker to the at least one aperture in the housing by less than ninety degrees (90°); and
first and second optical sensor modules within the housing in spaced-apart relationship to each other, wherein the first optical sensor module is configured to direct modulated light at a first target region of an ear of a person wearing the headset via the first opening and to detect a first energy response signal therefrom via the first opening, and wherein the second optical sensor module is configured to direct modulated light at a second target region of the ear via the second opening and to detect a second energy response signal therefrom via the second opening.

13. The headset of claim 12, wherein the first and second sensor modules each comprise at least one optical emitter and at least one optical detector, wherein the at least one optical emitter of each of the first and second sensor modules is selected from the group consisting of laser diodes (LDs), light-emitting diodes (LEDs), and organic light-emitting diodes (OLEDs).

14. The headset of claim 13, further comprising first and second lenses, wherein the first lens is configured to guide light from the at least one optical emitter of the first sensor module towards the first target region of the ear and to direct light from the first target region to the at least one optical detector of the first sensor module, and wherein the second lens is configured to guide light from the at least one optical emitter of the second sensor module towards the second target region of the ear and to direct light from the second target region to the at least one optical detector of the second sensor module.

15. The headset of claim 13, wherein each of the first and second optical sensor modules comprises light-opaque material configured to prevent ambient light from interfering with the respective at least one optical detector.

16. The headset of claim 13, wherein each of the first and second optical sensor modules comprises light-opaque material at least partially surrounding the respective at least one optical emitter and the respective at least one optical detector such that the respective at least one optical emitter and the at least one optical detector are not in direct optical communication with each other.

17. The headset of claim 13, further comprising:
a pulsed driving circuit configured to cause the at least one optical emitter of each of the first and second optical sensor modules to generate periodic time-varying pulses of light having on and off states; and
an analog-to-digital converter configured to digitize an analog output of the at least one optical detector of each of the first and second optical sensor modules.

18. The headset of claim 12, further comprising at least one processor that controls operations of the first and second optical sensor modules, and that is configured to process the detected first and second energy response signals.

19. The headset of claim 12, wherein the first energy response signal and the second energy response signal are each associated with one or more physiological metrics of the subject, and wherein the one or more physiological metrics comprise one or more of the following: heart rate, pulse pressure, respiration rate, lactic threshold, blood pressure, volume of blood flow through a blood vessel, blood metabolite level, blood oxygen level, blood gas level, glucose, and size of at least one blood vessel.

20. The headset of claim 12, wherein the headset is an earbud.

21. The headset of claim 12, wherein the headset is a hearing aid.

22. The headset of claim 1, wherein the housing is configured to mate or engage with a concha of the ear of the person wearing the headset.

23. The headset of claim 12, wherein the housing is configured to mate or engage with a concha of the ear of the person wearing the headset.

* * * * *